US011655483B2

(12) United States Patent
Gao et al.

(10) Patent No.: US 11,655,483 B2
(45) Date of Patent: May 23, 2023

(54) USE OF NOVEL MIRNA-BINDING SITE CASSETTES FOR ANTIGEN-PRESENTING CELL DETARGETING OF TRANSGENE EXPRESSION BY RAAV GENE THERAPY VECTORS

(71) Applicant: University of Massachusetts, Boston, MA (US)

(72) Inventors: Guangping Gao, Westborough, MA (US); Phillip Tai, Worcester, MA (US); Manish Muhuri, Worcester, MA (US); Wei Zhan, Worcester, MA (US)

(73) Assignee: University of Massachusetts, Boston, MA (US)

( * ) Notice: Subject to any disclaimer, the term of this patent is extended or adjusted under 35 U.S.C. 154(b) by 0 days.

(21) Appl. No.: 17/581,306

(22) Filed: Jan. 21, 2022

(65) Prior Publication Data
US 2022/0235372 A1    Jul. 28, 2022

Related U.S. Application Data

(60) Provisional application No. 63/140,464, filed on Jan. 22, 2021.

(51) Int. Cl.
   *C12N 15/86* (2006.01)
   *A61K 31/7088* (2006.01)
   *C12N 15/113* (2010.01)

(52) U.S. Cl.
   CPC .......... *C12N 15/86* (2013.01); *A61K 31/7088* (2013.01); *C12N 15/113* (2013.01); *C12N 2310/141* (2013.01); *C12N 2320/32* (2013.01); *C12N 2330/51* (2013.01); *C12N 2750/14143* (2013.01); *C12N 2750/14171* (2013.01)

(58) Field of Classification Search
   None
   See application file for complete search history.

(56) References Cited

U.S. PATENT DOCUMENTS

| 10,975,391 B2* | 4/2021 | Gao | ................. A61K 38/51 |
|---|---|---|---|
| 2018/0066279 A9 | 3/2018 | Gao et al. | |
| 2020/0040338 A1 | 2/2020 | Weiss et al. | |

FOREIGN PATENT DOCUMENTS

WO    WO 2014/100252    6/2014

OTHER PUBLICATIONS

Muhuri, et al. (2021) "Novel Combinatory MicroRNA-Binding sites in AAV vectors Synergistically Diminish Antigen Presentation and Transgene Immunity for Efficient and Stable Transduction", Frontiers in Immunology, 12: article 674242, 19 pages as printed. (Year: 2021).*

Invitation to Pay Additional Fees for Application No. PCT/US2022/013335, dated Apr. 13, 2022.
International Search Report and Written Opinion for Application No. PCT/US2022/013335, dated Jun. 10, 2022.
Bartel, MicroRNAs: genomics, biogenesis, mechanism, and function. Cell. Jan. 23, 2004;116(2):281-97. doi: 10.1016/s0092-8674(04)00045-5.
Boisgerault et al., Prolonged gene expression in muscle is achieved without active immune tolerance using microrRNA 142.3p-regulated rAAV gene transfer. Hum Gene Ther. Apr. 2013;24(4):393-405. doi: 10.1089/hum.2012.208.
Brown et al., Endogenous microRNA regulation suppresses transgene expression in hematopoietic lineages and enables stable gene transfer. Nat Med. May 2006;12(5):585-91. doi: 10.1038/nml398. Epub Apr. 23, 2006.
Chen et al., MicroRNAs modulate hematopoietic lineage differentiation. Science. Jan. 2, 2004;303(5654):83-6. doi: 10.1126/science.1091903. Epub Dec. 4, 2003.
Chenuaud et al., Autoimmune anemia in macaques following erythropoietin gene therapy. Blood. May 1, 2004;103(9):3303-4. doi: 10.1182/blood-2003-1 1-3845. Epub Jan. 22, 2004.
Danger et al., MicroRNAs, Major Players in B Cells Homeostasis and Function. Front Immunol. Mar. 11, 2014;5:98. doi: 10.3389/fimmu.2014.00098.
Daya et al., Gene therapy using adeno-associated virus vectors. Clin Microbiol Rev. Oct. 2008;21(4):583-93. doi: 10.1128/CMR.00008-08.
Fuchs et al., AAV-Delivered Antibody Mediates Significant Protective Effects against SIVmac239 Challenge in the Absence of Neutralizing Activity. PLoS Pathog. Aug. 6, 2015;11(8):e1005090. doi: 10.1371/journal.ppat.1005090. 20 pages.
Gao et al., Erythropoietin gene therapy leads to autoimmune anemia in macaques. Blood. May 1, 2004;103(9):3300-2. doi: 10.1 182/blood-2003-1 1-3852. Epub Dec. 24, 2003.
Geisler et al., Application of mutated miR-206 target sites enables skeletal muscle-specific silencing of transgene expression of cardiotropic AAV9 vectors. Mol Ther. May 2013;21(5):924-33. doi: 10.1038/mt.2012.276. Epub Feb. 26, 2013.
Georgiadis et al., AAV-mediated knockdown of peripherin-2 in vivo using miRNA-based hairpins. Gene Ther. Apr. 2010;17(4):486-93. doi: 10.1038/gt.2009.162. Epub Dec. 10, 2009.
Ginhoux et al., HLA-A*0201-restricted cytolytic responses to the rtTA transactivator dominant and cryptic epitopes compromise transgene expression induced by the tetracycline on system. Mol Ther. Aug. 2004;10(2):279-89. doi: 10.1016/j.ymthe.2004.05.012.
Johnson et al., Vector-mediated gene transfer engenders long-lived neutralizing activity and protection against SIV infection in monkeys. Nat Med. Aug. 2009;15(8):901-6. doi: 10.1038/nm.1967. Epub May 17, 2009.
Jooss et al., Transduction of dendritic cells by DNA viral vectors directs the immune response to transgene products in muscle fibers. J Virol. May 1998;72(5):4212-23. doi: 10.1128/JVI.72.5.4212-4223. 1998.
Le Guiner et al., Immune responses to gene product of inducible promoters. Curr Gene Ther. Oct. 2007;7(5):334-46. doi: 10.2174/156652307782151461.

(Continued)

*Primary Examiner* — Robert M Kelly
(74) *Attorney, Agent, or Firm* — Wolf, Greenfield & Sacks, P.C.

(57) ABSTRACT

The disclosure, in some aspects, relates to nucleic acids, compositions and kits useful for gene therapy with reduced immune response to transgene products.

19 Claims, 33 Drawing Sheets
Specification includes a Sequence Listing.

(56) References Cited

OTHER PUBLICATIONS

Mays et al., The complex and evolving story of T cell activation to AAV vector-encoded transgene products. Mol Ther. Jan. 2011;19(1):16-27. doi: 10.1038/mt.2010.250. Epub Nov. 30, 2010.

Mendell et al., Dystrophin immunity in Duchenne's muscular dystrophy. N Engl J Med. Oct. 7, 2010;363(15):1429-37. doi: 10.1056/NEJMoa1000228.

Pasquinelli, MicroRNAs and their targets: recognition, regulation and an emerging reciprocal relationship. Nat Rev Genet. Mar. 13, 2012;13(4):271-82. doi: 10.1038/nrg3162.

Qiao et al., Liver-specific microRNA-122 target sequences incorporated in AAV vectors efficiently inhibits transgene expression in the liver. Gene Ther. Apr. 2011;18(4):403-10. doi: 10.1038/gt.2010.157. Epub Dec. 9, 2010. Author Manuscript. 19 pages.

Samulski et al., AAV-Mediated Gene Therapy for Research and Therapeutic Purposes. Annu Rev Virol. Nov. 2014;1(1):427-51. doi: 10.1146/annurev-virology-031413-085355.

Squadrito et al., MicroRNA-mediated control of macrophages and its implications for cancer. Trends Immunol. Jul. 2013;34(7):350-9. doi: 10.1016/j.it.2013.02.003. Epub Mar. 13, 2013. Author Manuscript. 23 pages.

Turner et al., MicroRNAs regulate dendritic cell differentiation and function. J Immunol. Oct. 15, 2011;187(8):3911-7. doi: 10.4049/jimmunol.1101137.

Wang et al., Systemic protein delivery by muscle-gene transfer is limited by a local immune response. Blood. Jun. 1, 2005;105(11):4226-34. doi: 10.1182/blood-2004-03-0848. Epub Feb. 15, 2005.

Xiao et al., Circumventing cellular immunity by miR142-mediated regulation sufficiently supports rAAV-delivered OVA expression without activating humoral immunity. JCI Insight. May 21, 2019;5(13):e99052. doi: 10.1172/jci.insight.99052. 14 pages.

Xie et al., MicroRNA-regulated, systemically delivered rAAV9: a step closer to CNS-restricted transgene expression. Mol Ther. Mar. 2011;19(3):526-35. doi: 10.1038/mt.2010.279. Epub Dec. 21, 2010.

* cited by examiner

Vectors

| AAV1.CB6.PI.OVA | AAV1.CB6.PI.OVA.142BS |
| AAV1.OVA.miR223BS | AAV1.CB6.PI.OVA.miR142-223-3pBS |
| AAV1.OVA.miR-652-5pBS | AAV1.CB6.PI.OVA.miR142-652BS |
| AAV1.empty | PBS |

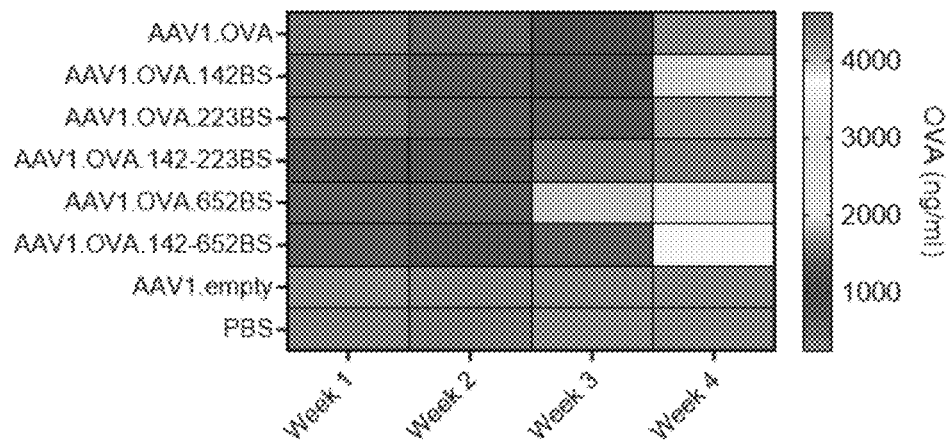
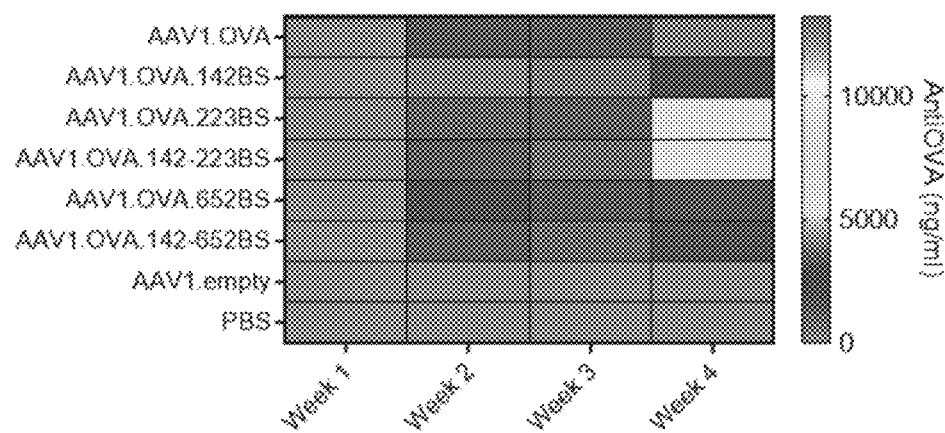
FIG. 3C

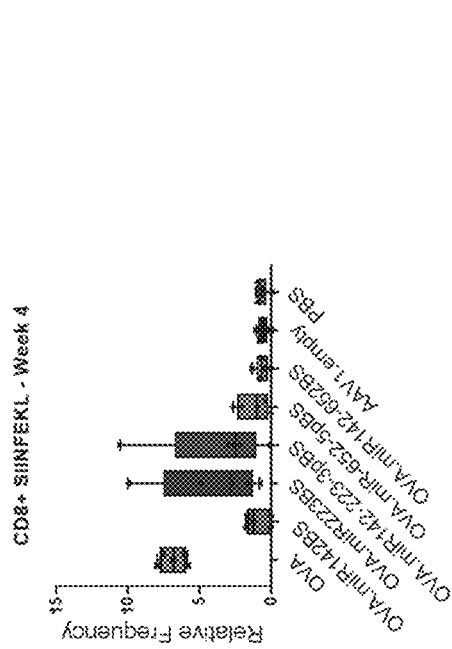
FIG. 5B
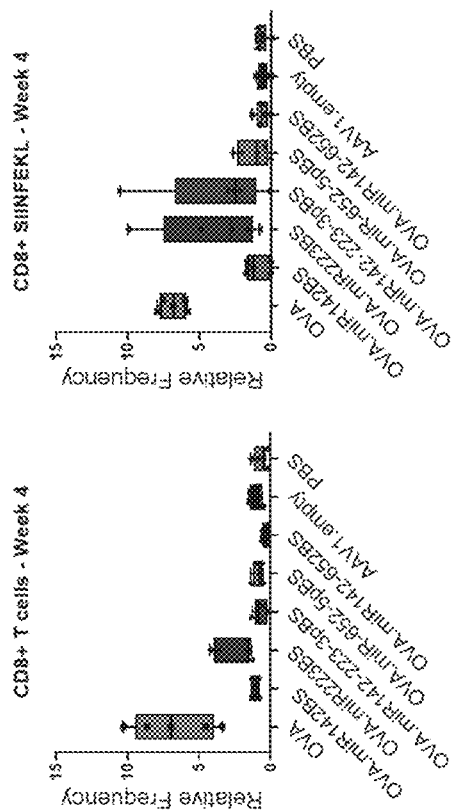
FIG. 5A
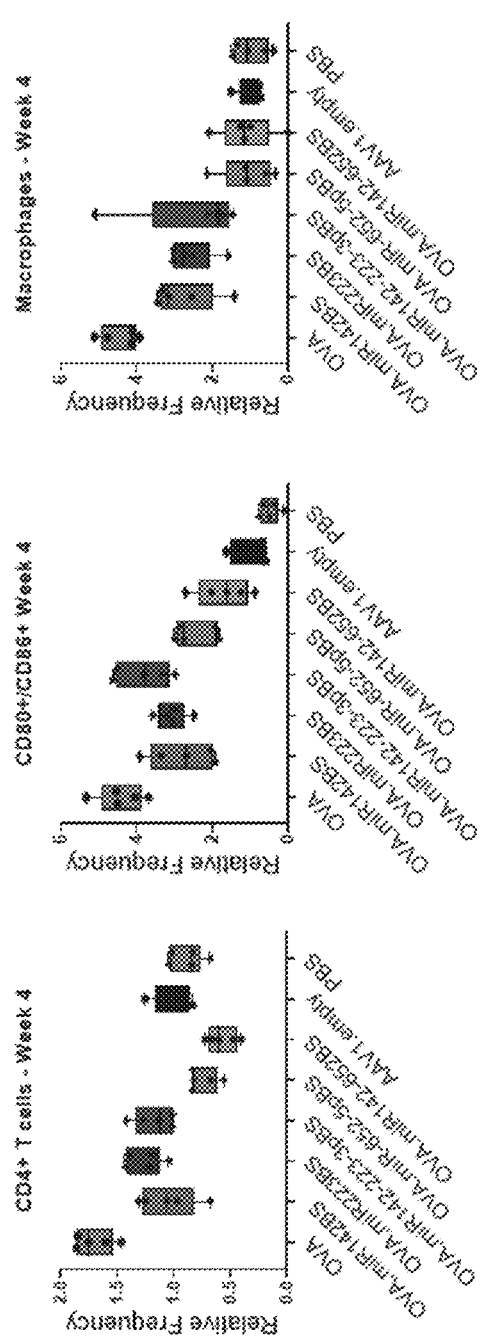
FIG. 5E
FIG. 5D
FIG. 5C

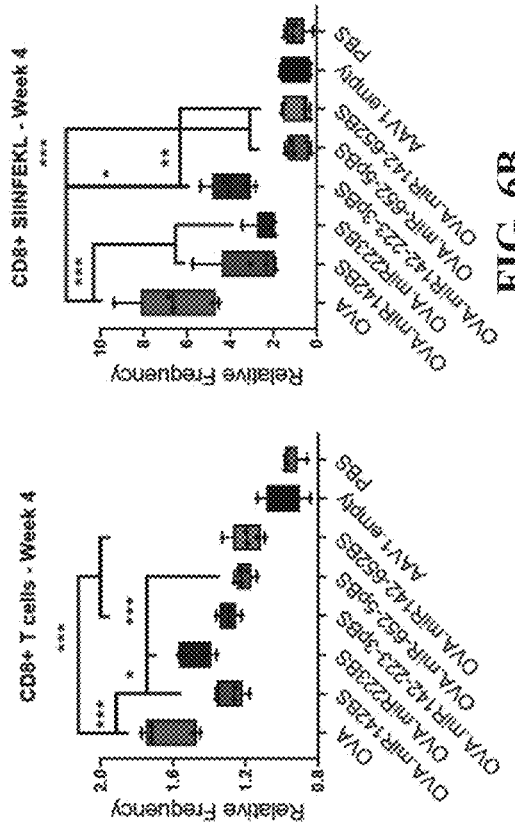
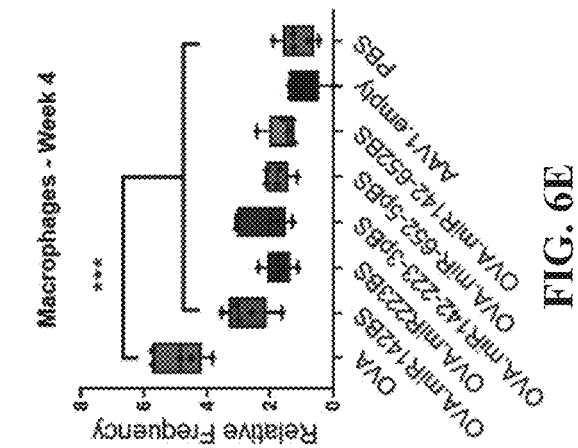
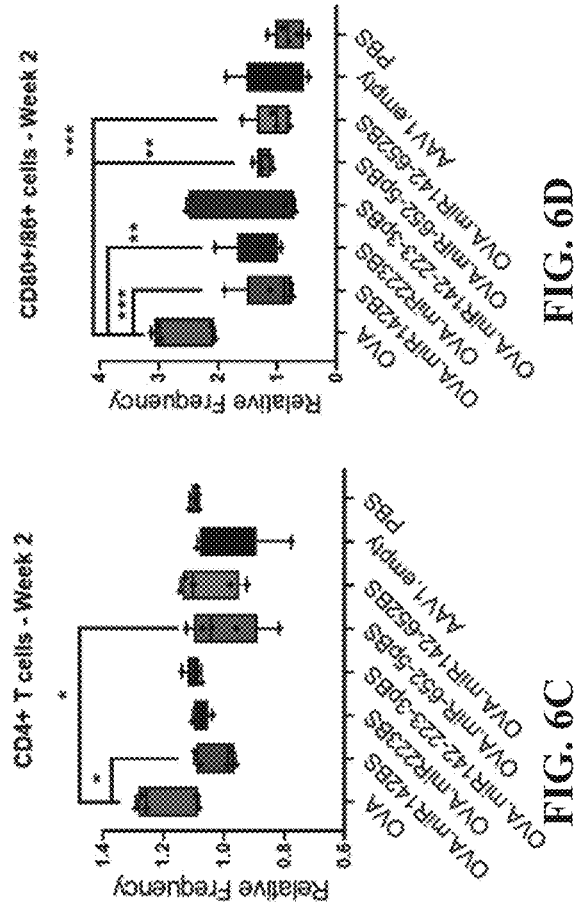
FIG. 6A
FIG. 6B
FIG. 6C
FIG. 6D
FIG. 6E

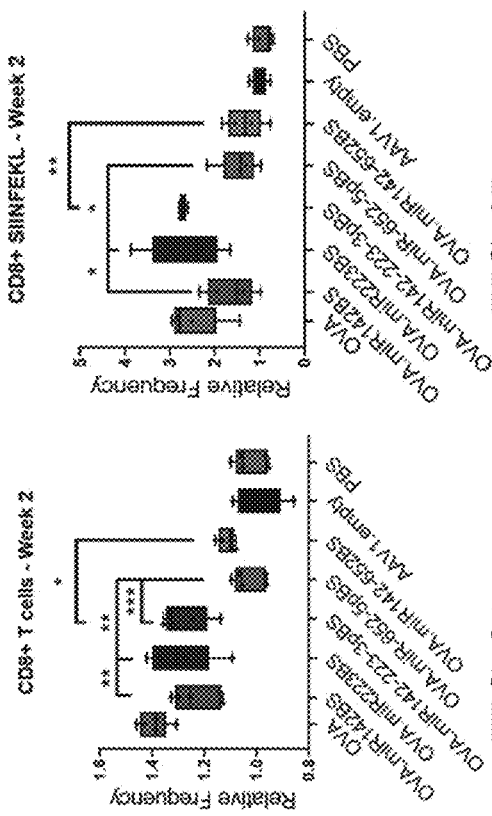
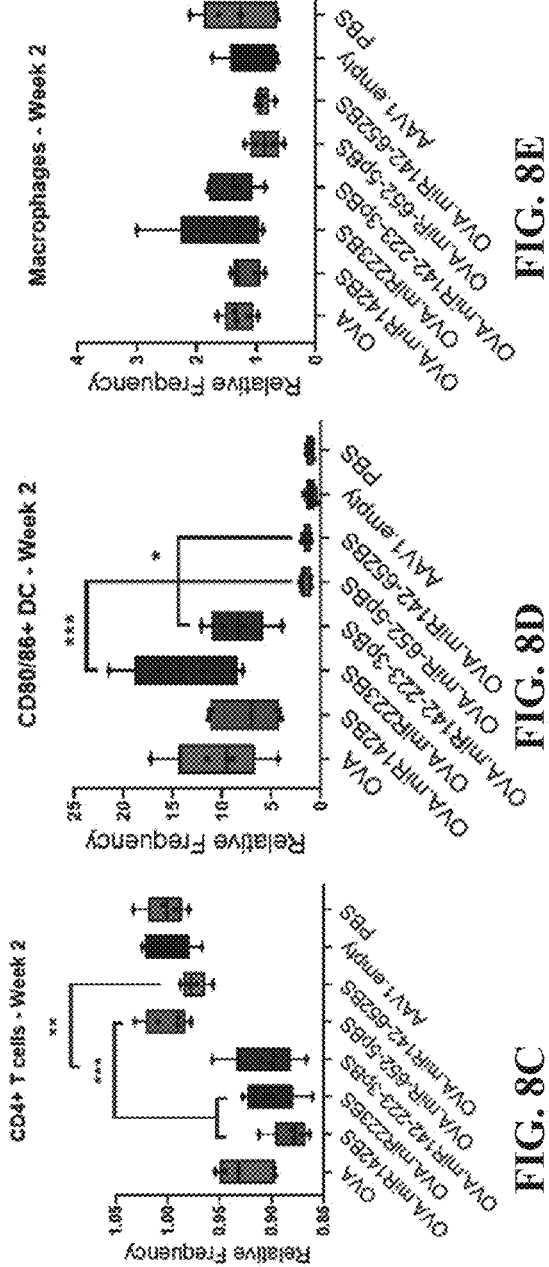
FIG. 8A
FIG. 8B
FIG. 8C
FIG. 8D
FIG. 8E

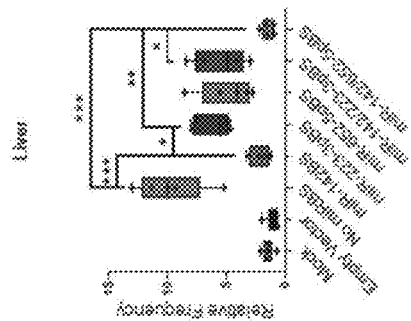
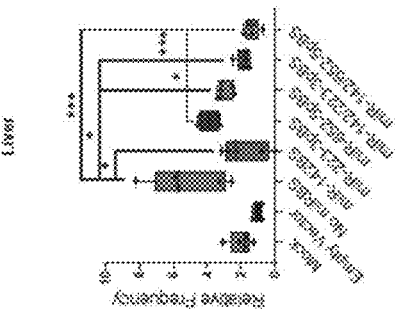
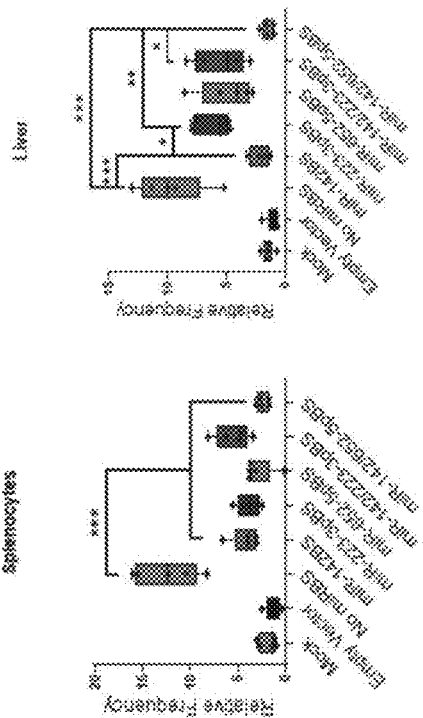
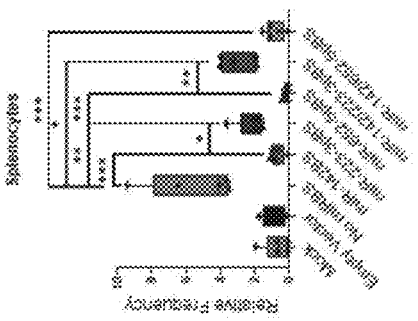
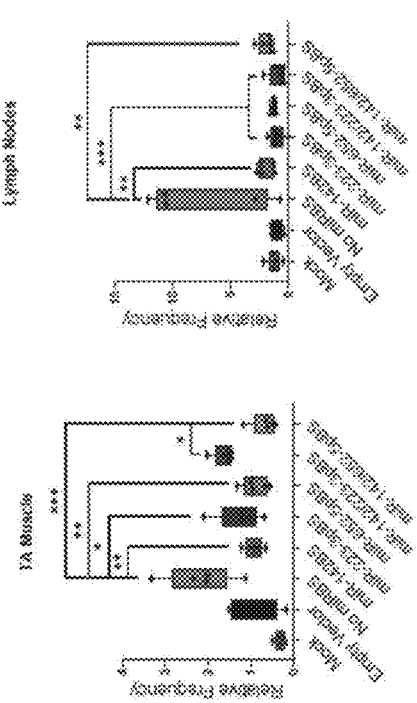
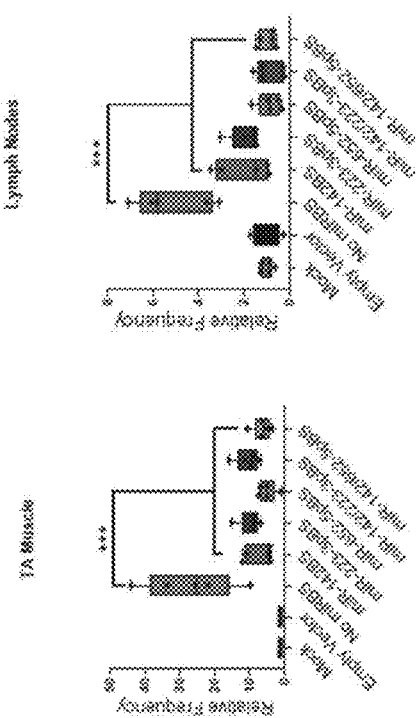
FIG. 12A  FIG. 12B  FIG. 12C  FIG. 12D
FIG. 12E  FIG. 12F  FIG. 12G  FIG. 12H

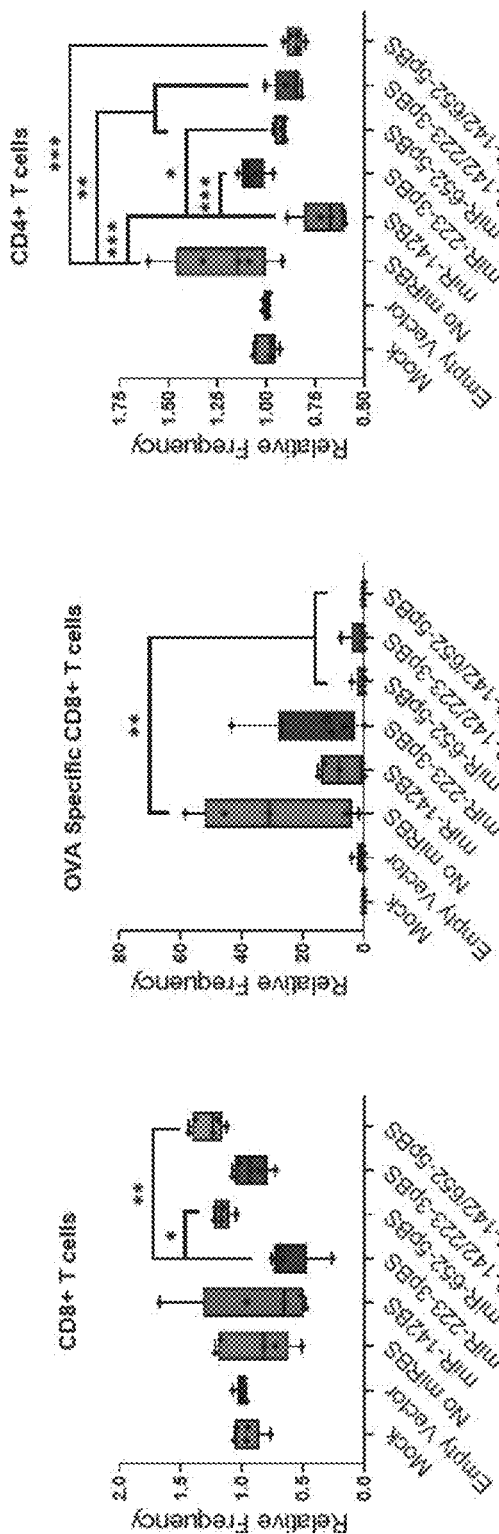
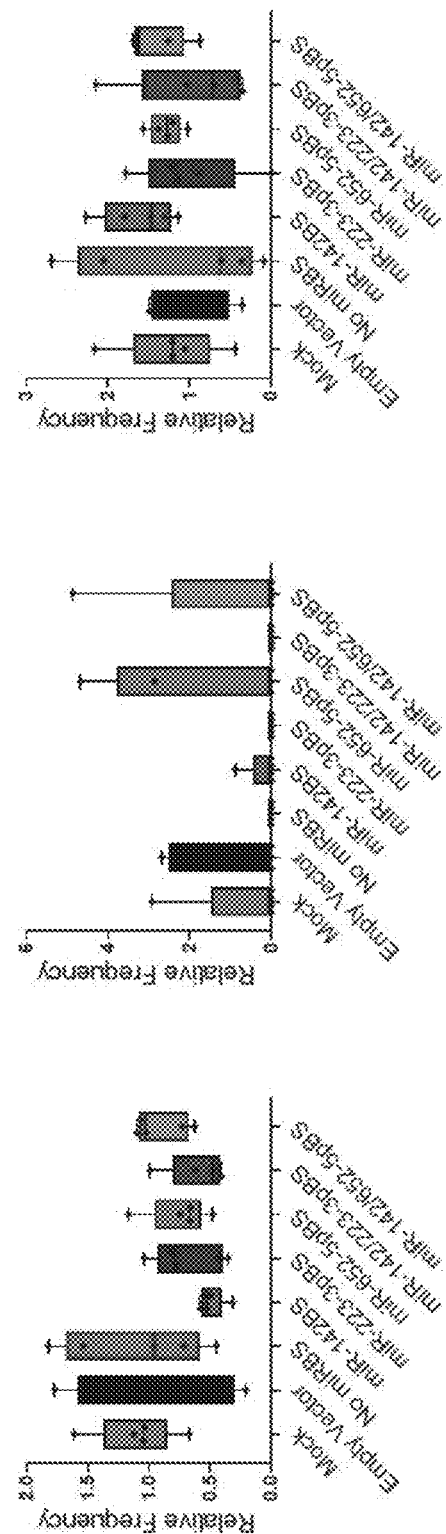

USE OF NOVEL MIRNA-BINDING SITE CASSETTES FOR ANTIGEN-PRESENTING CELL DETARGETING OF TRANSGENE EXPRESSION BY RAAV GENE THERAPY VECTORS

CROSS REFERENCE TO RELATED APPLICATIONS

This application claims the benefit under 35 U.S.C. 119(e) of U.S. Provisional Application No. 63/140,464, filed Jan. 22, 2021, entitled "USE OF NOVEL MIRNA-BINDING SITE CASSETTES FOR ANTIGEN-PRESENTING CELL DETARGETING OF TRANSGENE EXPRESSION BY RAAV GENE THERAPY VECTORS," the entire disclosure of which is hereby incorporated by reference in its entireties.

FEDERALLY SPONSORED RESEARCH DEVELOPMENT

This invention was made with government support under grant nos. AI121135, HD080642, HL131471, HL147367 and NS076991 awarded by the National Institutes of Health. The Government has certain rights in the invention.

REFERENCE TO A SEQUENCE LISTING SUBMITTED AS A TEXT FILE VIA EFS-WEB

The instant application contains a sequence listing which has been submitted in ASCII format via EFS-web and is hereby incorporated by reference in its entirety. The ASCII file, created on Jan. 20, 2022 is named U012070154W000-SEQ-SXT and is 24,203 bytes in size.

BACKGROUND

Gene therapy is an approach for delivering therapeutic genes to treat human diseases. Adeno-associated viral (AAV) vector is one of the most promising gene transfer vehicles for different therapeutic applications. AAVs can deliver and express genes in a wide variety of tissue and cell types, including muscle. Additional evidence has demonstrated that these AAVs can mediate persistent, long term expression of the transgenes in animals. Recently, clinical trials using AAV have shown beneficial effects and few side effects in human. However, improved methods of AAV based gene therapy are needed.

SUMMARY

Aspects of the disclosure relate to a recognition that therapeutic gene delivery may lead to inadvertent autoimmunity to endogenous and transgene derived products. For example, a B cell response to a transgene product may result in inhibitory antibodies against the transgene, thereby impairing the treatment. Aspects of the disclosure also relate to a recognition that immunotoxicity may result from inadvertent transduction of antigen presenting cells (APCs), such as dendritic cells, macrophages, and B-lymphocytes. This inadvertent transduction may trigger host immunity towards transgene products. Dendritic cells (DCs) have a broad range of antigen presentation and may represent a key APC in the host. Virally transduced DCs can directly display peptide epitopes on MHC class I molecules after cellular processing. The mature DCs display peptide antigens through MHC class I molecule activated cytotoxic CD8+T lymphocytes (CTLs). Therefore, aspects of the disclosure, provided methods for reducing transgene expression in APCs, such as DCs. In some embodiments, methods are provided that avoid transgene related immune responses in viral transduction, for example, using recombinant Adeno-Associated Viruses (rAAVs).

Accordingly, the disclosure in some aspects relates to rAAVs, nucleic acids, compositions, kits and related methods useful for performing gene therapy in a manner that reduces the likelihood that an undesirable immune response will occur against therapeutic transgene products. For example, aspects of the disclosure relate to methods of delivering a transgene to target cells of a subject in a manner that minimizes immune responses in the subject against a product of the transgene.

In some aspects the disclosure provides a method of delivering a transgene to target cells of a subject, the method comprising administering to the subject a recombinant Adeno-Associated Virus (rAAV) comprising a transgene, wherein the transgene comprises a promoter operably linked to a nucleic acid sequence that encodes an RNA transcript that comprises at least one immune-associated miRNA binding site, wherein the rAAV infects target cells of the subject thereby delivering the transgene to the target cells, wherein the at least one immune-associated miRNA binding site is a miR-652-5pBS, alone or in combination with one or more of the following miRNA binding sites: a miR-33-5pBS, a miR-223BS, or a miR142BS.

In some embodiments, the presence of the at least one immune-associated miRNA binding site results in a lower immune response in the subject against a product of the RNA transcript compared with the level of an immune response in a control subject that has been administered a control rAAV comprising a transgene engineered to express a control RNA transcript encoding the product, wherein the control RNA transcript does not comprise immune-associated miRNA binding sites.

In some embodiments, the lower immune response comprises a lower level of antibodies that bind specifically to the product. In some embodiments, the lower immune response comprises a lower level of T lymphocytes, cytotoxic T lymphocytes, mature dendritic cells, or macrophages that bind specifically to the product and kill cells transduced by the rAAV.

In some embodiments, the lower immune response comprises a lower level of antigen presenting cells that display antigens of the product through MHC class I molecules.

In some embodiments, the at least one immune-associated miRNA is expressed in dendritic cells, macrophages, T-lymphocytes, B-lymphocytes, monocytes, myeloid cells, and/or MF.

In some embodiments, the RNA transcript comprises at least two immune-associated miRNA binding sites (BS).

In some embodiments, the RNA transcript comprises two to ten (e.g., 2, 3, 4, 5, 6, 7, 8, 9, or 10) different immune-associated miRNA binding sites.

In some embodiments, the rAAV further comprises a binding site for one of the following miRNAs: miR-106, miR-125a, miR-125b, miR-126a, miR-142, miR-146a, miR-15, miR-150, miR-155, miR-16, miR-17, miR-18, miR-181a, miR-19a, miR-19b, miR-20, miR-21a, miR-223, miR-24-3p, miR-29a, miR-29b, miR-29c, miR-302a-3p, miR-30b, miR-33-5p, miR-34a, miR-424, miR-652-3p, miR-652-5p, miR-9-3p, miR-9-5p, miR-92a, and miR-99b-5p (SEQ ID NOS: 1-33).

In some embodiments, the at least one miRNA binding site is miR-223-3p BS. In some embodiments, the binding site is encoded by a nucleic acid having the sequence set forth in SEQ ID NO: 38.

In some embodiments, the at least one miRNA binding site is miR-652-5p BS. In some embodiments, the binding site is encoded by a nucleic acid having the sequence set forth in SEQ ID NO: 39.

In some embodiments, the at least one miRNA binding site is a combination of miR-142BS and miR-652BS. In some embodiments, the binding site is encoded by a nucleic acid having the sequence set forth in SEQ ID NO: 40.

In some embodiments, the at least one miRNA binding site is a combination of miR-142BS and miR-33-5pBS.

In some embodiments, the at least one miRNA binding site is a combination of miR-142BS and miR-223-3pBS. In some embodiments, the binding site is encoded by a nucleic acid having the sequence set forth in SEQ ID NO: 41.

In some embodiments, the RNA transcript is a messenger RNA and at least one of the miRNA binding sites is present in the 3'-UTR of the messenger RNA.

In some embodiments, the RNA transcript is a messenger RNA and each of the miRNA binding sites is present in the 3'-UTR of the messenger RNA.

In some embodiments, the RNA transcript encodes a therapeutic protein.

In some embodiments, the combination of miR-142BS and miR-652BS results in Th1 and/or Th17 responses in the subject.

In some embodiments, the antigen presenting cells are dendritic cells, macrophages, T-lymphocytes, or B-lymphocytes.

In some aspects, the disclosure provides a recombinant Adeno-Associated Virus (rAAV) comprising a transgene encoding an RNA transcript that comprises at least one immune-associated miRNA binding sites, wherein the at least one immune-associated miRNA binding site is a miR-652-5pBS, alone or in combination with one or more of the following miRNA binding sites: a miR-33-5pBS, a miR-223BS, or a miR142BS.

In some embodiments, the RNA transcript comprises two different immune-associated miRNA binding sites.

In some embodiments, the RNA transcript comprises two to ten (e.g., 2, 3, 4, 5, 6, 7, 8, 9, or 10) different immune-associated miRNA binding sites.

In some embodiments, the rAAV comprises a binding site for one of the following miRNAs: miR-106, miR-125a, miR-125b, miR-126a, miR-142, miR-146a, miR-15, miR-150, miR-155, miR-16, miR-17, miR-18, miR-181a, miR-19a, miR-19b, miR-20, miR-21a, miR-223, miR-24-3p, miR-29a, miR-29b, miR-29c, miR-302a-3p, miR-30b, miR-33-5p, miR-34a, miR-424, miR-652-3p, miR-652-5p, miR-9-3p, miR-9-5p, miR-92a, and miR-99b-5p (SEQ ID NOS: 1-33).

In some embodiments, the rAAV comprises miR-223-3pBS. In some embodiments, the rAAV comprises a sequence corresponding to SEQ ID NO: 42.

In some embodiments, the rAAV comprises a miR-652-5pBS. In some embodiments, the rAAV comprises a sequence corresponding to SEQ ID NO: 43.

In some embodiments, the rAAV comprises a combination of miR-142BS and miR-652BS. In some embodiments, the rAAV comprises a sequence corresponding to SEQ ID NO: 44.

In some embodiments, the rAAV comprises a combination of miR-142BS and miR-223-3PBS. In some embodiments, the rAAV comprises a sequence corresponding to SEQ ID NO: 45.

In some embodiments, the at least one miRNA binding site is a combination of miR-142 and miR-33-5p.

In some embodiments, the RNA transcript is a messenger RNA and at least one of the miRNA binding sites is present in the 3'-UTR of the messenger RNA.

In some embodiments, the RNA transcript is a messenger RNA and each of the miRNA binding sites is present in the 3'-UTR of the messenger RNA.

In some embodiments, the RNA transcript encodes a therapeutic protein.

In some embodiments, the RNA transcript is an inhibitory RNA. In some embodiments, the inhibitory RNA is an shRNA, miRNA, antisense RNA, miRNA sponge or TuD RNA. In some embodiments, the miRNA is an artificial miRNA.

In some embodiments, the rAAV comprises a capsid of a serotype selected from: AAV1, AAV2, AAV3, AAV4, AAV5, AAV6, AAV7, AAV8, AAV9, AAV10, AAV11, AAV12, and variants thereof.

In some embodiments, the transgene is flanked by inverted terminal repeat (ITR) sequences.

In some aspects, the disclosure provides an rAAV vector comprising a transgene engineered to express an RNA transcript that comprises at least two immune-associated miRNA binding sites, wherein the transgene is flanked by inverted terminal repeat sequences of an adeno-associated virus, wherein the at least one immune-associated miRNA binding site is a miR-652-5pBS, alone or in combination with one or more of the following miRNA binding sites: a miR-33-5pBS, a miR-223BS, or a miR142BS.

In some embodiments, the RNA transcript comprises two to ten (e.g., 2, 3, 4, 5, 6, 7, 8, 9, or 10) different immune-associated miRNA binding sites.

In some embodiments, the rAAV vector further comprises a binding site for one of the following miRNAs: miR-106, miR-125a, miR-125b, miR-126a, miR-142, miR-146a, miR-15, miR-150, miR-155, miR-16, miR-17, miR-18, miR-181a, miR-19a, miR-19b, miR-20, miR-21a, miR-223, miR-24-3p, miR-29a, miR-29b, miR-29c, miR-302a-3p, miR-30b, miR-33-5p, miR-34a, miR-424, miR-652-3p, miR-652-5p, miR-9-3p, miR-9-5p, miR-92a, and miR-99b-5p (SEQ ID NOS: 1-33).

In some embodiments, the at least one miRNA binding site is miR-223-3p BS. In some embodiments, the binding site is encoded by a nucleic acid having the sequence set forth in SEQ ID NO: 38.

In some embodiments, the at least one miRNA binding site is miR-652-5p BS. In some embodiments, the binding site is encoded by a nucleic acid having the sequence set forth in SEQ ID NO: 39.

In some embodiments, the at least one miRNA binding site is a combination of miR-142BS and miR-652BS. In some embodiments, the binding site is encoded by a nucleic acid having the sequence set forth in SEQ ID NO: 40.

In some embodiments, the at least one miRNA binding site is a combination of miR-142BS and miR-33-5pBS.

In some embodiments, the at least one miRNA binding site is a combination of miR-142BS and miR-223-3pBS. In some embodiments, the binding site is encoded by a nucleic acid having the sequence set forth in SEQ ID NO: 41.

In some embodiments, the RNA transcript is a messenger RNA and at least one of the miRNA binding sites is present in the 3'-UTR of the messenger RNA.

In some embodiments, the RNA transcript is a messenger RNA and each of the miRNA binding site is present in the 3'-UTR of the messenger RNA.

In some embodiments, the RNA transcript encodes a therapeutic protein.

In some embodiments, the RNA transcript is an inhibitory RNA. In some embodiments, the inhibitory RNA is an shRNA, miRNA, or antisense RNA.

In some aspects, the disclosure provides a host cell comprising a nucleic acid as described herein. In some embodiments, the host cell is a mammalian cell.

In some embodiments, the subject is a human. In some embodiments, the administration is intramuscular.

BRIEF DESCRIPTION OF DRAWINGS

FIG. 1A shows a generic vector genome design harboring miRNA binding sites (miRBS). FIG. 1B depicts permissive transduction of rAAV into a non-immune host cell, such as a hepatocyte or myocyte. FIG. 1C shows high levels of endogenous miRNAs enriched in antigen-presenting cells (APCs) prohibit translation of transgenes in these transduced cell types.

FIG. 2A shows schematic of rAAV ovalbumin (OVA) expression vectors harboring miRNA binding sites (miRBS). FIG. 2B shows list of 33 miRNA candidates, in which the cells were enriched, and their cognate binding sequences incorporated into the OVA expression cassette. FIG. 2B shows a workflow for testing efficacy of APC detargeting. FIG. 2C shows heatmap of miRBS cassette activities tested in vitro. Myoblasts (C2C12), myocytes (dC2C12), macrophages (RAW264.7) and dendritic cells (JAWSII) were transiently transfected with AAV1-CB6-OVA constructs carrying 26 miRBS candidates as detailed in panel B (n=2). Candidates with high expression levels in myocytes and low expression in immune cells were preferred designs.

FIGS. 3A-3C show in vitro and in vivo screening of combinatorial miRBS. FIG. 3A shows heatmap of combinatorial miRBS cassette designs tested in cell culture. Candidate miRBS were tested as individual cassettes (two binding sites per cassette) or in combination with miR-142BS (two binding sites per miRBS motif, four total). Myoblasts (C2C12), myocytes (dC2C12), macrophages (RAW264.7) and dendritic cells (JAWSII) were transiently transfected with AAV1-CB6-OVA constructs carrying the miRBS cassettes as detailed in FIG. 2 (n=5). Candidates with high expression levels in myocytes and low expression in immune cells were preferred designs. FIG. 3B illustrates workflow for testing miR-BS cassettes in vivo. C57BL/6 male mice, 6 to 8 weeks of age were injected intramuscular administration with 6.8E10 vg/mouse (n=10 per group) on week 0, week 2 and week 4. A table of vectors tested is shown. FIG. 3C shows in vivo performances of novel individual and combinatorial miRBS cassette designs in rAAV vectors. Blood of treated mice was collected on a weekly bases for four weeks and was measured for circulating OVA (left) and anti-OVA IgG (right) by enzyme-linked immunosorbent assay (ELISA). Heatmap values represent means (n=10 per group).

FIGS. 5A-5E show effect of novel individual and combinatorial miRBS cassette designs in rAAV-OVA expression vectors on CD8, CD4, and CD80/CD86 co-stimulation and macrophages in injected TA (tibialis anterior) muscles. C57BL/6 male mice at 6- to 8-weeks old were injected by intramuscular (tibialis anterior, TA) injection of rAAV-OVA expression vectors at 6.8E10 vg/mouse. Mice were sacrificed at four weeks post-injection and injected muscles were harvested. Cells were subjected to flow cytometry to assess the percentages of CD8+ T cells (FIG. 5A), CD8+ T cells expressing OVA (SIINFEKL (SEQ ID NO: 46), FIG. 5B), CD4+ T cells (FIG. 5C), mature DCs (CD80/89+, FIG. 5D), and macrophages (FIG. 5E). Values are displayed as box plots representing means±SD, whiskers=min and max values (n=5 per group).

FIGS. 6A-6E depict the effect of novel individual and combinatorial miRBS cassette designs in rAAV-OVA expression vectors on CD8, CD4, and CD80/CD86 co-stimulation and macrophages in liver. C57BL/6 male mice at 6- to 8-weeks old were injected by intramuscular injection of rAAV-OVA expression vectors at 6.8E10 vg/mouse. Mice were sacrificed at four weeks post-injection and livers were harvested. Cells were subjected to flow cytometry to assess the percentages of CD8+ T cells (FIG. 6A), CD8+ T cells expressing OVA (SIINFEKL (SEQ ID NO: 46), FIG. 6B), CD4+ T cells (FIG. 6C) mature DCs (CD80/89+, FIG. 6D), and macrophages (FIG. 6E). Values are displayed as box plots representing means±SD, whiskers=min and max values (n=5 per group).

FIG. 7A and FIG. 7B show that C57BL/6 male mice at 6- to 8-weeks old were injected by intramuscular injection of rAAV-OVA expression vectors at 6.8E10 vg/mouse. Mice were sacrificed at two weeks (top) and four weeks (bottom) post-injection, and splenocytes were harvested. Cultured splenocytes were then stimulated with OVA and five hours post-stimulation, cells were assayed for Th1 (FIG. 7A) or Th17 (FIG. 7B) expression by flow cytometry. Bar graph values are displayed as means±SD, whiskers=min and max values (n=5 per group). Cytokine levels, IFN- (FIG. 7C), TNF-α (FIG. 7D), IL-17 (FIG. 7E), and IL-10 (FIG. 7F) secreted into the media were also assessed.

FIGS. 8A-8E show the effect of novel individual and combinatorial miRBS cassette designs in rAAV-OVA expression vectors on CD8, CD4, and CD80/CD86 co-stimulation and macrophages in splenocytes. C57BL/6 male mice at 6- to 8-weeks old were injected by intramuscular injection of rAAV-OVA expression vectors at 6.8E10 vg/mouse. Mice were sacrificed at two weeks post-injection and spleens were harvested. Splenocytes were subjected to flow cytometry to assess the percentages of CD8+ T cells (FIG. 8A), CD8+ T cells expressing OVA (SIINFEKL (SEQ ID NO: 46), FIG. 8B), CD4+ T cells (FIG. 8C), mature DCs (CD80/89+, FIG. 8D), and macrophages (FIG. 8E). Values are displayed as box plots representing means±SD, whiskers=min and max values (n=5 per group).

FIG. 11A shows endogenous miRNA expression levels in cultured mouse myoblasts (C2C12), myocytes (dC2C12), macrophages (RAW264.7), DCs (JAWSII), bone marrow derived macrophages (BMDM), primary mouse hepatocytes, and Kupffer cells as quantified by reverse transcription quantitative PCR (RT-qPCR) (n=3). rAAV1 expression vectors were injected intramuscularly (i.m.) on day 0 followed by serum collection every week for an eight-week period. (FIGS. 11B and C). FIGS. 11B and 11C show ELISA quantification of circulating OVA expression (FIG. 11B) and anti-OVA IgG1 (FIG. 11C) ($1 \times 10^{11}$ GCs/mouse, n=10). Single gradient heat map representing respective analyte levels (n=5) is shown in FIGS. 11D-F. ddPCR detection of rAAV vector genome copies in injected skeletal muscle (FIG. 11D), spleen (FIG. 11E), and liver (FIG. 11F) at eight weeks post-injection (n=5). Values represent mean±SD. *p<0.05, ***p<0.001, one-way ANOVA with Tukey's post hoc test.

FIGS. 12A-12H show that the incorporation of miR-142BS, miR-223BS, and miR-652BS into rAAV1.OVA transgene vectors reduced macrophage and DC activation. rAAV1.OVA expressing vectors with or without miR-BSs ($1 \times 10^{11}$ GCs/mouse) were delivered by i.m. injections into C57BL/6 mice. Four weeks after injection, cells were isolated from TAs, lymph nodes, spleens, and livers and stained for macrophage markers (CD11b+, F4/80+) and activated DCs (CD11c+, CD80+, CD86+) followed by flow cytometry analysis. Relative frequencies of macrophage populations (FIGS. 12A-D) and activated DCs (FIGS. 12E-H) are represented as box plots with means, first and third quartile boundaries, and whiskers indicating max and min values. (n=5). Mock=AAV1.empty capsid. p values were determined by one-way ANOVA with Tukey's post hoc test. *p<0.05, p<0.01, *p<0.001

FIGS. 14A and 14B show estimation of IFN-γ and TNF-α response to OVA stimulation (5 μg/mL) by splenocytes isolated from mice four weeks after vector injection. Three days after treatment, supernatants were collected and quantitated by ELISA (mean±SD, n=5). p values were determined by ANOVA with Tukey's post hoc test. Splenocytes isolated two and four weeks post-AAV1 injection were stimulated for 24 hours with OVA (5 μg/mL) and stained for detecting either Th1 population (CD4+) (FIGS. 14C and 14D) or Th17 cell population (CD4+IL-17A+) (FIGS. 14E and 14F) and analyzed by flow cytometry (Box plots with means, first and third quartile boundaries, and whiskers indicating max and min values; n=5). FIGS. 14E and 14F show that levels of secreted Th17-specific cytokines, IL-17 and IL-21-were assessed after stimulation of splenocytes (harvested four weeks post-injection) for 72 hours with OVA (5 μg/mL) by ELISA (mean±SD, n=5). *p<0.05, p<0.01, *p<0.001. p values were estimated by one-way ANOVA with Tukey's post hoc test.

FIGS. 15A-15C show that cells from TA muscle, lymph nodes and spleen were harvested from rAAV1 injected C57BL/6 mice four weeks after treatment and stained for Treg markers (CD4+, CD25+, FOXP3+). The frequencies of Tregs were quantified by flow cytometry and displayed as box and whisker plots (n=5). FIG. 15D shows that C57BL/6 male mice, six weeks old, were i.m. injected with rAAV1.OVA vectors with or without miRBS ($1 \times 10^{11}$ GCs/mouse, n=5) and sacrificed two weeks after injection to harvest muscles. Tissue sections were stained for H&E (upper panels, original magnification: 20×), CD8 and granzyme B (lower panels: DAPI, blue; red, granzyme B, red; and CD8, green; original magnification: 40×). Scale bars=200 μm (H&E images), 50 μm (fluorescence images). FIG. 15E shows quantification of H&E images for nuclear infiltrates in whole tissue section at original magnification of ×20. FIGS. 15F and 15G show that quantification of CD8 (FIG. 15F) and granzyme B (FIG. 15G) images in four fields at original magnification of 40×. p values were estimated by one-way ANOVA with Tukey's post hoc test. *p<0.05, p<0.01, *p<0.001.

Figure 17A:
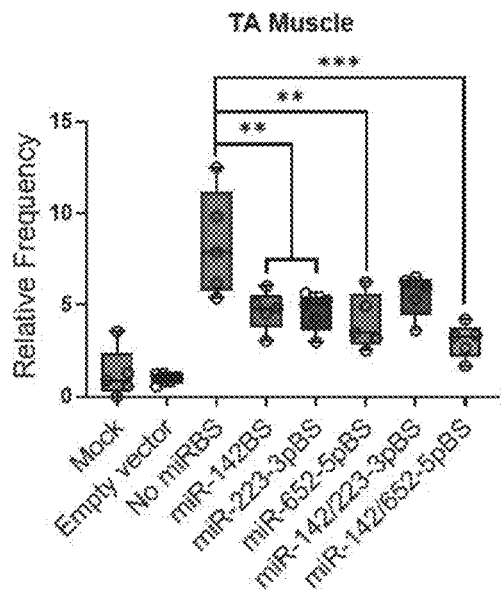
FIGS. 17A-17D show that miR-BS incorporation mediated robust reduction of DC activation. Six-week-old C57BL/6 male mice were injected by i.m with PBS (mock), empty caspid, rAAV1.OVA, or rAAV1.OVA.miR-BS vectors (1x1011 GC/mouse, n=5).
Figure 17B:
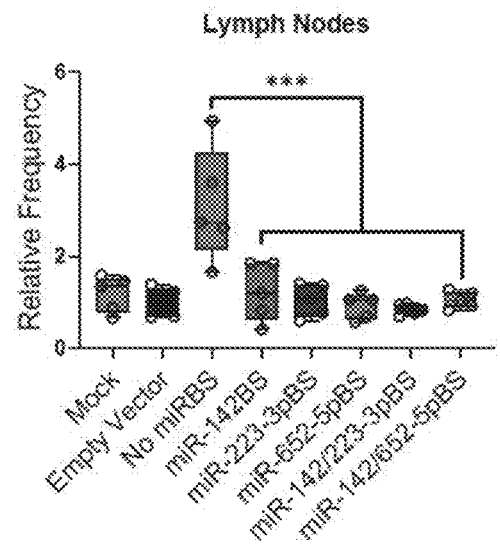

Quantification of DC populations in TAs (FIG. 17A), lymph nodes (FIG. 17B), splenocytes (FIG. 17C), and livers (FIG. 17D) were harvested four weeks after vector administration by flow cytometry and represented as box plots with means, first and third quartile boundaries, and whiskers indicating max and min values (n=5). p values were estimated by one-way ANOVA with Tukey's post hoc test. *p<0.05, p<0.01, *p<0.001

FIGS. 18A-18F show that miR-BS inclusion in rAAV vectors inhibited activation of proinflammatory cells in lymph nodes. Lymph nodes were harvested from C57BL/6 male mice two weeks post-injection with rAAV1 expression vectors. The cells isolated from lymph nodes were stained with antibodies for markers specific to macrophages (A), DCs (B), activated DCs (C), CD8 T cells (D), OVA-specific CD8 T cells (E), and CD4 T cells (F). Relative frequencies of respective immune cell populations were determined by flow cytometry and represented as box plots with means, first and third quartile boundaries, and whiskers indicating max and min values (n=5). p values were estimated by one-way ANOVA with Tukey's post hoc test. *$p<0.05$, $p<0.01$, *$p<0.001$.

FIGS. 19A-19F show that the incorporation of miR-142BS and miR-652-5pBS mediated reduction of immune cell activation markers in the spleen. Splenocytes isolated from rAAV-injected mice two weeks post-injection were immunophenotyped to determine activation levels of immune cell populations. Stained cells were analyzed on a flow cytometer and the frequencies of macrophages (FIG. 19A), DCs (FIG. 19B), activated DCs (FIG. 19C), CD8 T cells (FIG. 19D), OVA-specific CD8 T cells (FIG. 19E) and CD4 T cells (FIG. 19F) were displayed as box plots with means, first and third quartile boundaries, and whiskers indicating max and min values (n=5). p values were estimated by one-way ANOVA with Tukey's post hoc test. *$p<0.05$, $p<0.01$, *$p<0.001$.

FIGS. 20A-20F show that miR-BSs did not affect activation status of immune cell populations in circulation. PBMCs were isolated from injected mice two weeks after treatment followed by staining for macrophages (FIG. 20A), DCs (FIG. 20B), activated DCs (FIG. 20C), CD8 T cells (FIG. 20D), OVA specific CD8 T cells (FIG. 20E), and CD4 T cells (FIG. 20F). Flow cytometry data are displayed as relative frequencies were plotted as box plots with means, first and third quartile boundaries, and whiskers indicating max and min values (n=5). p values were estimated by one-way ANOVA with Tukey's post hoc test. *$p<0.05$, $p<0.01$, *$p<0.001$.

FIGS. 21A-21D show that miR-BS incorporation in rAAV vectors caused a precipitous drop in CD4 T cell activation. Cells isolated from different mouse tissues four weeks after injection of rAAV1 expression vectors were stained for CD4 T cell markers followed by analysis using flow cytometry. Relative frequencies of CD4 T cells in TA muscle (FIG. 21A), lymph nodes (FIG. 21B), splenocytes (FIG. 21C), and liver (FIG. 21D) were shown as box plots with means, first and third quartile boundaries, and whiskers indicating max and min values (n=5). p values were estimated by one-way ANOVA with Tukey's post hoc test. *$p<0.05$, $p<0.01$, *$p<0.001$.

FIGS. 22A-22F show that miR-652-5pBS and miR-142/652-5pBS-containing vectors efficiently suppressed OVA specific memory T cells. Splenocytes harvested from C57BL/6 mice 2-weeks post rAAV1 injection were stimulated with OVA (5 µg/mL) for 24 hours followed by staining with CD44 and CD62L to profile for both CD4+ and CD8+ effector memory (FIGS. 22A and 22D; CD44highCD62Lneg, TEM), central memory (FIGS. 22B and 22E; CD44highCD62L+; TCM) and naïve T cells (FIGS. 22C and 22F; CD44lowCD62L+). Analysis was done by flow cytometry and relative frequencies are plotted as box plots with means, first and third quartile boundaries, and whiskers indicating max and min values (n=5). p values were estimated by one-way ANOVA with Tukey's post hoc test. *$p<0.05$, $p<0.01$, *$p<0.001$.

Figure 23A:
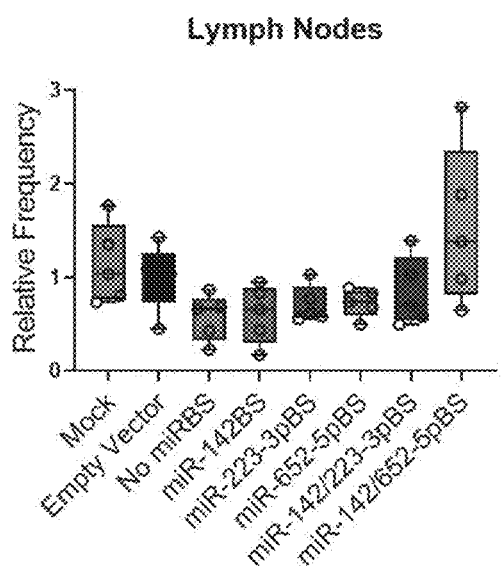
Figure 23B:
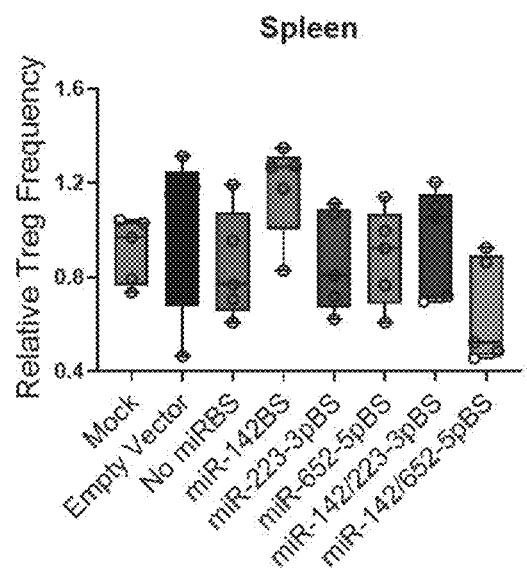

FIGS. 23A-23D show that incorporation of miR-BSs had no effect on regulatory T cell populations. C57BL/6 mice were injected with rAAV1 vectors and cells from lymph nodes and spleens were isolated two weeks after treatment. Cells were stained for the expression of Treg markers and analyzed by flow cytometry. The relative frequencies are shown as box plots with means, first and third quartile boundaries, and whiskers indicating max and min values (n=5) for lymph nodes (FIG. 23A) and spleen (FIG. 23B). The levels of IL-10 (FIG. 23C) and TGF-b (FIG. 23D) that were secreted by stimulated splenocytes four weeks after vector injection were estimated by ELISA (mean±SD, n=5).

Figure 24A:
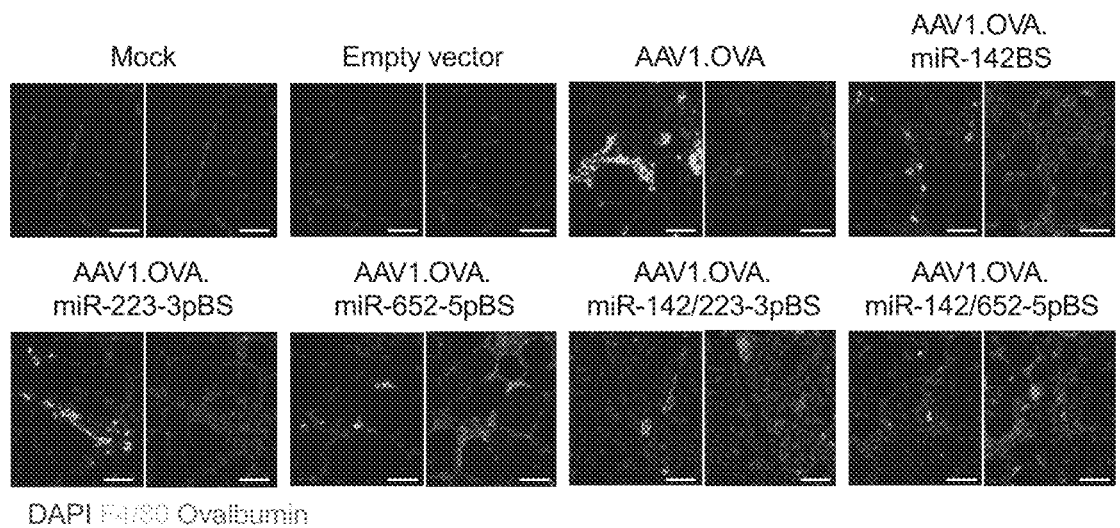
Figure 24B:
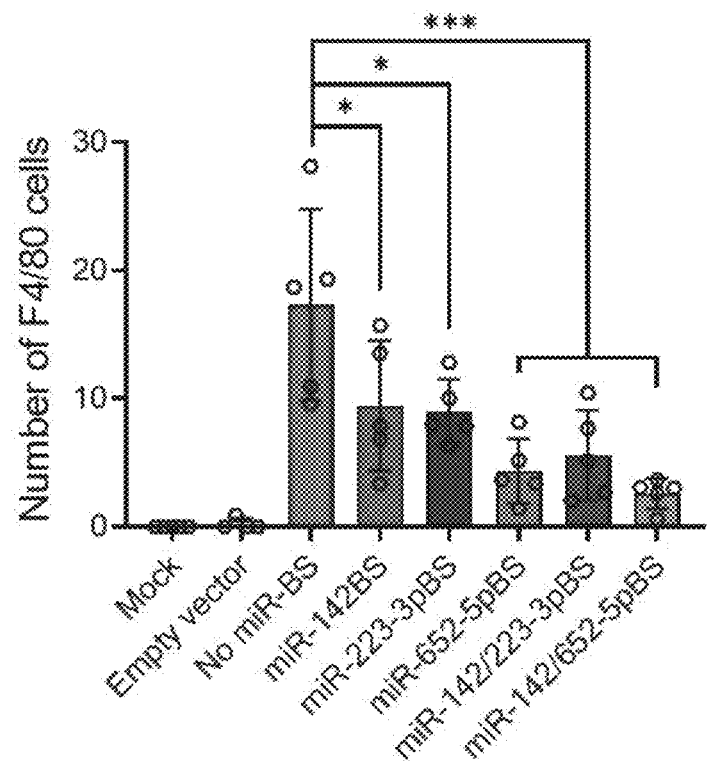

FIGS. 24A and 24B show that miR-652-5p and miR-142/652-5pBS cassettes conferred robust repression of macrophage activation and supported stable OVA transgene expression. C57BL/6 male mice, six weeks old, were i.m. injected with rAAV1.OVA vectors with or without miRBS ($1\times10^{11}$ GCs/mouse, n=5) and sacrificed two weeks after injection to harvest injected TAs. FIG. 24A shows that immunohistochemistry staining to detect macrophages and transgene expression was performed by using antibodies against F4/80 (left panels) and OVA (right panels), respectively. Images were acquired at 40× magnification (DAPI, blue; anti-F4/80, green; and anti-OVA, red). Scale bars correspond to 50 µm. FIG. 24B shows that quantification of F4/80 images in four fields at original magnification of 40× (n=5). p values were estimated by one-way ANOVA with Tukey's post hoc test. *$p<0.05$, $p<0.01$, *$p<0.001$.

DETAILED DESCRIPTION

Aspects of the disclosure relate to a recognition that immune responses can occur that are directed against therapeutic transgene products delivered by recombinant adeno-associated viruses (rAAVs), which can lead to untoward outcomes. In some cases, for example, a B cell response to a transgene product results in inhibitory antibodies, thereby impairing the treatment. Accordingly, aspects of the disclosure relate to methods of delivering a transgene to target cells of a subject in a manner that reduces or eliminates immune responses (cellular and/or humoral) produced in the subject against products of the transgene. In some embodiments, the use of recombinant AAVs to deliver transgenes is disclosed. Also described herein are transgenes engineered with combinations of different immune-related miRNA binding sites to achieve synergistic effects.

AAV is advantageous for gene therapy due to lack of pathogenicity, lower immunogenicity and ability to establish long-term transgene expression. Pre-clinical and clinical evidence has demonstrated that rAAV can mediate persistent and long-term expression of transgenes in muscle and liver tissues as "biofactories" for secreted proteins in prophylactic and therapeutic scenarios with few side effects. These include the exogenous expression of AAV vectored broadly neutralizing antibodies or modified CD4-Igs for preventing infectious diseases such as AIDS, Hepatitis C, malaria, and influenza as well as the expression of bacterially derived transgenes such those required in CRISPR-Cas approaches and those used in inducible promoters. However, a major limitation to these methods has been host immune responses towards the transgene, namely anti-drug antibody (ADA) responses.

Without wishing to be bound by any theory, antigen-specific B cell activation can result in the production of inhibitory antibodies against transgene products, thereby impairing treatment potential. In recent studies, these antiantibody ADA responses were observed in macaques. In another example, rAAV-delivered products can be blocked by transgene-specific cellular immunity or can trigger autoimmunity towards endogenous proteins. In another example, Tet (Tetracycline)-on system components are repressed by the recognition of bacterial protein antigens that are inherent to reverse tetracycline-controlled transactivators (rtTA). In another example, redosing patients with rAAV vectors can be achieved by overcoming adaptive immunity against the capsid by several means, but nonetheless can be blocked by immunity against the transgene.

A well-known cause for transgene-related immunotoxicity is the undesirable transduction of antigen presenting cells (APCs), which in turn triggers host immunity towards rAAV-expressed transgene products. Among professional APCs (e.g. dendritic cells, macrophages, and B-lymphocytes), dendritic cells (DCs) may represent the most important cell type in the host, having the broadest range of antigen presentation. Therefore, rAAV transduction of DCs can lead to the display of transgene peptide epitopes on MHC class I molecules. Such events would in turn activate cytotoxic CD8+ T lymphocytes (CTLs) to clear cells that express the exogenous protein. Undesirable transgene expression in DCs can potentially be overcome by the use of highly-specific tissue promoters. However, rAAV-compatible tissue-specific regulatory cassettes have been shown to be leaky in DCs. Therefore, alternative strategies to effectively reduce spurious expression in DCs may help to attenuate transgene-related immune responses following rAAV transduction.

In some embodiments, advantages of AAV are combined with immune-associated miRNA-regulated transgene expression to overcome immune responses against transgene products. In some embodiments, methods are provided that involve administering to the subject a recombinant Adeno-Associated Virus (rAAV) that harbors a transgene engineered to express an RNA transcript that comprises at least one immune-associated miRNA binding site (e.g., an immune-associated miRNA of Table 1). In some embodiments, to reduce immune responses against rAAV-derived transgene products, AAV vectors are provided that incorporate immune-related miRNA binding sites (BS) into the 3'UTR of the transgene. In some aspects, the miRNA binding sites are the reverse complement of specific miRNAs expressed in immune cells, as disclosed herein. In some aspects, the miRNA binding sites function to reduce the presentation of transgenes through the antigen presentation pathways.

In some embodiments, presence of binding sites of one or more immune-associated miRNAs results in a lower immune response in a subject against a product of the RNA transcript compared with a control. A control can be a predetermined level indicative of an undesirable immune response. In some embodiments, a control is the level of an immune response in a control subject that has been administered a control rAAV comprising a transgene engineered to express a control RNA transcript encoding the product, wherein the control RNA transcript does not comprise immune-associated miRNA binding sites. For example, the lower immune response may be i) a lower level of antibodies specific for the product of the transgene, ii) a lower level of T-lymphocytes specific for the product, or iii) a lower level of antigen presenting cells in the subject that display antigens of the product through MHC class I molecules. The immune response may be less than 10%, less than 20%, less than 30%, less than 40%, less than 50%, less than 60%, less than 70%, less than 80%, or less than 90% of the control level, for example. It should be appreciated that the immune response may be sufficiently low so as to permit the product of the transgene to perform its intended function. It should also be appreciated that immune response may be sufficiently low so as to permit the product of the transgene to perform its desired therapeutic effect in the subject.

In some embodiments, the reduction in immune response is at least 10%, at least 20%, at least 30%, at least 40%, at least 50%, at least 60%, at least 70%, at least 80%, at least 90% reduction in the level of antigen presentation cells that display antigens of the product through MHC class I molecules compared with the control.

In some embodiments, the reduction in immune response is at least 10%, at least 20%, at least 30%, at least 40%, at least 50%, at least 60%, at least 70%, at least 80%, at least 90% reduction in the level of neutralizing antibodies compared with the control. In some embodiments, the neutralizing antibodies bind specifically to the product of the RNA transcript.

In some embodiments, the reduction in immune response is at least 10%, at least 20%, at least 30%, at least 40%, at least 50%, at least 60%, at least 70%, at least 80%, at least 90% reduction in the level of T lymphocytes compared with the control. In some embodiments, the T lymphocytes bind specifically to the product of the RNA transcript. In some embodiments, the reduction in immune response is at least 10%, at least 20%, at least 30%, at least 40%, at least 50%, at least 60%, at least 70%, at least 80%, at least 90% reduction in the level of cytotoxic T lymphocytes compared with the control. In some embodiments, the cytotoxic T lymphocytes bind specifically to the product of the RNA transcript. In some embodiments, the reduction in immune response is at least 10%, at least 20%, at least 30%, at least 40%, at least 50%, at least 60%, at least 70%, at least 80%, at least 90% reduction in the level of mature dendritic cells compared with the control. In some embodiments, the mature dendritic cells bind specifically to the product of the RNA transcript. In some embodiments, the reduction in immune response is at least 10%, at least 20%, at least 30%, at least 40%, at least 50%, at least 60%, at least 70%, at least 80%, at least 90% reduction in the level of macrophages compared with the control. In some embodiments, the macrophages bind specifically to the product of the RNA transcript.

In some embodiments, the reduction in immune response is at least 10%, at least 20%, at least 30%, at least 40%, at least 50%, at least 60%, at least 70%, at least 80%, at least 90% reduction in the level of any immune cells that bind specifically to the product of the RNA transcript and kill cells transduced by the rAAV.

MicroRNAs (miRNAs) are small, non-coding RNAs which regulate cellular gene expression by post-transcriptional silencing. When miRNAs are partially complementary to the target mRNA sequences, they typically reduce target mRNA stability and inhibit translation. In contrast, when miRNAs are nearly perfectly complementary to their mRNA targets, they cleave the mRNA, triggering its wholesale destruction via Ago2 cleavage. A miRNA may be a 5p (e.g., 5' arm) miRNA or a 3p (e.g., 3' arm) miRNA. miRNA-mediated detargeting has been shown to assist tissue-specific expression post-transcriptionally by culling spuriously transcribed transgenes that may accumulate in off-target cells. miRNAs have distinct expression profiles in different tissues and cell types, which differentially regulate transcriptional profiles of cellular genes and cellular functions, including APCs and immune activation. Many miRNAs have been reported to be involved in the regulation and development of macrophages, DCs, and B-cells. Therefore, methods provided herein employ immune-related miRNAs (e.g., APC-specific miRNAs) to silence transgene expression in immune cells (e.g., APCs). Accordingly, methods provided herein reduce immune responses to transgene products.

As used herein an "immune-associated miRNA" is a miRNA preferentially expressed in a cell of the immune system, such as an antigen presenting cell (APC). In some embodiments, an immune-associated miRNA is a miRNA expressed in immune cells that exhibits at least a 2-fold, 3-fold, 4-fold, 5-fold, 6-fold, 7-fold, 8-fold, 9-fold, 10-fold higher level of expression in an immune cell compared with a non-immune cell (e.g., a control cell, such as a HeLa cell, HEK293 cell, mesenchymal cell, etc.). In some embodiments, the cell of the immune system (immune cell) in which the immune-associated miRNA is expressed is a B cell, T cell, Killer T cell, Helper T cell, γδT cell, dendritic cell, macrophage, monocyte, vascular endothelial cell, MF or other immune cells. In some embodiments, the cell of the immune system is a B cell expressing one or more of the following markers: B220, BLAST-2 (EBVCS), Bu-1, CD19, CD20 (L26), CD22, CD24, CD27, CD57, CD72, CD79a, CD79b, CD86, chB6, D8/17, FMC7, L26, M17, MUM-1, Pax-5 (BSAP), and PC47H. In some embodiments, the cell of the immune system is a T cell expressing one or more of the following markers: ART2, CD1a, CD1d, CD11b (Mac-1), CD134 (OX40), CD150, CD2, CD25 (interleukin 2 receptor alpha), CD3, CD38, CD4, CD45RO, CD5, CD7, CD72, CD8, CRTAM, FOXP3, FT2, GPCA, HLA-DR, HML-1, HT23A, Leu-22, Ly-2, Ly-m22, MICG, MRC OX 8, MRC OX-22, OX40, PD-1 (Programmed death-1), RT6, TCR (T cell receptor), Thy-1 (CD90), and TSA-2 (Thymic shared Ag-2). In some embodiments, the immune-associated miRNA is selected from: miR-106, miR-125a, miR-125b, miR-126a, miR-142, miR-146a, miR-15, miR-150, miR-155, miR-16, miR-17, miR-18, miR-181a, miR-19a, miR-19b, miR-20, miR-21a, miR-223, miR-24-3p, miR-29a, miR-29b, miR-29c, miR-302a-3p, miR-30b, miR-33-5p, miR-34a, miR-424, miR-652-3p, miR-652-5p, miR-9-3p, miR-9-5p, miR-92a, and miR-99b-5p (SEQ ID NO: 1-33). In some embodiments, the immune-associated miRNA is in Table 1.

In some embodiments, transgenes may be engineered to express a protein of interest, e.g., a therapeutic protein. Transcripts expressing such proteins may also be engineered to contain one or more immune-related miRNAs. In this way, the transcript, if expressed in immune cells, may be degraded via miRNAs expressed in the immune cells. A "miRNA inhibitor" is an agent that blocks miRNA function, expression and/or processing. For instance, these molecules include but are not limited to microRNA specific antisense, microRNA sponges, tough decoy RNAs (TuD RNAs) and microRNA oligonucleotides (double-stranded, hairpin, short oligonucleotides) that inhibit miRNA interaction with a Drosha complex. MicroRNA inhibitors can be expressed in cells from a transgene of a rAAV vector, as discussed above. MicroRNA sponges specifically inhibit miRNAs through a complementary heptameric seed sequence (Ebert, M.S. Nature Methods, Epub Aug. 12, 2007). In some embodiments, an entire family of miRNAs can be silenced using a single sponge sequence. TuD RNAs achieve efficient and long-term-suppression of specific miRNAs in mammalian cells (See, e.g., Takeshi Haraguchi, et al., Nucleic Acids Research, 2009, Vol. 37, No. 6 e43, the contents of which relating to TuD RNAs are incorporated herein by reference). Other methods for silencing miRNA function (derepression of miRNA targets) in cells will be apparent to one of ordinary skill in the art. In the present disclosure, the incorporated miRNA binding sites and/or expression of miRNA inhibitors may disturb the normal expression profiles the corresponding miRNAs.

As disclosed herein, the miRNAs are expressed and/or enriched in specific immune cells. For example, in some embodiments, miR-106 is enriched in monocytes. In another example, miR-142 is enriched in dendritic cells. In another example, miR-223 is enriched in myeloid cells. In another example, miR-652 (e.g. miR-652-5p) is enriched in dendritic cells.

In some embodiments, the miRNA is at least 5%, at least 10%, at least 15%, at least 20%, at least 25%, at least 30%, at least 35%, at least 40%, at least 45%, at least 50%, at least 55%, at least 60%, at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% identical, or 100% identical, including all values in between, to miR-33-5p. In some embodiments, the at least one immune-associated miRNA binding site is miR-33-5pBS.

In some embodiments, the sequence of the immune-associated miRNA binding site ise at least 5%, at least 10%, at least 15%, at least 20%, at least 25%, at least 30%, at least 35%, at least 40%, at least 45%, at least 50%, at least 55%, at least 60%, at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% identical, or 100% identical, including all values in between, to the miR-33-5pBS.

In some embodiments, the sequence of the immune-associated miRNA binding site is at least 5%, at least 10%, at least 15%, at least 20%, at least 25%, at least 30%, at least 35%, at least 40%, at least 45%, at least 50%, at least 55%, at least 60%, at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% identical, or 100% identical, including all values in between, to SEQ ID NO: 25. In some embodiments, the length of the miRNA binding site is at least 5%, at least 10%, at least 15%, at least 20%, at least 25%, at least 30%, at least 35%, at least 40%, at least 45%, at least 50%, at least 55%, at least 60%, at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% identical, or 100% identical, including all values in between, to miR-33-5pBS.

In some embodiments, the miRNA is at least 5%, at least 10%, at least 15%, at least 20%, at least 25%, at least 30%, at least 35%, at least 40%, at least 45%, at least 50%, at least 55%, at least 60%, at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% identical, or 100% identical, including all values in between, to miR-223-3p. In some embodiments, the at least one immune-associated miRNA binding site is miR-223-3pBS.

In some embodiments, sequences of the immune-associated miRNA binding site is at least 5%, at least 10%, at least 15%, at least 20%, at least 25%, at least 30%, at least 35%, at least 40%, at least 45%, at least 50%, at least 55%, at least 60%, at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% identical, or 100% identical, including all values in between, to miR-223-3pBS.

In some embodiments, sequences of the immune-associated miRNA binding site is at least 5%, at least 10%, at least 15%, at least 20%, at least 25%, at least 30%, at least 35%, at least 40%, at least 45%, at least 50%, at least 55%, at least 60%, at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% identical, or 100% identical, including all values in between, to SEQ ID NO: 38.

In some embodiments, the length of the miRNA binding site is at least 5%, at least 10%, at least 15%, at least 20%, at least 25%, at least 30%, at least 35%, at least 40%, at least 45%, at least 50%, at least 55%, at least 60%, at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% identical, or 100% identical, including all values in between, to miR-223-3pBS.

In some embodiments, the miRNA is at least 5%, at least 10%, at least 15%, at least 20%, at least 25%, at least 30%, at least 35%, at least 40%, at least 45%, at least 50%, at least 55%, at least 60%, at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% identical, or 100% identical, including all values in between, to miR-652-5p. In some embodiments, the at least one immune-associated miRNA binding site is miR-652-5pBS.

In some embodiments, sequences of the immune-associated miRNA binding site is at least 5%, at least 10%, at least 15%, at least 20%, at least 25%, at least 30%, at least 35%, at least 40%, at least 45%, at least 50%, at least 55%, at least 60%, at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% identical, or 100% identical, including all values in between, to miR-652-5pBS.

In some embodiments, sequences of the immune-associated miRNA binding site is at least 5%, at least 10%, at least 15%, at least 20%, at least 25%, at least 30%, at least 35%, at least 40%, at least 45%, at least 50%, at least 55%, at least 60%, at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% identical, or 100% identical, including all values in between, to SEQ ID NO: 39.

In some embodiments, the length of the miRNA binding site is at least 5%, at least 10%, at least 15%, at least 20%, at least 25%, at least 30%, at least 35%, at least 40%, at least 45%, at least 50%, at least 55%, at least 60%, at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% identical, or 100% identical, including all values in between, to miR-652-5pBS.

In some embodiments, the miRNA is at least 5%, at least 10%, at least 15%, at least 20%, at least 25%, at least 30%, at least 35%, at least 40%, at least 45%, at least 50%, at least 55%, at least 60%, at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% identical, or 100% identical, including all values in between, to miR-142BS. In some embodiments, the at least one immune-associated miRNA binding site is miR142BS.

In some embodiments, sequences of the immune-associated miRNA binding site is at least 5%, at least 10%, at least 15%, at least 20%, at least 25%, at least 30%, at least 35%, at least 40%, at least 45%, at least 50%, at least 55%, at least 60%, at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% identical, or 100% identical, including all values in between, to miR-142BS. In some embodiments, sequences of the immune-associated miRNA binding site is at least 5%, at least 10%, at least 15%, at least 20%, at least 25%, at least 30%, at least 35%, at least 40%, at least 45%, at least 50%, at least 55%, at least 60%, at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% identical, or 100% identical, including all values in between, to SEQ ID NO: 5.

In some embodiments, the length of the miRNA binding site is at least 5%, at least 10%, at least 15%, at least 20%, at least 25%, at least 30%, at least 35%, at least 40%, at least 45%, at least 50%, at least 55%, at least 60%, at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% identical, or 100% identical, including all values in between, to miR-142BS.

In some embodiments, the miRNA shares at least 5%, at least 10%, at least 15%, at least 20%, at least 25%, at least 30%, at least 35%, at least 40%, at least 45%, at least 50%, at least 55%, at least 60%, at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%, including all values in between, with any miRNA target listed in Table 1. In some embodiments, the at least one immune-associated miRNA binding site can be any miRNA binding sites listed in Table 1.

In some embodiments, sequences of the immune-associated miRNA binding site share at least 5%, at least 10%, at least 15%, at least 20%, at least 25%, at least 30%, at least 35%, at least 40%, at least 45%, at least 50%, at least 55%, at least 60%, at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% identical, or is 100% identical, including all values in between, to any miRNA binding sites listed in Table 1.

In some embodiments, sequences of the immune-associated miRNA binding site share at least 5%, at least 10%, at least 15%, at least 20%, at least 25%, at least 30%, at least 35%, at least 40%, at least 45%, at least 50%, at least 55%, at least 60%, at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% identical, or is 100% identical, including all values in between, to any one of SEQ ID NOs: 1-4 and 6-45.

In some embodiments, the length of the miRNA binding site is at least 5%, at least 10%, at least 15%, at least 20%, at least 25%, at least 30%, at least 35%, at least 40%, at least 45%, at least 50%, at least 55%, at least 60%, at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% identical, or is 100% identical, including all values in between, to any one of the miRNA binding sites listed in Table 1.

As disclosed herein, "identity" of sequences refers to the measurement or calculation of the percent of identical matches between two or more sequences with gap alignments addressed by a mathematical model, algorithm, or computer program that is known to one of ordinary skill in the art. The percent identity of two sequences (e.g., nucleic acid or amino acid sequences) may, for example, be determined using Basic Local Alignment Search Tool (BLAST®) such as NBLAST® and XBLAST® programs (version 2.0). Alignment technique such as Clustal Omega may be used for multiple sequence alignments. Other algorithms or alignment methods may include but are not limited to the Smith-Waterman algorithm, the Needleman-Wunsch algorithm, or Fast Optimal Global Sequence Alignment Algorithm (FOGSAA).

In some embodiments, the immune-associated miRNA binding site is a combination of at least two different miRNA binding sites. In some embodiments, the immune-associated miRNA binding site is a combination of miR-142BS and miR-652BS and is encoded by a sequence corresponding to SEQ ID NO: 40. In some embodiments, the immune-associated miRNA binding site is a combination of miR-142BS and miR-223-3pBS and is encoded by a sequence corresponding to SEQ ID NO: 41. In some embodiments, the immune-associated miRNA binding site is a combination of miR-142BS and miR-33-5pBS.

In some embodiments, the immune-associated miRNA binding site can be a combination of any miRNAs listed in Table 1.

In some embodiments, the combination of at least two different miRNA binding sites (e.g., a combination of miR-142BS and miR-652BS) may be used for multi-tissue detargeting. Multi-tissue detargeting may allow the expression profiles of multiple miRNAs to be exploited concomitantly to reshape rAAV tropism and therefore, to achieve tissue specific expression.

In some embodiments, the transgene product is a protein comprising a plurality of Glycine-Alanine repeats (e.g., 2 to 10, 2 to 20, 5 to 10, 5 to 20, 10 to 20, 20 to 50, 10 to 100, 100 to 200 GA repeats) that inhibit proteasomal processing in cells thereby inhibiting antigen presentation by MHC class I molecules.

Recombinant AAV Vectors

"Recombinant AAV (rAAV) vectors" of the disclosure typically comprise a transgene and its regulatory sequences, and 5' and 3' AAV inverted terminal repeats (ITRs). It is this recombinant AAV vector which is packaged into a capsid protein and delivered to a selected target cell. In some embodiments, a transgene comprises a nucleic acid sequence, heterologous to a vector sequence, which encodes a polypeptide, protein, functional RNA molecule (e.g., miRNA sponge) or other gene product of interest. The nucleic acid coding sequence is operatively linked to regulatory components in a manner that permits transgene transcription, translation, and/or expression in a cell of a target tissue.

In some embodiments, nucleic acids comprise a transgene engineered to express an RNA transcript that comprises binding sites for at least one, at least two or at least three immune-associated miRNAs. In some embodiments, the RNA transcript is a messenger RNA. In some embodiments, at least one of the miRNA binding sites is present in the 3'-UTR of the messenger RNA. In some embodiments, each of the miRNA binding sites is present in the 3'-UTR of the messenger RNA. In some embodiments, at least one of the miRNA binding sites is present in the 5'-UTR of the messenger RNA. In some embodiments, each of the miRNA binding sites is present in the 5'-UTR of the messenger RNA. In some embodiments, at least one of the miRNA binding sites is present in the intron of the messenger RNA. In some embodiments, each of the miRNA binding sites is present in the intron of the messenger RNA.

In some embodiments, the transgene is flanked by inverted terminal repeat sequences of an adeno-associated virus. In some embodiments, the RNA transcript comprises binding sites for 1, 2, 3, 4, 5, 6, 7, 8, 9, 10, 11, 12, 13, 14, 15, 16, 17, 18, 19, 20, 21, 22, 23, 24, 25 or more immune-associated miRNAs. In some embodiments, the RNA transcript comprises binding sites for a number of immune-associated miRNAs in a range of 1 to 5, 1 to 10, 2 to 5, 2 to 10, 2 to 15, 2 to 20, or 5 to 25 immune-associated miRNAs, which may or may not be selected from Table 1. In some embodiments, the transgene does not contain a binding site for miR-142. In some embodiments, an immune-associated miRNA binding site is in an exon, intron, intron-exon junction, 5' UTR, or 3' UTR of the RNA transcript. In some embodiments, an immune-associated miRNA binding site is in a non-protein coding region. In some embodiments, an immune-associated miRNA binding site is in any suitable region of the RNA transcript.

The AAV sequences of the vector typically comprise the cis-acting 5' and 3' inverted terminal repeat sequences (See, e.g., B. J. Carter, in "Handbook of Parvoviruses", ed., P. Tijsser, CRC Press, pp. 155 168 (1990)). The ITR sequences are about 145 bp in length. Preferably, substantially the entire sequences encoding the ITRs are used in the molecule, although some degree of minor modification of these sequences is permissible. The ability to modify these ITR sequences is within the skill of the art. (See, e.g., texts such as Sambrook et al, "Molecular Cloning. A Laboratory Manual", 2d ed., Cold Spring Harbor Laboratory, New York (1989); and K. Fisher et al., J Virol., 70:520 532 (1996)). An example of such a molecule employed in the present disclosure is a "cis-acting" plasmid containing the transgene, in which the selected transgene sequence and associated regulatory elements are flanked by the 5' and 3' AAV ITR sequences. The AAV ITR sequences may be obtained from any known AAV, including presently identified mammalian AAV types.

In addition to the major elements identified above for the recombinant AAV vector, the vector also includes conventional control elements necessary which are operably linked to the transgene in a manner which permits its transcription, translation and/or expression in a cell transfected with the plasmid vector or infected with the virus produced by the disclosure. As used herein, "operably linked" sequences include both expression control sequences that are contiguous with the gene of interest and expression control sequences that act in trans or at a distance to control the gene of interest.

Expression control sequences include appropriate transcription initiation, termination, promoter and enhancer sequences; efficient RNA processing signals such as splicing and polyadenylation (polyA) signals; sequences that stabilize cytoplasmic mRNA; sequences that enhance translation efficiency (e.g., Kozak consensus sequence); sequences that enhance protein stability; and when desired, sequences that enhance secretion of the encoded product. A great number of expression control sequences, including promoters which are native, constitutive, inducible and/or tissue-specific, are known in the art and may be utilized.

As used herein, a nucleic acid sequence (e.g., coding sequence) and regulatory sequences are said to be "operably" linked when they are covalently linked in such a way as to place the expression or transcription of the nucleic acid sequence under the influence or control of the regulatory sequences. If it is desired that the nucleic acid sequences be translated into a functional protein, two DNA sequences are said to be operably linked if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably linked to a nucleic acid sequence if the promoter region were capable of effecting transcription of that DNA sequence such that the resulting transcript might be translated into the desired protein or polypeptide. Similarly, two or more coding regions are operably linked when they are linked in such a way that their transcription from a common promoter results in the expression of two or more proteins having been translated in frame. In some embodiments, operably linked coding sequences yield a fusion protein. In some embodiments, operably linked coding sequences yield a functional RNA (e.g., shRNA, miRNA, miRNA inhibitor).

For nucleic acids encoding proteins, a polyadenylation sequence generally is inserted following the transgene sequences and before the 3' AAV ITR sequence. A rAAV vector useful in the present disclosure may also contain an intron, desirably located between the promoter/enhancer sequence and the transgene. One possible intron sequence is derived from SV-40 and is referred to as the SV-40 T intron sequence. Another vector element that may be used is an internal ribosome entry site (IRES). An IRES sequence is used to produce more than one polypeptide from a single gene transcript. An IRES sequence would be used to produce a protein that contain more than one polypeptide chains. Selection of these and other common vector elements are conventional and many such sequences are available The precise nature of the regulatory sequences needed for gene expression in host cells may vary between species, tissues or cell types, but shall in general include, as necessary, 5' non-transcribed and 5' non-translated sequences involved with the initiation of transcription and translation respectively, such as a TATA box, capping sequence, CAAT sequence, enhancer elements, and the like. Especially, such 5' non-transcribed regulatory sequences will include a promoter region that includes a promoter sequence for transcriptional control of the operably joined gene. Regulatory sequences may also include enhancer sequences or upstream activator sequences as desired. The vectors of the disclosure may optionally include 5' leader or signal sequences. The choice and design of an appropriate vector is within the ability and discretion of one of ordinary skill in the art.

Examples of constitutive promoters include, without limitation, THE CB6 promoter, the retroviral Rous sarcoma virus (RSV) LTR promoter (optionally with the RSV enhancer), the cytomegalovirus (CMV) promoter (optionally with the CMV enhancer) [see, e.g., Boshart et al, Cell, 41:521-530 (1985)], the SV40 promoter, the dihydrofolate reductase promoter, the β-actin promoter, the phosphoglycerol kinase (PGK) promoter, and the EF1α promoter [Invitrogen].

Inducible promoters allow regulation of gene expression and can be regulated by exogenously supplied compounds, environmental factors such as temperature, or the presence of a specific physiological state, e.g., acute phase, a particular differentiation state of the cell, or in replicating cells only. Inducible promoters and inducible systems are available from a variety of commercial sources, including, without limitation, Invitrogen, Clontech and Ariad. Many other systems have been described and can be readily selected by one of skill in the art. Examples of inducible promoters regulated by exogenously supplied promoters include the zinc-inducible sheep metallothionine (MT) promoter, the dexamethasone (Dex)-inducible mouse mammary tumor virus (MMTV) promoter, the T7 polymerase promoter system (WO 98/10088); the ecdysone insect promoter (No et al, Proc. Natl. Acad. Sci. USA, 93:3346-3351 (1996)), the tetracycline-repressible system (Gossen et al, Proc. Natl. Acad. Sci. USA, 89:5547-5551 (1992)), the tetracycline-inducible system (Gossen et al, Science, 268:1766-1769 (1995), see also Harvey et al, Curr. Opin. Chem. Biol., 2:512-518 (1998)), the RU486-inducible system (Wang et al, Nat. Biotech., 15:239-243 (1997) and Wang et al, Gene Ther., 4:432-441 (1997)) and the rapamycin-inducible system (Magari et al, J. Clin. Invest., 100:2865-2872 (1997)). Still other types of inducible promoters which may be useful in this context are those which are regulated by a specific physiological state, e.g., temperature, acute phase, a particular differentiation state of the cell, or in replicating cells only.

In another embodiment, the native promoter for the transgene will be used. The native promoter may be used when it is desired that expression of the transgene should mimic the native expression. The native promoter may be used when expression of the transgene must be regulated temporally or developmentally, or in a tissue-specific manner, or in response to specific transcriptional stimuli. In a further embodiment, other native expression control elements, such as enhancer elements, polyadenylation sites or Kozak consensus sequences may also be used to mimic the native expression.

In some embodiments, the regulatory sequences impart tissue-specific gene expression capabilities. In some cases, the tissue-specific regulatory sequences bind tissue-specific transcription factors that induce transcription in a tissue specific manner. Such tissue-specific regulatory sequences (e.g., promoters, enhancers, etc.) are well known in the art. Exemplary tissue-specific regulatory sequences include, but are not limited to the following tissue specific promoters: a liver-specific thyroxin binding globulin (TBG) promoter, an insulin promoter, a glucagon promoter, a somatostatin promoter, a pancreatic polypeptide (PPY) promoter, a synapsin-1 (Syn) promoter, a creatine kinase (MCK) promoter, a mammalian desmin (DES) promoter, a α-myosin heavy chain (a-MHC) promoter, or a cardiac Troponin T (cTnT) promoter. Other exemplary promoters include Beta-actin promoter, hepatitis B virus core promoter, Sandig et al., Gene Ther., 3:1002-9 (1996); alpha-fetoprotein (AFP) promoter, Arbuthnot et al., Hum. Gene Ther., 7:1503-14 (1996)), bone osteocalcin promoter (Stein et al., Mol. Biol. Rep., 24:185-96 (1997)); bone sialoprotein promoter (Chen et al., J. Bone Miner. Res., 11:654-64 (1996)), CD2 promoter (, Hansal et al., J. Immunol., 161:1063-8 (1998); immunoglobulin heavy chain promoter; T cell receptor α-chain promoter, neuronal such as neuron-specific enolase (NSE) promoter (Andersen et al., Cell. Mol. Neurobiol., 13:503-15 (1993)), neurofilament light-chain gene promoter (Piccioli et al., Proc. Natl. Acad. Sci. USA, 88:5611-5 (1991)), and the neuron-specific vgf gene promoter (Piccioli et al., Neuron, 15:373-84 (1995)), among others which will be apparent to the skilled artisan. In some embodiments, the promoter is the muscle specific promoter Desmin460 or the truncated muscle creatine kinase (tMCK) promoter.

Recombinant AAVs

AAVs produced using recombinant methods are referred to herein as "recombinant AAVs". Recombinant AAVs (rAAVs) may have tissue-specific targeting capabilities, such that a transgene of the rAAV will target specifically to one or more predetermined tissue(s). The AAV capsid is an important element in determining these tissue-specific targeting capabilities. Thus, an rAAV having a capsid appropriate for the tissue being targeted can be selected. Methods for obtaining recombinant AAVs having a desired capsid protein are well known in the art. (See, for example, US 2003/0138772), the contents of which are incorporated herein by reference in their entirety). Typically the methods involve culturing a host cell which contains a nucleic acid sequence encoding an AAV capsid protein or fragment thereof; a functional rep gene; a recombinant AAV vector composed of, AAV inverted terminal repeats (ITRs) and a transgene; and sufficient helper functions to permit packaging of the recombinant AAV vector into the AAV capsid proteins. In some embodiments the rAAV comprises a capsid protein of a serotype selected from: AAV1, AAV2, AAV3, AAV4, AAV5, AAV6, AAV7, AAV8, AAV9, AAV10, AAV11, AAV12, AAV.rh.10 and variants of any one of them. In some embodiments, the rAAV comprises a capsid protein disclosed in United States Patent Application Publication Number US 2012/0137379, entitled, "NOVEL AAV'S AND USES THEREOF," which was published on May 31, 2012, the contents of which are incorporated herein by reference in their entirety. In some embodiments, the capsid protein is modified to contain Gly-Ala repeats of Epstein-Barr virus Nuclear antigen that reduce proteasomal processing of the capsid protein in cells and capsid specific immune responses. In some embodiments, the capsid protein is modified to contain up to 2, up to 3, up to 4, up to 5, up to 10, up to 20, or up to 50 Gly-Ala repeats that reduce proteasomal processing of the capsid protein in cells and capsid specific immune responses.

The components to be cultured in the host cell to package a rAAV vector in an AAV capsid may be provided to the host cell in trans. Alternatively, any one or more of the required components (e.g., recombinant AAV vector, rep sequences, cap sequences, and/or helper functions) may be provided by a stable host cell which has been engineered to contain one or more of the required components using methods known to those of skill in the art. Most suitably, such a stable host cell will contain the required component(s) under the control of an inducible promoter. However, the required component(s) may be under the control of a constitutive promoter. Examples of suitable inducible and constitutive promoters are provided herein, in the discussion of regulatory elements suitable for use with the transgene. In still another alternative, a selected stable host cell may contain selected component(s) under the control of a constitutive promoter and other selected component(s) under the control of one or more inducible promoters. For example, a stable host cell may be generated which is derived from 293 cells (which contain E1 helper functions under the control of a constitutive promoter), but which contain the rep and/or cap proteins under the control of inducible promoters. Still other stable host cells may be generated by one of skill in the art.

The recombinant AAV vector, rep sequences, cap sequences, and helper functions involved in producing the rAAV of the disclosure may be delivered to the packaging host cell using any appropriate genetic element (vector). The selected genetic element may be delivered by any suitable method, including those described herein. The methods used to construct any embodiment of this disclosure are known to those with skill in nucleic acid manipulation and include genetic engineering, recombinant engineering, and synthetic techniques. See, e.g., Sambrook et al, Molecular Cloning: A Laboratory Manual, Cold Spring Harbor Press, Cold Spring Harbor, N.Y. Similarly, methods of generating rAAV virions are well known and the selection of a suitable method is not a limitation on the present disclosure. See, e.g., K. Fisher et al, J. Virol., 70:520-532 (1993) and U.S. Pat. No. 5,478,745.

In some embodiments, recombinant AAVs may be produced using the triple transfection method (described in detail in U.S. Pat. No. 6,001,650). Typically, the recombinant AAVs are produced by transfecting a host cell with an recombinant AAV vector (comprising a transgene) to be packaged into AAV particles, an AAV helper function vector, and an accessory function vector. An AAV helper function vector encodes the "AAV helper function" sequences (e.g., rep and cap), which function in trans for productive AAV replication and encapsidation. Preferably, the AAV helper function vector supports efficient AAV vector production without generating any detectable wild-type AAV virions (e.g., AAV virions containing functional rep and cap genes). Non-limiting examples of vectors suitable for use with the present disclosure include pHLP19, described in U.S. Pat. No. 6,001,650 and pRep6cap6 vector, described in U.S. Pat. No. 6,156,303, the entirety of both incorporated by reference herein. The accessory function vector encodes nucleotide sequences for non-AAV derived viral and/or cellular functions upon which AAV is dependent for replication (e.g., "accessory functions"). The accessory functions include those functions required for AAV replication, including, without limitation, those moieties involved in activation of AAV gene transcription, stage specific AAV mRNA splicing, AAV DNA replication, synthesis of cap expression products, and AAV capsid assembly. Viral-based accessory functions can be derived from any of the known helper viruses such as adenovirus, herpesvirus (other than herpes simplex virus type-1), and vaccinia virus.

In some aspects, the disclosure provides transfected host cells. The term "transfection" is used to refer to the uptake of foreign DNA by a cell, and a cell has been "transfected" when exogenous DNA has been introduced inside the cell membrane. A number of transfection techniques are generally known in the art. See, e.g., Graham et al. (1973) Virology, 52:456, Sambrook et al. (1989) Molecular Cloning, a laboratory manual, Cold Spring Harbor Laboratories, New York, Davis et al. (1986) Basic Methods in Molecular Biology, Elsevier, and Chu et al. (1981) Gene 13:197. Such techniques can be used to introduce one or more exogenous nucleic acids, such as a nucleotide integration vector and other nucleic acid molecules, into suitable host cells.

A "host cell" refers to any cell that harbors, or is capable of harboring, a substance of interest. In some embodiments, suitable host cells include, but are not limited to yeast cells, bacterial cells, algal cells, plant cells, fungal cells, insect cells, and animal cells, including mammalian cells. In one illustrative embodiment, suitable host cells include *E. coli* (e.g., Shuffle™ competent *E. coli* available from New England BioLabs in Ipswich, Mass. In some embodiments, the host cell is a prokaryotic cell. Suitable prokaryotic cells, for example, include gram positive, gram negative, and gram-variable bacterial cells. The host cell may be a species of, but not limited to: *Agrobacterium, Alicyclobacillus, Anabaena, Anacystis, Acinetobacter, Acidothermus, Arthrobacter, Azobacter, Bacillus, Bifidobacterium, Brevibacterium, Butyrivibrio, Buchnera, Campestris, Camplyobacter, Clostridium, Corynebacterium, Chromatium, Coprococcus, Escherichia, Enterococcus, Enterobacter, Erwinia, Fusobacterium, Faecalibacterium, Francisella, Flavobacterium, Geobacillus, Haemophilus, Helicobacter, Klebsiella, Lactobacillus, Lactococcus, Ilyobacter, Micrococcus, Microbacterium, Mesorhizobium, Methylobacterium, Methylobacterium, Mycobacterium, Neisseria, Pantoea, Pseudomonas, Prochlorococcus, Rhodobacter, Rhodopseudomonas, Rhodopseudomonas, Roseburia, Rhodospirillum, Rhodococcus, Scenedesmus, Streptomyces, Streptococcus, Synecoccus, Saccharomonospora, Saccharopolyspora, Staphylococcus, Serratia, Salmonella, Shigella, Thermoanaerobacterium, Tropheryma, Tularensis, Temecula, Thermosynechococcus, Thermococcus, Ureaplasma, Xanthomonas, Xylella, Yersinia*, and *Zymomonas*. Often a host cell is a mammalian cell. In some embodiments, suitable host cells can be any type of host cell that is suitable for AAV production as disclosed herein.

A host cell may be used as a recipient of an AAV helper construct, an AAV minigene plasmid, an accessory function vector, or other transfer DNA associated with the production of recombinant AAVs. The term includes the progeny of the original cell which has been transfected. Thus, a "host cell" as used herein may refer to a cell which has been transfected with an exogenous DNA sequence. It is understood that the progeny of a single parental cell may not necessarily be completely identical in morphology or in genomic or total DNA complement as the original parent, due to natural, accidental, or deliberate mutation.

As used herein, the term "cell line" refers to a population of cells capable of continuous or prolonged growth and division in vitro. Often, cell lines are clonal populations derived from a single progenitor cell. It is further known in the art that spontaneous or induced changes can occur in karyotype during storage or transfer of such clonal populations. Therefore, cells derived from the cell line referred to may not be precisely identical to the ancestral cells or cultures, and the cell line referred to includes such variants.

As used herein, the terms "recombinant cell" refers to a cell into which an exogenous DNA segment, such as DNA segment that leads to the transcription of a biologically-active polypeptide or production of a biologically active nucleic acid such as an RNA, has been introduced.

As used herein, the term "vector" includes any genetic element, such as a plasmid, phage, transposon, cosmid, chromosome, artificial chromosome, virus, virion, etc., which is capable of replication when associated with the proper control elements and which can transfer gene sequences between cells. For example, baculoviral vector can be used in the present disclosure. In another example, adenoviral vector can be used in the present disclosure. Thus, the term includes cloning and expression vehicles, as well as viral vectors. In some embodiments, useful vectors are contemplated to be those vectors in which the nucleic acid segment to be transcribed is positioned under the transcriptional control of a promoter. A "promoter" refers to a DNA sequence recognized by the synthetic machinery of the cell, or introduced synthetic machinery, required to initiate the specific transcription of a gene. The phrases "operatively positioned," "under control" or "under transcriptional control" means that the promoter is in the correct location and orientation in relation to the nucleic acid to control RNA polymerase initiation and expression of the gene. The term "expression vector or construct" means any type of genetic construct containing a nucleic acid in which part or all of the nucleic acid encoding sequence is capable of being transcribed. In some embodiments, expression includes transcription of the nucleic acid, for example, to generate a biologically-active polypeptide product or inhibitory RNA (e.g., shRNA, miRNA, miRNA inhibitor) from a transcribed gene.

The foregoing methods for packaging recombinant vectors in desired AAV capsids to produce the rAAVs of the disclosure are not meant to be limiting and other suitable methods may be used.

Recombinant AAV Vector: Transgene Coding Sequences

The composition of the transgene sequence of the rAAV vector will depend upon the use to which the resulting vector will be put. For example, one type of transgene sequence includes a reporter sequence, which upon expression produces a detectable signal. In another example, the transgene encodes a therapeutic protein or therapeutic functional RNA. In another example, the transgene encodes a transmembrane protein. In another example, the transgene encodes a secreted protein. In another example, the transgene encodes a protein or functional RNA that is intended to be used for research purposes, e.g., to create a somatic transgenic animal model harboring the transgene, e.g., to study the function of the transgene product. In another example, the transgene encodes a protein or functional RNA that is intended to be used to create an animal model of disease. Appropriate transgene coding sequences will be apparent to the skilled artisan.

Reporter sequences that may be provided in a transgene include, without limitation, DNA sequences encoding β-lactamase, β-galactosidase (LacZ), alkaline phosphatase, thymidine kinase, green fluorescent protein (GFP), chloramphenicol acetyltransferase (CAT), luciferase, Ovalbumin (OVA) and others well known in the art. When associated with regulatory elements which drive their expression, the reporter sequences, provide signals detectable by conventional means, including enzymatic, radiographic, colorimetric, fluorescence or other spectrographic assays, fluorescent activating cell sorting assays and immunological assays, including enzyme linked immunosorbent assay (ELISA), radioimmunoassay (RIA) and immunohistochemistry. For example, where the marker sequence is the LacZ gene, the presence of the vector carrying the signal is detected by assays for β-galactosidase activity. Where the transgene is green fluorescent protein or luciferase, the vector carrying the signal may be measured visually by color or light production in a luminometer. Such reporters can, for example, be useful in verifying the tissue-specific targeting capabilities and tissue specific promoter regulatory activity of an rAAV.

In some aspects, the disclosure provides rAAV vectors for use in methods of preventing or treating one or more genetic deficiencies or dysfunctions in a mammal, such as for example, a polypeptide deficiency or polypeptide excess in a mammal, and particularly for treating or reducing the severity or extent of deficiency in a human manifesting one or more of the disorders linked to a deficiency in such polypeptides in cells and tissues. The method involves administration of an rAAV vector that encodes one or more therapeutic peptides, polypeptides, siRNAs, microRNAs, antisense nucleotides, etc. in a pharmaceutically-acceptable carrier to the subject in an amount and for a period of time sufficient to treat the deficiency or disorder in the subject suffering from such a disorder.

Thus, the disclosure embraces the delivery of vectors encoding one or more peptides, polypeptides, or proteins, which are useful for the treatment or prevention of disease states in a mammalian subject. Exemplary therapeutic proteins include one or more polypeptides selected from the group consisting of growth factors, interleukins, interferons, anti-apoptosis factors, cytokines, anti-diabetic factors, anti-apoptosis agents, coagulation factors, anti-tumor factors. Other non-limiting examples of therapeutic proteins include BDNF, CNTF, CSF, EGF, FGF, G-SCF, GM-CSF, gonadotropin, IFN, IFG-1, M-CSF, NGF, PDGF, PEDF, TGF, VEGF, TGF-B2, TNF, prolactin, somatotropin, XIAP1, IL-1, IL-2, IL-3, IL-4, IL-5, IL-6, IL-7, IL-8, IL-9, IL-10, IL-10(187A), viral IL-10, IL-11, IL-12, IL-13, IL-14, IL-15, IL-16 IL-17, and IL-18. In some In some embodiments, therapeutic proteins include any polypeptide that is suitable for the purpose of delivering the recombinant rAAV and/or treating or preventing a disease.

The vectors disclosed herein may comprise a transgene to be transferred to a subject to treat a disease associated with reduced expression, lack of expression or dysfunction of the native gene. Exemplary genes and associated disease states include, but are not limited to: glucose-6-phosphatase, associated with glycogen storage deficiency type 1A; phosphoenolpyruvate-carboxykinase, associated with Pepck deficiency; galactose-1 phosphate uridyl transferase, associated with galactosemia; phenylalanine hydroxylase, associated with phenylketonuria; branched chain alpha-ketoacid dehydrogenase, associated with Maple syrup urine disease; fumarylacetoacetate hydrolase, associated with tyrosinemia type 1; methylmalonyl-CoA mutase, associated with methylmalonic acidemia; medium chain acyl CoA dehydrogenase, associated with medium chain acetyl CoA deficiency; ornithine transcarbamylase, associated with ornithine transcarbamylase deficiency; argininosuccinic acid synthetase, associated with citrullinemia; low density lipoprotein receptor protein, associated with familial hypercholesterolemia; UDP-glucouronosyltransferase, associated with Crigler-Najjar disease; adenosine deaminase, associated with severe combined immunodeficiency disease; hypoxanthine guanine phosphoribosyl transferase, associated with Gout and Lesch-Nyan syndrome; biotinidase, associated with biotinidase deficiency; beta-glucocerebrosidase, associated with Gaucher disease; beta-glucuronidase, associated with Sly syndrome; peroxisome membrane protein 70 kDa, associated with Zellweger syndrome; porphobilinogen deaminase, associated with acute intermittent *porphyria*; alpha-1 antitrypsin for treatment of alpha-1 antitrypsin deficiency (emphysema); erythropoietin for treatment of anemia due to thalassemia or to renal failure; vascular endothelial growth factor, angiopoietin-1, and fibroblast growth factor for the treatment of ischemic diseases; thrombomodulin and tissue factor pathway inhibitor for the treatment of occluded blood vessels as seen in, for example, atherosclerosis, thrombosis, or embolisms; aromatic amino acid decarboxylase (AADC), and tyrosine hydroxylase (TH) for the treatment of Parkinson's disease; the beta adrenergic receptor, anti-sense to, or a mutant form of, phospholamban, the sarco(endo)plasmic reticulum adenosine triphosphatase-2 (SERCA2), and the cardiac adenylyl cyclase for the treatment of congestive heart failure; a tumor suppressor gene such as p53 for the treatment of various cancers; a cytokine such as one of the various interleukins for the treatment of inflammatory and immune disorders and cancers; dystrophin or minidystrophin and utrophin or miniutrophin for the treatment of muscular dystrophies; and, insulin for the treatment of diabetes.

The following are further non-limiting examples of proteins that may be encoded by transgenes of the vectors disclosed herein to treat a disease associated with reduced expression, lack of expression or dysfunction of the native gene: a-galactosidase, acid-glucosidase, adiopokines, adiponectin, alglucosidase alfa, anti-thrombin, ApoAV, ApoCII, apolipoprotein A-I (APOA1), arylsulfatase A, arylsulfatase B, ATP-binding cassette transporter A1 (ABCA1), ABCD1, CCR5 receptor, erythropoietin, Factor VIII, Factor VII, Factor IX, Factor V, fetal hemoglobin, beta-globin, GPI-anchored HDL-binding protein (GPI-HBP) I, growth hormone, hepatocyte growth factor, imiglucerase, lecithin-cholesterol acyltransferase (LCAT), leptin, LDL receptor, lipase maturation factor (LMF) 1, lipoprotein lipase, lysozyme, nicotinamide dinucleotide phosphate (NADPH) oxidase, Rab escort protein-1 (REP-1), retinal degeneration slow (RDS), retinal pigment epithelium-specific 65 (RPE65), rhodopsin, T cell receptor alpha or beta chains, thrombopoeitin, tyrosine hydroxylase, VEGF, von heldebrant factor, von willebrant factor, and X-linked inhibitor of apoptosis (XIAP).

In some embodiments, the rAAV vectors may comprise a gene encoding an antigen-binding protein, such as an immunoglobulin heavy chain or light chain or fragment thereof, e.g., that may be used for therapeutic purposes. In some embodiments, the protein is a single chain Fv fragment or Fv-Fc fragment. Accordingly, in some embodiments, the rAAV can be used to infect cells are of target tissue (e.g., muscle tissue) to engineer cells of the tissue to express an antigen-binding protein, such as an antibody or fragment thereof. In some embodiments, to generate rAAVs that express the antibodies or antigen binding fragments, cDNAs engineered to express such proteins will be subcloned into an appropriate plasmid backbone and packaged into an rAAV.

The rAAVs of the disclosure can be used to restore the expression of genes that are reduced in expression, silenced, or otherwise dysfunctional in a subject (e.g., a tumor suppressor that has been silenced in a subject having cancer). The rAAVs of the disclosure can also be used to knockdown the expression of genes that are aberrantly expressed in a subject (e.g., an oncogene that is expressed in a subject having cancer).

The skilled artisan will also realize that in the case of transgenes encoding proteins or polypeptides, that mutations that results in conservative amino acid substitutions may be made in a transgene to provide functionally equivalent variants, or homologs of a protein or polypeptide. In some aspects, the disclosure embraces sequence alterations that result in conservative amino acid substitution of a transgene. In some embodiments, the transgene comprises a gene having a dominant negative mutation. For example, a transgene may express a mutant protein that interacts with the same elements as a wild-type protein, and thereby blocks some aspect of the function of the wild-type protein.

In some embodiments, the cloning capacity of the recombinant RNA vector may be limited and a desired coding sequence may require the complete replacement of the virus's 4.8 kilobase genome. Large genes may, therefore, not be suitable for use in a standard recombinant AAV vector, in some cases. The skilled artisan will appreciate that options are available in the art for overcoming a limited coding capacity. For example, the AAV ITRs of two genomes can anneal to form head to tail concatamers, almost doubling the capacity of the vector. Insertion of splice sites allows for the removal of the ITRs from the transcript. Other options for overcoming a limited cloning capacity will be apparent to the skilled artisan.

Although the disclosure provides rAAVs and related vectors, it should be appreciated that in some embodiments immune-related miRNAs may be engineered into transgenes that are delivered using other vectors, such as, for example, vectors for use with retroviruses, oncoretroviruses, adenoviruses, ONYX-015, Herpes simplex viruses, moloney murine leukemia viruses (MMLV), and vaccinia viruses.

Recombinant AAV Administration Methods

The rAAVs may be delivered to a subject in compositions according to any appropriate methods known in the art. The rAAV, preferably suspended in a physiologically compatible carrier (e.g., in a composition), may be administered to a subject, e.g. host animal, such as a human, mouse, rat, cat, dog, sheep, rabbit, horse, cow, goat, pig, guinea pig, hamster, chicken, turkey, or a non-human primate (e.g, Macaque). In some embodiments a host animal does not include a human.

Delivery of the rAAVs to a mammalian subject may be by, for example, intramuscular injection or by administration into the bloodstream of the mammalian subject. Administration into the bloodstream may be by injection into a vein, an artery, or any other vascular conduit. In some embodiments, the rAAVs are administered into the bloodstream by way of isolated limb perfusion, a technique well known in the surgical arts, the method essentially enabling the artisan to isolate a limb from the systemic circulation prior to administration of the rAAV virions. A variant of the isolated limb perfusion technique, described in U.S. Pat. No. 6,177,403, can also be employed by the skilled artisan to administer the virions into the vasculature of an isolated limb to potentially enhance transduction into muscle cells or tissue. Moreover, in certain instances, it may be desirable to deliver the virions to the CNS of a subject. By "CNS" is meant all cells and tissue of the brain and spinal cord of a vertebrate. Thus, the term includes, but is not limited to, neuronal cells, glial cells, astrocytes, cereobrospinal fluid (CSF), interstitial spaces, bone, cartilage and the like. Recombinant AAVs may be delivered directly to the CNS or brain by injection into, e.g., the ventricular region, as well as to the striatum (e.g., the caudate nucleus or putamen of the striatum), spinal cord and neuromuscular junction, or cerebellar lobule, with a needle, catheter or related device, using neurosurgical techniques known in the art, such as by stereotactic injection (see, e.g., Stein et al., J Virol 73:3424-3429, 1999; Davidson et al., PNAS 97:3428-3432, 2000; Davidson et al., Nat. Genet. 3:219-223, 1993; and Alisky and Davidson, Hum. Gene Ther. 11:2315-2329, 2000).

The compositions of the disclosure may comprise an rAAV alone, or in combination with one or more other viruses (e.g., a second rAAV encoding having one or more different transgenes). In some embodiments, a composition comprises 1, 2, 3, 4, 5, 6, 7, 8, 9, 10, or more different rAAVs each having one or more different transgenes.

Suitable carriers may be readily selected by one of skill in the art in view of the indication for which the rAAV is directed. For example, one suitable carrier includes saline, which may be formulated with a variety of buffering solutions (e.g., phosphate buffered saline). Other exemplary carriers include sterile saline, lactose, sucrose, calcium phosphate, gelatin, dextran, agar, pectin, peanut oil, sesame oil, and water. The selection of the carrier is not a limitation of the present disclosure.

Optionally, the compositions of the disclosure may contain, in addition to the rAAV and carrier(s), other conventional pharmaceutical ingredients, such as preservatives, or chemical stabilizers. Suitable exemplary preservatives include chlorobutanol, potassium sorbate, sorbic acid, sulfur dioxide, propyl gallate, the parabens, ethyl vanillin, glycerin, phenol, and parachlorophenol. Suitable chemical stabilizers include gelatin and albumin.

The rAAVs are administered in sufficient amounts to transfect the cells of a desired tissue and to provide sufficient levels of gene transfer and expression without undue adverse effects. Conventional and pharmaceutically acceptable routes of administration include, but are not limited to, direct delivery to the selected organ (e.g., intraportal delivery to the liver), oral, inhalation (including intranasal and intratracheal delivery), intraocular, intravenous, intramuscular, subcutaneous, intradermal, intratumoral, and other parental routes of administration. In some embodiments, the route of administration is intramuscular. Routes of administration may be combined, if desired.

The dose of rAAV virions required to achieve a particular "therapeutic effect," e.g., the units of dose in genome copies/per kilogram of body weight (GC/kg), will vary based on several factors including, but not limited to: the route of rAAV virion administration, the level of gene or RNA expression required to achieve a therapeutic effect, the specific disease or disorder being treated, and the stability of the gene or RNA product. One of skill in the art can readily determine a rAAV virion dose range to treat a patient having a particular disease or disorder based on the aforementioned factors, as well as other factors that are well known in the art.

An effective amount of an rAAV is an amount sufficient to target or infect an animal, or target a desired tissue. In some embodiments, an effective amount of an rAAV is an amount sufficient to produce a stable somatic transgenic animal model. The effective amount will depend primarily on factors such as the species, age, weight, health of the subject, and the tissue to be targeted, and may thus vary among animal and tissue. For example, an effective amount of the rAAV is generally in the range of from about 1 ml to about 100 ml of solution containing from about $10^9$ to $10^{16}$ genome copies. In some embodiments, the rAAV transduces hepatocytes. In certain embodiments, the effective amount of rAAV is $10^{10}$, $10^{11}$, $10^{12}$, $10^{13}$, or $10^{14}$ genome copies per kg. In certain embodiments, the effective amount of rAAV is $10^{10}$, $10^{11}$, $10^{12}$, $10^{13}$, $10^{14}$, or $10^{15}$ genome copies per subject. In some cases, a dosage between about $10^{11}$ to $10^{12}$ rAAV genome copies is appropriate. For example, in certain embodiments, $10^{12}$ rAAV genome copies is effective to target heart, liver, and pancreas tissues. In some embodiments, a dose of rAAV for intramuscular injection is $10^{11}$ GC/25 g body weight. In some embodiments, the dosage in the range of $10^{11}$ to $10^{13}$ genome copies per kg.

In some embodiments, rAAV compositions are formulated to reduce aggregation of AAV particles in the composition, particularly where high rAAV concentrations are present (e.g., ~$10^{13}$ GC/ml or more). Methods for reducing aggregation of rAAVs are well known in the art and, include, for example, addition of surfactants, pH adjustment, salt concentration adjustment, etc. (See, e.g., Wright FR, et al., Molecular Therapy (2005) 12, 171-178, the contents of which are incorporated herein by reference.)

Formulation of pharmaceutically-acceptable excipients and carrier solutions is well-known to those of skill in the art, as is the development of suitable dosing and treatment regimens for using the particular compositions described herein in a variety of treatment regimens.

Typically, these formulations may contain at least about 0.1% of the active compound or more, although the percentage of the active ingredient(s) may, of course, be varied and may conveniently be between about 1 or 2% and about 70% or 80% or more of the weight or volume of the total formulation. Naturally, the amount of active compound in each therapeutically-useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In certain circumstances it will be desirable to deliver the rAAV-based therapeutic constructs in suitably formulated pharmaceutical compositions disclosed herein either subcutaneously, intraopancreatically, intranasally, parenterally, intravenously, intramuscularly, intrathecally, or orally, intraperitoneally, or by inhalation. In some embodiments, the administration modalities as described in U.S. Pat. Nos. 5,543,158; 5,641,515 and 5,399,363 (each specifically incorporated herein by reference in its entirety) may be used to deliver rAAVs. In some embodiments, a preferred mode of administration is by portal vein injection.

The pharmaceutical forms suitable for injectable use include sterile aqueous solutions or dispersions and sterile powders for the extemporaneous preparation of sterile injectable solutions or dispersions. Dispersions may also be prepared in glycerol, liquid polyethylene glycols, and mixtures thereof and in oils. Under ordinary conditions of storage and use, these preparations contain a preservative to prevent the growth of microorganisms. In many cases the form is sterile and fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For administration of an injectable aqueous solution, for example, the solution may be suitably buffered, if necessary, and the liquid diluent first rendered isotonic with sufficient saline or glucose. These particular aqueous solutions are especially suitable for intravenous, intramuscular, subcutaneous and intraperitoneal administration. In this connection, a sterile aqueous medium that can be employed will be known to those of skill in the art. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the host. The person responsible for administration will, in any event, determine the appropriate dose for the individual host.

Sterile injectable solutions are prepared by incorporating the active rAAV in the required amount in the appropriate solvent with various of the other ingredients enumerated herein, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The rAAV compositions disclosed herein may also be formulated in a neutral or salt form. Pharmaceutically-acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug-release capsules, and the like.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Supplementary active ingredients can also be incorporated into the compositions. The phrase "pharmaceutically-acceptable" refers to molecular entities and compositions that do not produce an allergic or similar untoward reaction when administered to a host.

Delivery vehicles such as liposomes, nanocapsules, microparticles, microspheres, lipid particles, vesicles, and the like, may be used for the introduction of the compositions of the present disclosure into suitable host cells. In particular, the rAAV vector delivered transgenes may be formulated for delivery either encapsulated in a lipid particle, a liposome, a vesicle, a nanosphere, or a nanoparticle or the like.

Such formulations may be preferred for the introduction of pharmaceutically acceptable formulations of the nucleic acids or the rAAV constructs disclosed herein. The formation and use of liposomes is generally known to those of skill in the art. Recently, liposomes were developed with improved serum stability and circulation half-times (U.S. Pat. No. 5,741,516). Further, various methods of liposome and liposome like preparations as potential drug carriers have been described (U.S. Pat. Nos. 5,567,434; 5,552,157; 5,565,213; 5,738,868 and 5,795,587).

Liposomes have been used successfully with a number of cell types that are normally resistant to transfection by other procedures. In addition, liposomes are free of the DNA length constraints that are typical of viral-based delivery systems. Liposomes have been used effectively to introduce genes, drugs, radiotherapeutic agents, viruses, transcription factors and allosteric effectors into a variety of cultured cell lines and animals. In addition, several successful clinical trials examining the effectiveness of liposome-mediated drug delivery have been completed.

Liposomes are formed from phospholipids that are dispersed in an aqueous medium and spontaneously form multilamellar concentric bilayer vesicles (also termed multilamellar vesicles (MLVs). MLVs generally have diameters of from 25 nm to 4 µm. Sonication of MLVs results in the formation of small unilamellar vesicles (SUVs) with diameters in the range of 200 to 500.ANG., containing an aqueous solution in the core.

Alternatively, nanocapsule formulations of the rAAV may be used. Nanocapsules can generally entrap substances in a stable and reproducible way. To avoid side effects due to intracellular polymeric overloading, such ultrafine particles (sized around 0.1 µm) should be designed using polymers able to be degraded in vivo. Biodegradable polyalkyl-cyanoacrylate nanoparticles that meet these requirements are contemplated for use.

In addition to the methods of delivery described above, the following techniques are also contemplated as alternative methods of delivering the rAAV compositions to a host. Sonophoresis (ie., ultrasound) has been used and described in U.S. Pat. No. 5,656,016 as a device for enhancing the rate and efficacy of drug permeation into and through the circulatory system. Other drug delivery alternatives contemplated are intraosseous injection (U.S. Pat. No. 5,779,708), microchip devices (U.S. Pat. No. 5,797,898), ophthalmic formulations (Bourlais et al., 1998), transdermal matrices (U.S. Pat. Nos. 5,770,219 and 5,783,208) and feedback-controlled delivery (U.S. Pat. No. 5,697,899).

Kits and Related Compositions

The agents described herein may, in some embodiments, be assembled into pharmaceutical or diagnostic or research kits to facilitate their use in therapeutic, diagnostic or research applications. A kit may include one or more containers housing the components of the disclosure and instructions for use. Specifically, such kits may include one or more agents described herein, along with instructions describing the intended application and the proper use of these agents. In certain embodiments agents in a kit may be in a pharmaceutical formulation and dosage suitable for a particular application and for a method of administration of the agents. Kits for research purposes may contain the components in appropriate concentrations or quantities for running various experiments.

The kit may be designed to facilitate use of the methods described herein by researchers and can take many forms. Each of the compositions of the kit, where applicable, may be provided in liquid form (e.g., in solution), or in solid form, (e.g., a dry powder). In certain cases, some of the compositions may be constitutable or otherwise processable (e.g., to an active form), for example, by the addition of a suitable solvent or other species (for example, water or a cell culture medium), which may or may not be provided with the kit. As used herein, "instructions" can define a component of instruction and/or promotion, and typically involve written instructions on or associated with packaging of the disclosure. Instructions also can include any oral or electronic instructions provided in any manner such that a user will clearly recognize that the instructions are to be associated with the kit, for example, audiovisual (e.g., videotape, DVD, etc.), Internet, and/or web-based communications, etc. The written instructions may be in a form prescribed by a governmental agency regulating the manufacture, use or sale of pharmaceuticals or biological products, which instructions can also reflect approval by the agency of manufacture, use or sale for animal administration.

The kit may contain any one or more of the components described herein in one or more containers. As an example, in one embodiment, the kit may include instructions for mixing one or more components of the kit and/or isolating and mixing a sample and applying to a subject. The kit may include a container housing agents described herein. The agents may be in the form of a liquid, gel or solid (powder).

The agents may be prepared sterilely, packaged in syringe and shipped refrigerated. Alternatively, it may be housed in a vial or other container for storage. A second container may have other agents prepared sterilely. Alternatively, the kit may include the active agents premixed and shipped in a syringe, vial, tube, or other container. The kit may have one or more or all of the components required to administer the agents to an animal, such as a syringe, topical application devices, or iv needle tubing and bag, particularly in the case of the kits for producing specific somatic animal models.

In some cases, the methods involve transfecting cells with total cellular DNAs isolated from the tissues that potentially harbor proviral AAV genomes at very low abundance and supplementing with helper virus function (e.g., adenovirus) to trigger and/or boost AAV rep and cap gene transcription in the transfected cell. In some cases, RNA from the transfected cells provides a template for RT-PCR amplification of cDNA and the detection of novel AAVs. In cases where cells are transfected with total cellular DNAs isolated from the tissues that potentially harbor proviral AAV genomes, it is often desirable to supplement the cells with factors that promote AAV gene transcription. For example, the cells may also be infected with a helper virus, such as an Adenovirus or a Herpes Virus. In a specific embodiment, the helper functions are provided by an adenovirus. The adenovirus may be a wild-type adenovirus, and may be of human or non-human origin, preferably non-human primate (NHP) origin. Similarly, adenoviruses known to infect non-human animals (e.g., chimpanzees, mouse) may also be employed in the methods of the disclosure (See, e.g., U.S. Pat. No. 6,083,716). In addition to wild-type adenoviruses, recombinant viruses or non-viral vectors (e.g., plasmids, episomes, etc.) carrying the necessary helper functions may be utilized. Such recombinant viruses are known in the art and may be prepared according to published techniques. See, e.g., U.S. Pat. Nos. 5,871,982 and 6,251,677, which describe a hybrid Ad/AAV virus. A variety of adenovirus strains are available from the American Type Culture Collection, Manassas, Va., or available by request from a variety of commercial and institutional sources. Further, the sequences of many such strains are available from a variety of databases including, e.g., PubMed and GenBank.

Cells may also be transfected with a vector (e.g., helper vector) which provides helper functions to the AAV. The vector providing helper functions may provide adenovirus functions, including, e.g., E1a, E1b, E2a, E4ORF6. The sequences of adenovirus gene providing these functions may be obtained from any known adenovirus serotype, such as serotypes 2, 3, 4, 7, 12 and 40, and further including any of the presently identified human types known in the art. Thus, in some embodiments, the methods involve transfecting the cell with a vector expressing one or more genes necessary for AAV replication, AAV gene transcription, and/or AAV packaging.

In some cases, a novel isolated capsid gene can be used to construct and package recombinant AAV vectors, using methods well known in the art, to determine functional characteristics associated with the novel capsid protein encoded by the gene. For example, novel isolated capsid genes can be used to construct and package recombinant AAV (rAAV) vectors comprising a reporter gene (e.g., B-Galactosidase, GFP, Luciferase, etc.). The rAAV vector can then be delivered to an animal (e.g., mouse) and the tissue targeting properties of the novel isolated capsid gene can be determined by examining the expression of the reporter gene in various tissues (e.g., heart, liver, kidneys) of the animal. Other methods for characterizing the novel isolated capsid genes are disclosed herein and still others are well known in the art. The kit may have a variety of forms, such as a blister pouch, a shrink wrapped pouch, a vacuum sealable pouch, a sealable thermoformed tray, or a similar pouch or tray form, with the accessories loosely packed within the pouch, one or more tubes, containers, a box or a bag. The kit may be sterilized after the accessories are added, thereby allowing the individual accessories in the container to be otherwise unwrapped. The kits can be sterilized using any appropriate sterilization techniques, such as radiation sterilization, heat sterilization, or other sterilization methods known in the art. The kit may also include other components, depending on the specific application, for example, containers, cell media, salts, buffers, reagents, syringes, needles, a fabric, such as gauze, for applying or removing a disinfecting agent, disposable gloves, a support for the agents prior to administration etc.

The instructions included within the kit may involve methods for detecting a latent AAV in a cell. In addition, kits of the disclosure may include, instructions, a negative and/or positive control, containers, diluents and buffers for the sample, sample preparation tubes and a printed or electronic table of reference AAV sequence for sequence comparisons.

EXAMPLES

Example 1: In Vitro Testing of Aav-Mirna Binding Site Constructs

Figure 1A:
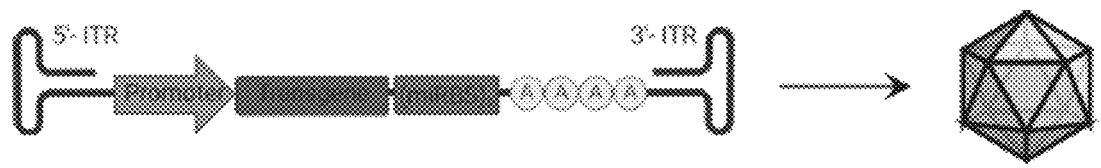
FIGS. 1A-1C depict one embodiment of a miRNA-mediated detargeting strategy.
Figures 1B, 1C:
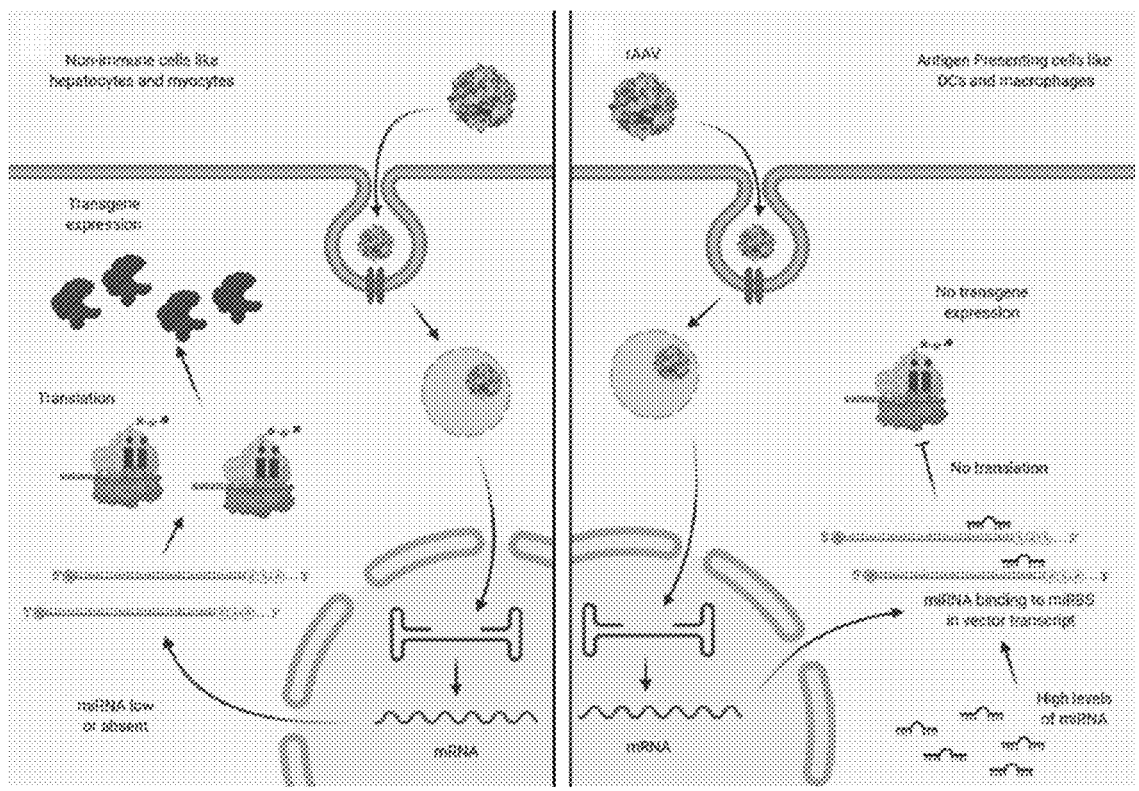

The following examples demonstrate effectiveness of immune-related miRNA sequences for inhibiting expression of transgenes in antigen presenting cells (APCs). Endogenous miRNAs that are highly expressed in APCs, but not in muscle cells were identified (Table 1). It should be appreciated that in Table 1 (as well as any other miRNABS sequences disclosed herein), all "T" nucleobases may be substituted with "U" nucleobases, and vice versa. Immune-related miRNA species were selected which include but are not limited to miR-106, miR-125a, miR-125b, miR-126a, miR-142, miR-146a, miR-15, miR-150, miR-155, miR-16, miR-17, miR-18, miR-181a, miR-19a, miR-19b, miR-20, miR-21a, miR-223, miR-24-3p, miR-29a, miR-29b, miR-29c, miR-302a-3p, miR-30b, miR-33-5p, miR-34a, miR-424, miR-652-3p, miR-652-5p, miR-9-3p, miR-9-5p, miR-92a, and miR-99b-5p. FIGS. 1A-1C depict one embodiment of a miRNA-mediated detargeting strategy. FIG. 1A shows a generic vector genome design harboring miRNA binding sites (miRBS). FIG. 1B depicts permissive transduction of rAAV into a non-immune host cell, such as a hepatocyte or myocyte. FIG. 1C shows high levels of endogenous miRNAs enriched in antigen-presenting cells (APCs) prohibit translation of transgenes in these transduced cell types.

Table 1 shows the immune cell types enriched with the respective miRNA, sequences of the binding site of the listed miRNAs, and sequence similarity between mouse and human. The listed miRNAs are involved in the proliferation, differentiation and maturation of dendritic cells, macrophages, monocytes, B cell, or T cells, for example. OVA transgene was used as a proxy for foreign antigens. The above miRNA binding sites were synthesized and cloned into 3'UTR of ovalbumin (OVA) transgene, whose expression is driven by the ubiquitous chicken-0 actin/CMV promoter (CB6), in the context of AAV vector. Ovalbumin is highly immunogenic for mice and it has been used to study the immune response of mice to rAAV-mediated transgene products.

Two tandem binding sites for each miRNA species were used. Different combinations of miRNA binding sites, e.g., incorporating two different species of miRNA binding sites, were also tested to see if there is a synergistic effect. All the combinations containing any two of the 33 miRNAs (listed above and Table 1) were considered. miR-223-3pBS, miR-652-5pBS, and miR-33-5pBS were selected for combinatorial designs with miR-142BS. For example, miR-142BS+miR-33-5pBS, miR-142BS+miR-223BS, miR-142BS+miR-652-5pBS, etc.

Additionally, different miRNA binding sites which work with high efficiency may be combined into one construct. Different miRNA binding sites that work in different cell types may also be combined. For instance, miR-106BS works efficiently in monocytes and miR-142BS works efficiently in dendritic cells. Thus, the two miRNA binding sites may be combined in one construct to achieve de-targeting in multiple immune cells.

Figure 2A:
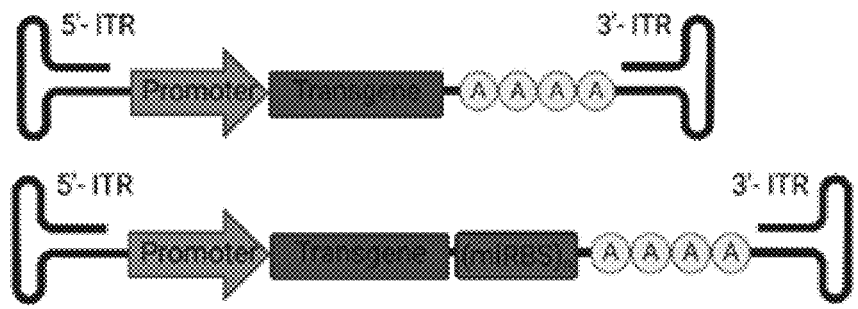
FIGS. 2A-2C show in vitro screening of candidate miRBS (binding site) of cognate miRNAs that were enriched in immune cells.
Figure 2B:
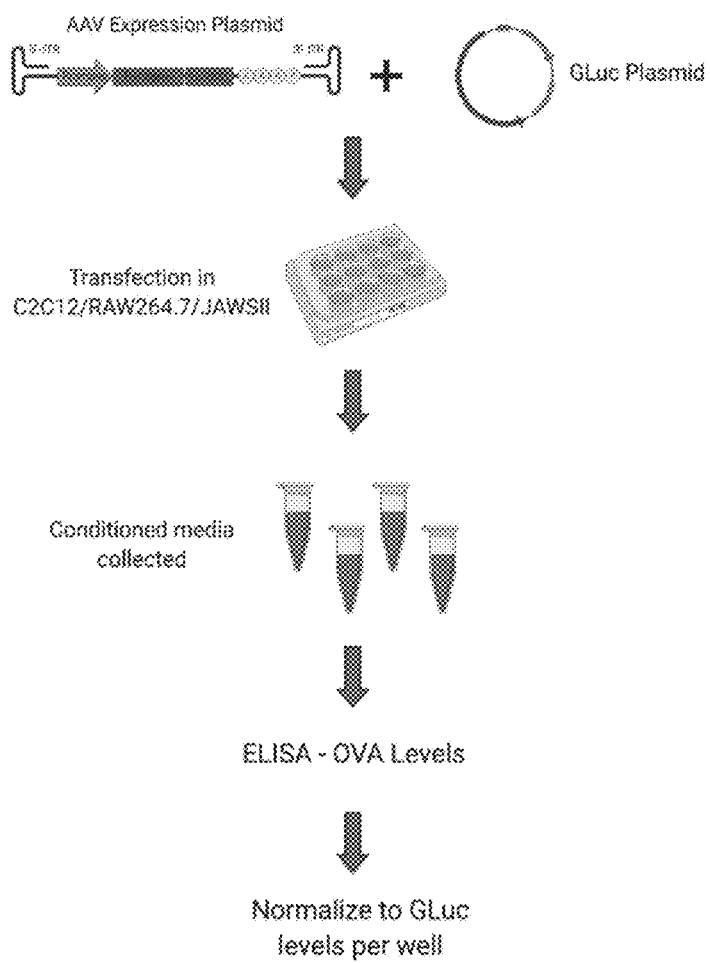
Figure 2C:
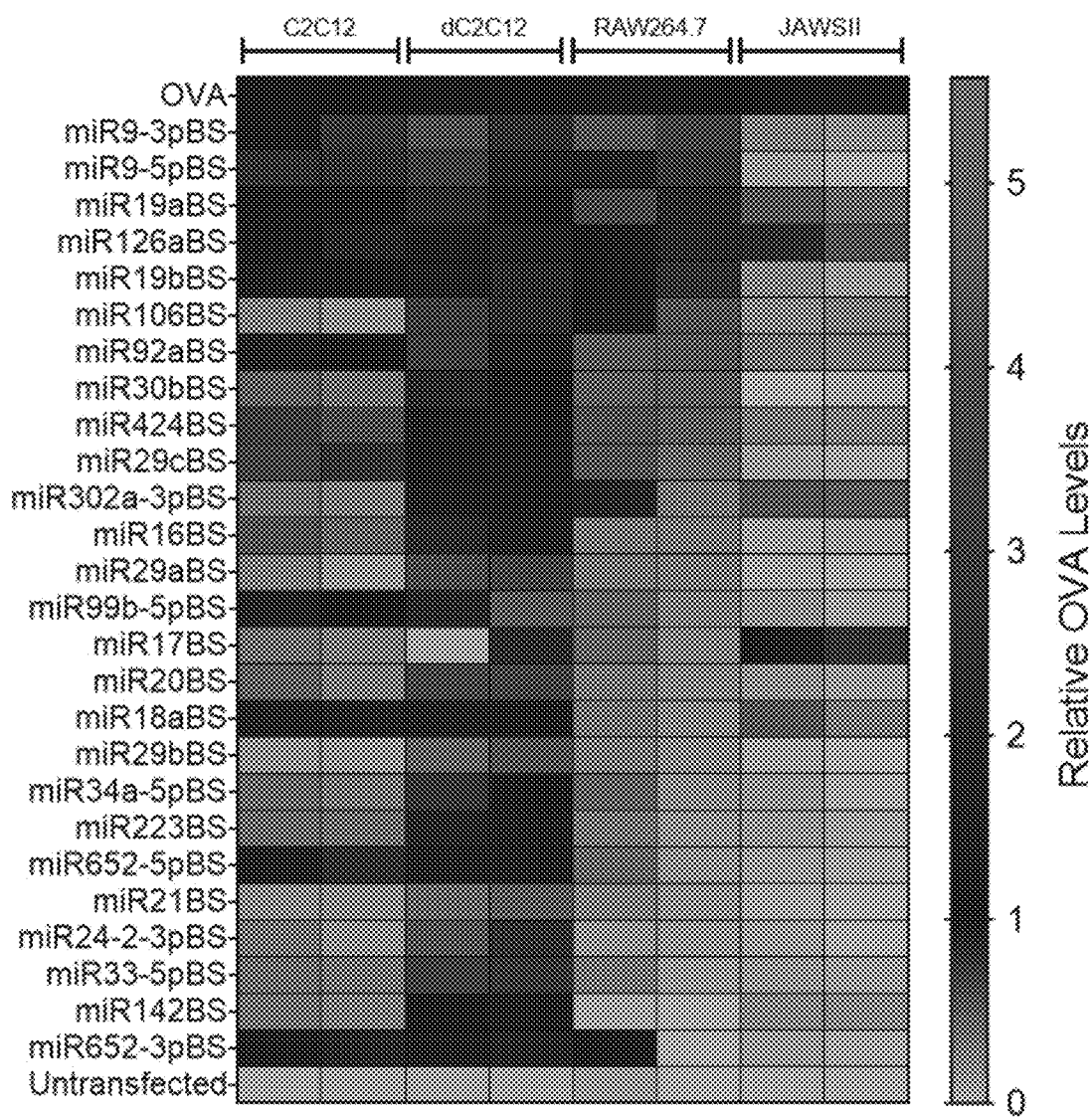

Mouse dendritic cell lines (JAWSII), macrophage cell lines (RAW264.7) and myocytes (dC2C12) were used to screen for miRBS-mediated APC detargeting. Myoblast cell lines (C2C12) were used to gauge the preservation of transgene expression in muscle. Myoblasts, myocytes, macrophages and dendritic cells were transiently transfected with AAV1-CB6-OVA constructs carrying 25 miRBS candidates as shown in FIGS. 2A-2D. Multiple candidate miR-BS cassettes downregulated OVA transgene expression in dendritic cells and macrophages, while retaining myoblast and myocyte expression in vitro (FIG. 2C).

Figure 11A:
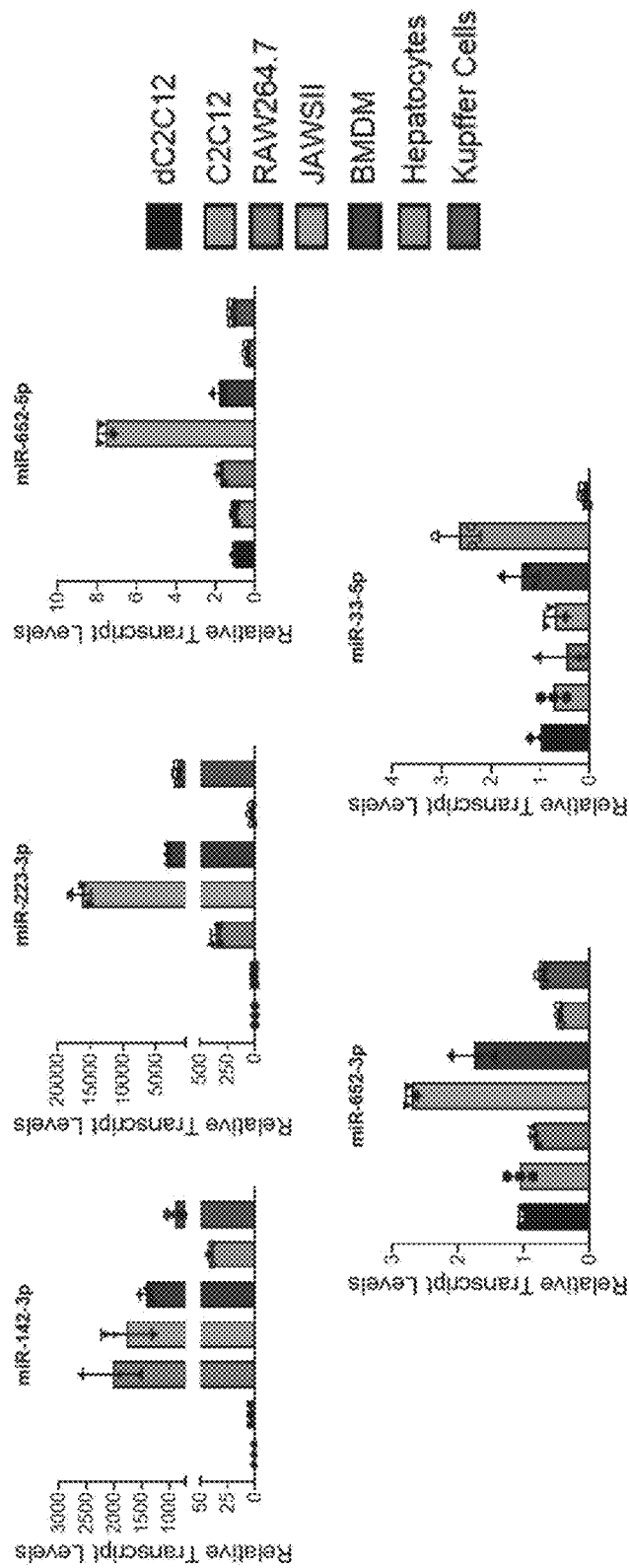
FIGS. 11A-11F show that the incorporation of miR-223BSs and miR-652BSs boosted in vivo OVA production and suppresses antibody development.

To provide support that the miR-BS cassettes were operating through endogenously expressed cognate miRNAs, the levels of these miRNAs in cells were quantified from immunological and non-immunological lineages to demonstrate their levels of enrichment in APCs. miR-223-3p was found to be approximately 500- to 15,000-fold higher in cell types of the immunological lineage (RAW264.7, JAWSII, bone marrow derived macrophages (BMDM), and Kupffer cells) than in C2C12 and differentiated C2C12 cell (FIG. 11A). Expression of miR-652-5p in RAW264.7 and JAWSII cells was about 2- and 8-fold higher than levels observed in C2C12 cells, respectively. no significant enrichment of miR-652-3p and miR-33-5p was seen in immune cell types (FIG. 11A).

Figure 3A:
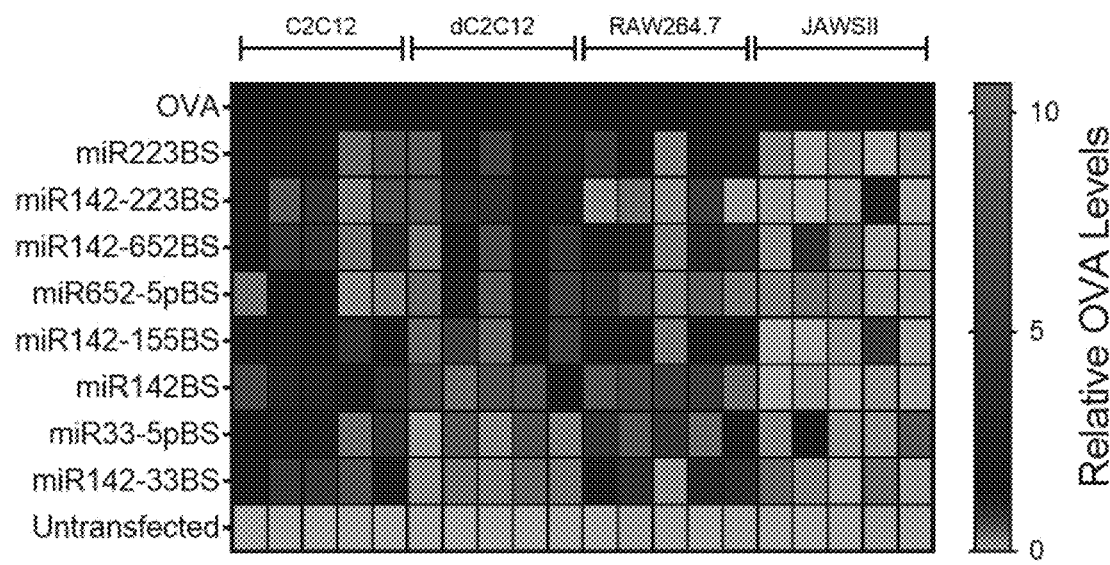
Figure 3B:
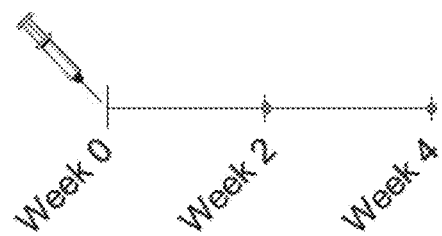

Next, miR-33-5pBS, miR-223BS, and miR-652-5pBS in combination with miR-142BS were tested (FIGS. 3A-3C). The data shows that miR-BSs have a combinatorial effect in reducing transgene expression in APCs that appears to be cell-type specific. For example, the tested combinations of miRBSs generally had more reduced transgene expression in JAWSII cells than other cells. It was therefore hypothesized that these miR-BS cassettes may provide improved detargeting from APCs in vivo, resulting in a reduction in immunological responses and increased transgene expression.

TABLE 1

Sequences of miRNA binding sites.

| miRNA | cell types miRNA is enriched in | binding site sequence | mouse vs. human similarity | SEQ IDs |
|---|---|---|---|---|
| miR-106 | Monocyte | (CTACCTGCACTGTTAGCACTTTG)$_2$ | 2 base differences | 1 |
| miR-125a | B, DC, Monocyte | (TCACAGGTTAAAGGGTCTCAGGGA)$_2$ | identical | 2 |
| miR-125b | B, DC, Monocyte | (TCACAAGTTAGGGTCTCAGGGA)$_2$ | identical | 3 |
| miR-126a | pDC | (CGCATTATTACTCACGGTACGA)$_2$ | identical | 4 |
| miR-142 | DC | (TCCATAAAGTAGGAAACACTACA)$_2$ | identical | 5 |
| miR-146a | Monocyte | (AACCCATGGAATTCAGTTCTCA)$_2$ | identical | 6 |
| miR-15 | Monocyte | (CACAAACCATTATGTGCTGCTA)$_2$ | identical | 7 |
| miR-150 | B, T | (CACTGGTACAAGGGTTGGGAGA)$_2$ | identical | 8 |
| miR-155 | B, T, DC, MF | (ACCCCTATCACAATTAGCATTAA)$_2$ | 12th base U to C and extra U at human 3' end | 9 |
| miR-16 | B | (CGCCAATATTTACGTGCTGCTA)$_2$ | identical | 10 |
| miR-17 | B, T, Monocyte | (CTACCTGCACTGTAAGCACTTTG)$_2$ | identical | 11 |
| miR-18 | B, T, Monocyte | (CTATCTGCACTAGATGCACCTTA)$_2$ | identical | 12 |
| 181a | B | (ACTCACCGACAGCGTTGAATGTT)$_2$ | identical | 13 |
| miR-19a | B, T, Monocyte | (TCAGTTTTGCATAGATTTGCACA)$_2$ | identical | 14 |
| miR-19b | B, T, Monocyte | (TCAGTTTTGCATGGATTTGCACA)$_2$ | identical | 15 |

TABLE 1 -continued

Sequences of miRNA binding sites.

| miRNA | cell types miRNA is enriched in | binding site sequence | mouse vs. human similarity | SEQ IDs |
|---|---|---|---|---|
| miR-20 | B, T, Monocyte | (CTACCTGCACTATAAGCACTTTA)$_2$ | identical | 16 |
| miR-21a | B, Monocyte, MF | (TCAACATCAGTCTGATAAGCTA)$_2$ | identical | 17 |
| miR-223 | Myeloid | (TGGGGTATTTGACAAACTGACA)$_2$ | identical | 18 |
| miR-24-3p | DC | (CTGTTCCTGCTGAACTGAGCCA)$_2$ | identical | 19 |
| miR-29a | T | (TAACCGATTTCAGATGGTGCTA)$_2$ | identical | 20 |
| miR-29b | T | (AACACTGATTTCAAATGGTGCTA)$_2$ | identical | 21 |
| miR-29c | T | (TAACCGATTTCAAATGGTGCTA)$_2$ | identical | 22 |
| miR-302a-3p | MF | (TCACCAAAACATGGAAGCACTTA)$_2$ | identical | 23 |
| miR-30b | DC | (AGCTGAGTGTAGGATGTTTACA)$_2$ | identical | 24 |
| miR-33-5p | MF | (TGCAATGCAACTACAATGCAC)$_2$ | identical | 25 |
| miR-34a | B, DC | (ACAACCAGCTAAGACACTGCCA)$_2$ | identical | 26 |
| miR-424 | Monocyte | (TTCAAAACATGAATTGCTGCTG)$_2$ | 21st base G to A in human | 27 |
| 652-3p | DC | (AATGGCGCCACTAGGGTTGTG)$_2$ | identical | 28 |
| miR-652-5p | DC | (GAATGGCACCCCCTCCTAGGGTTG)$_2$ | 13th base G to A in humans; extra U at 3' end in humans | 29 |
| miR-9-3p | MF | (ACTTTCGGTTATCTAGCTTTAT)$_2$ | identical | 30 |
| miR-9-5p | MF | (TCATACAGCTAGATAACCAAAGA)$_2$ | identical | 31 |
| miR-92a | B, T, Monocyte | (CAGGCCGGGACAAGTGCAATA)$_2$ | Extra U in human 3 end | 32 |
| miR-99b-5p | MF, DC | (CGCAAGGTCGGTTCTACGGGTG)$_2$ | identical | 33 |

Example 2: In Vivo Testing of AAV-miRNA Binding Site Constructs

AAV vectors containing OVA with and without individual and combinatorial miRNA binding sites were injected into mice intramuscularly. In brief, C57BL/6 male mice at 6 to 8 weeks old were injected by intramuscular injection at 6.8E10 vg/mouse of indicated rAAV vectors. The rAAV vectors included miR-142BS, miR-223BS, miR-652-5pBS, miR-142BS+miR-223BS, and miR-142BS+miR-652BS. Blood was collected on a weekly basis for four weeks. Circulating OVA and anti-OVA were examined by ELISA.

The function of miR-223-3p and miR-652-5p binding sites in vivo was assessed. The rAAV-OVA expression cassettes were packaged into AAV1 capsids with or without the individual miR-223-3p or miR-652-5p binding sites, or in combination with miR-142BS elements. Produced vectors were then injected into TA muscles of adult mice. Mice administered with rAAV1 empty capsids or PBS (mock) were used as controls.

Figure 4A:
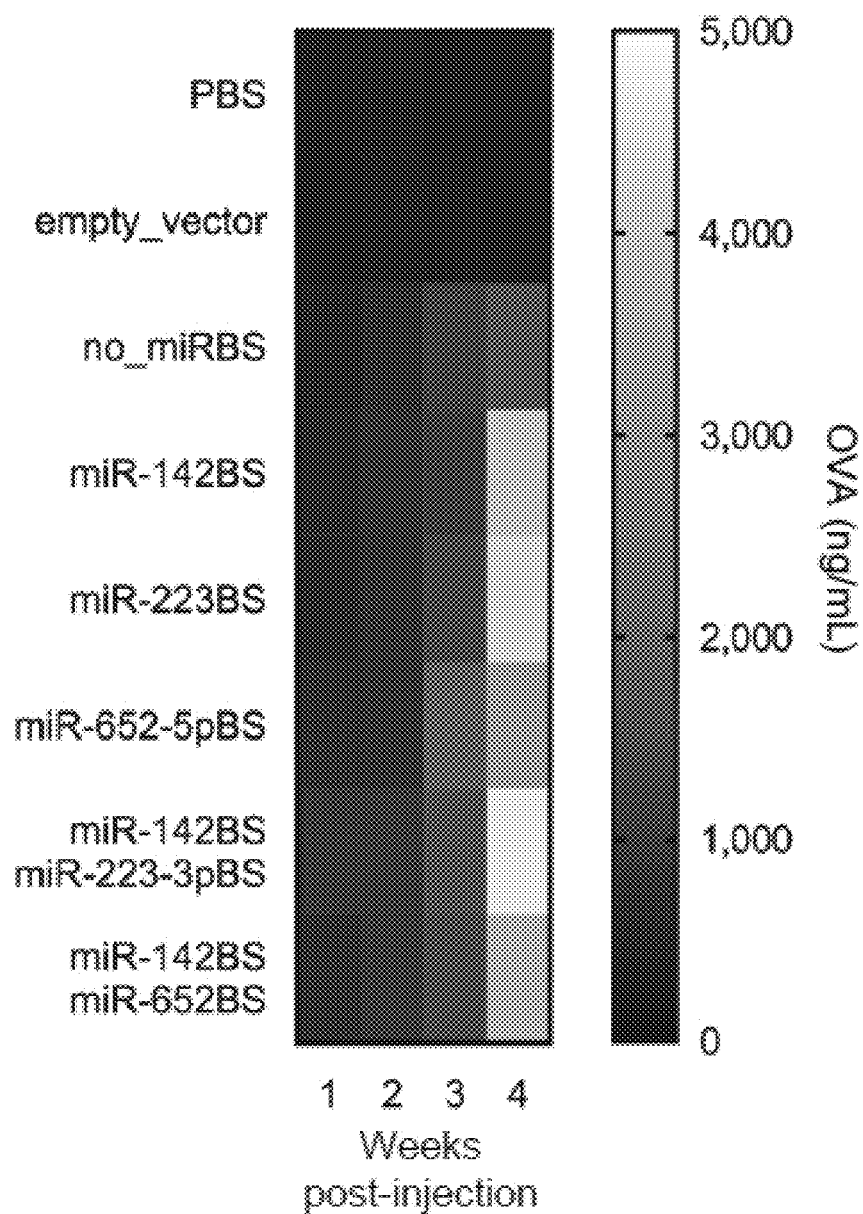
FIGS. 4A-4B show in vivo performances of novel individual and combinatorial miRBS cassette designs in rAAV vectors. C57BL/6 male mice at 6 to 8 weeks old were injected by intramuscular injection at 6.8E10 vg/mouse of indicated rAAV vectors. Blood was collected on a weekly basis for four weeks and measured for circulating OVA (FIG. 4A) and anti-OVA IgG (FIG. 4B) by ELISA. Heatmap values represent means (n=10 per group).
Figure 4B:
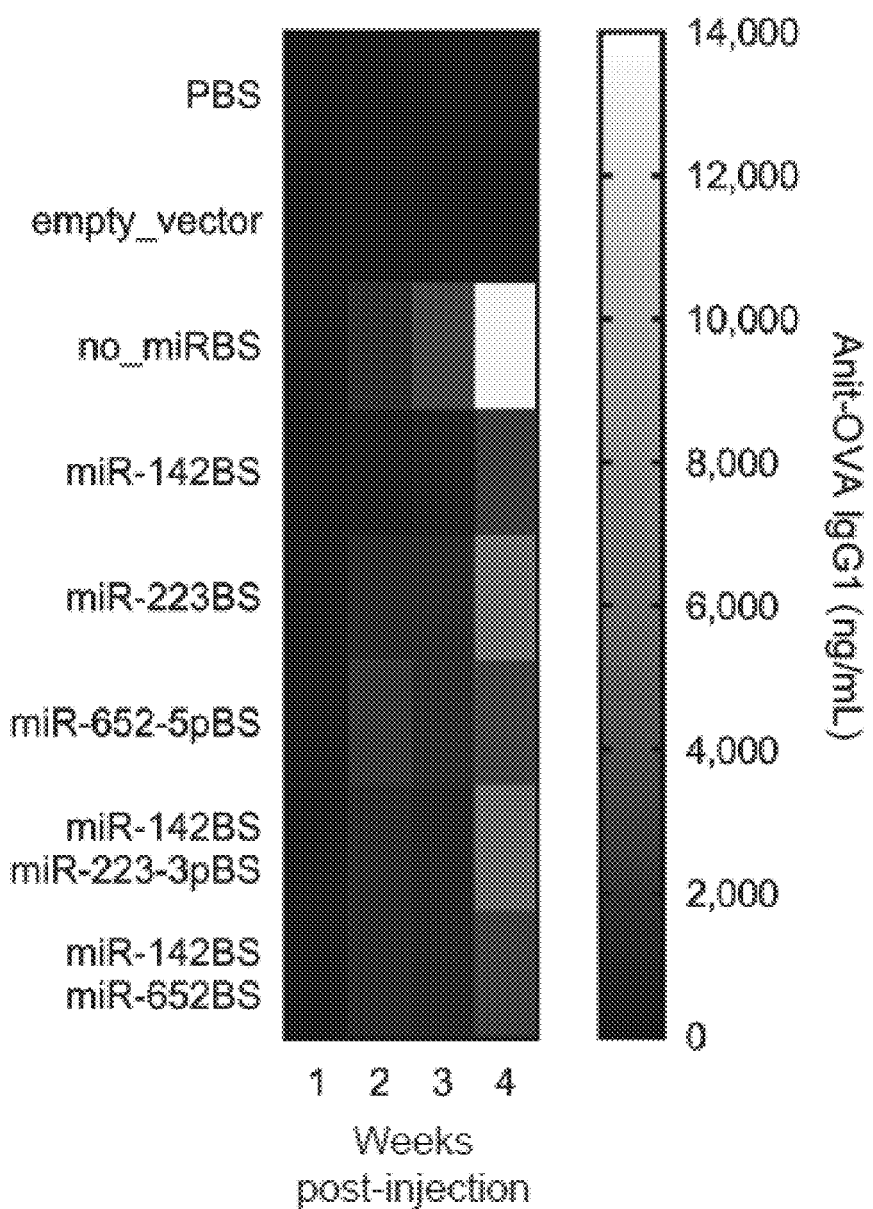
Figure 7A:
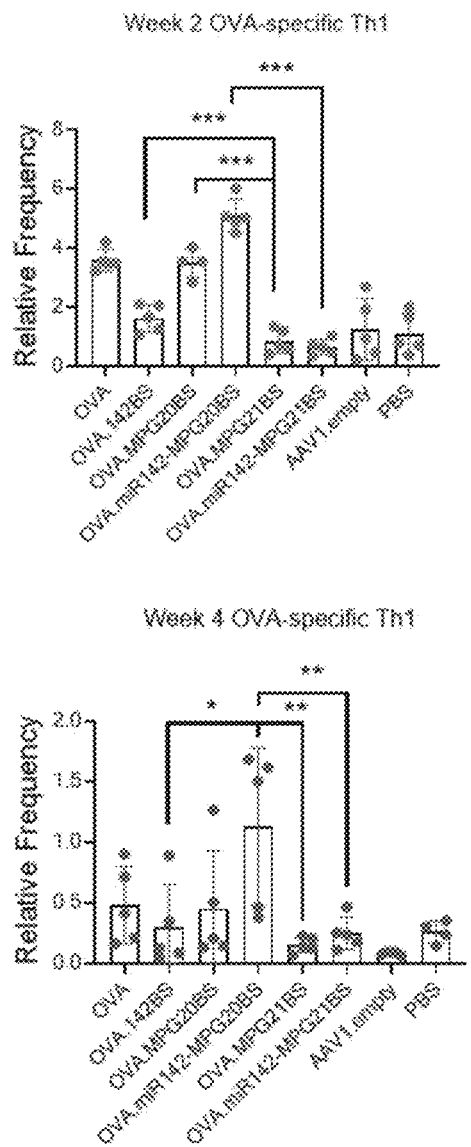
FIGS. 7A-7F show cytokine secretion from OVA-stimulated splenoyctes. In vivo response to novel individual and combinatorial miR-BS cassette designs in rAAV-OVA expression vectors.
Figure 7B:
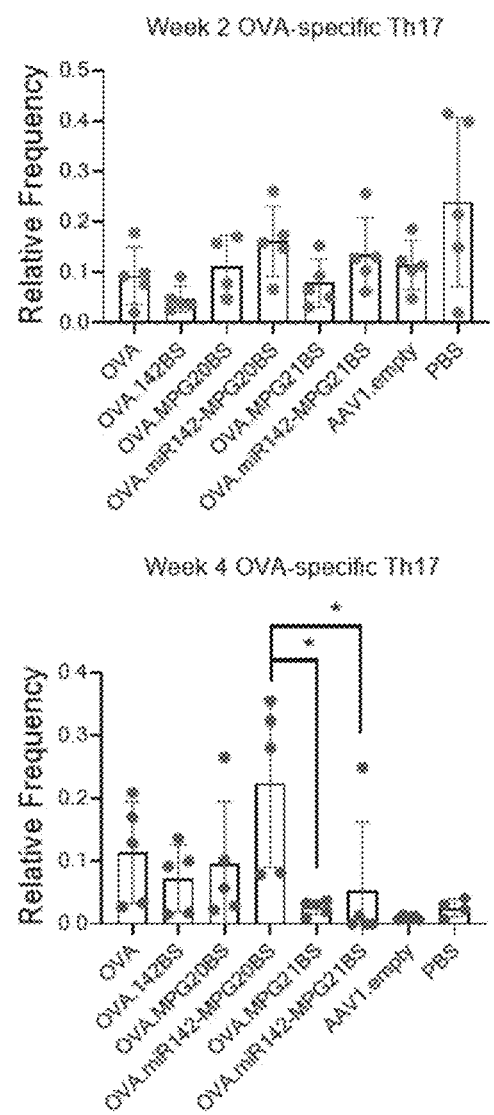
Figure 7C:
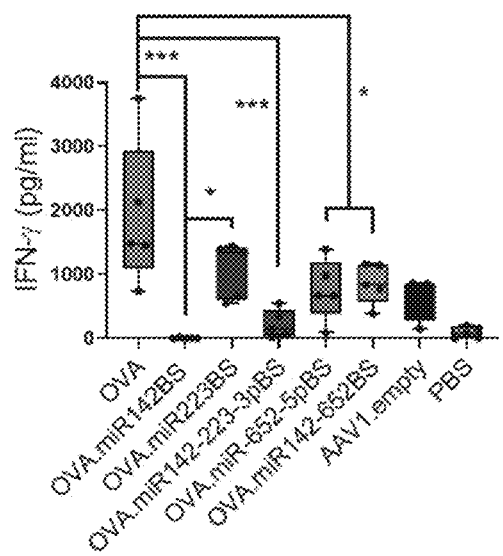
Figure 7D:
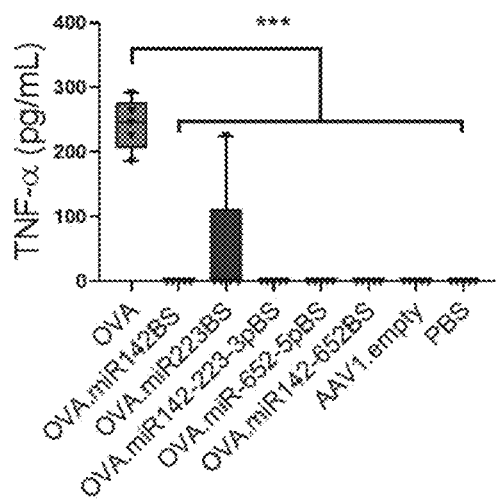
Figure 7E:
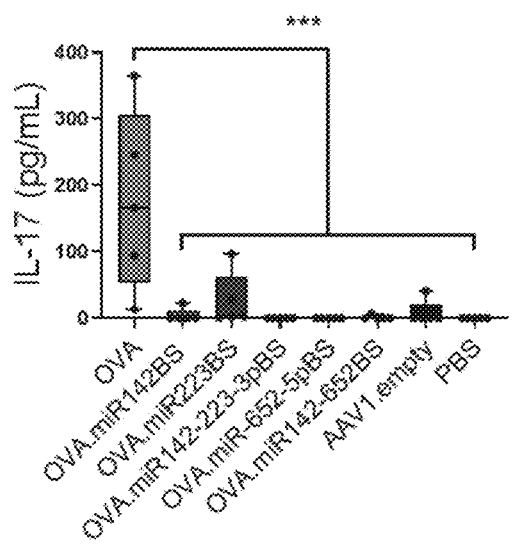
Figure 7F:
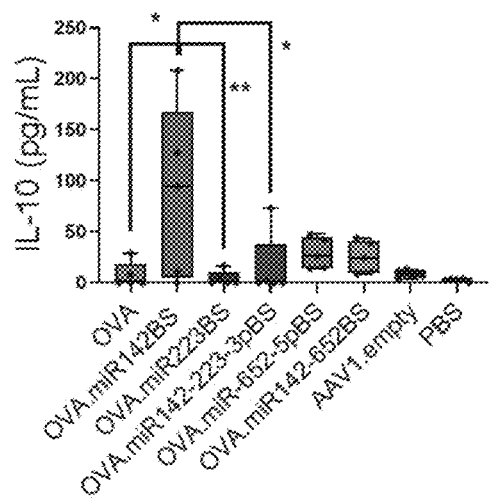
Figures 9A, 9B, 9C:
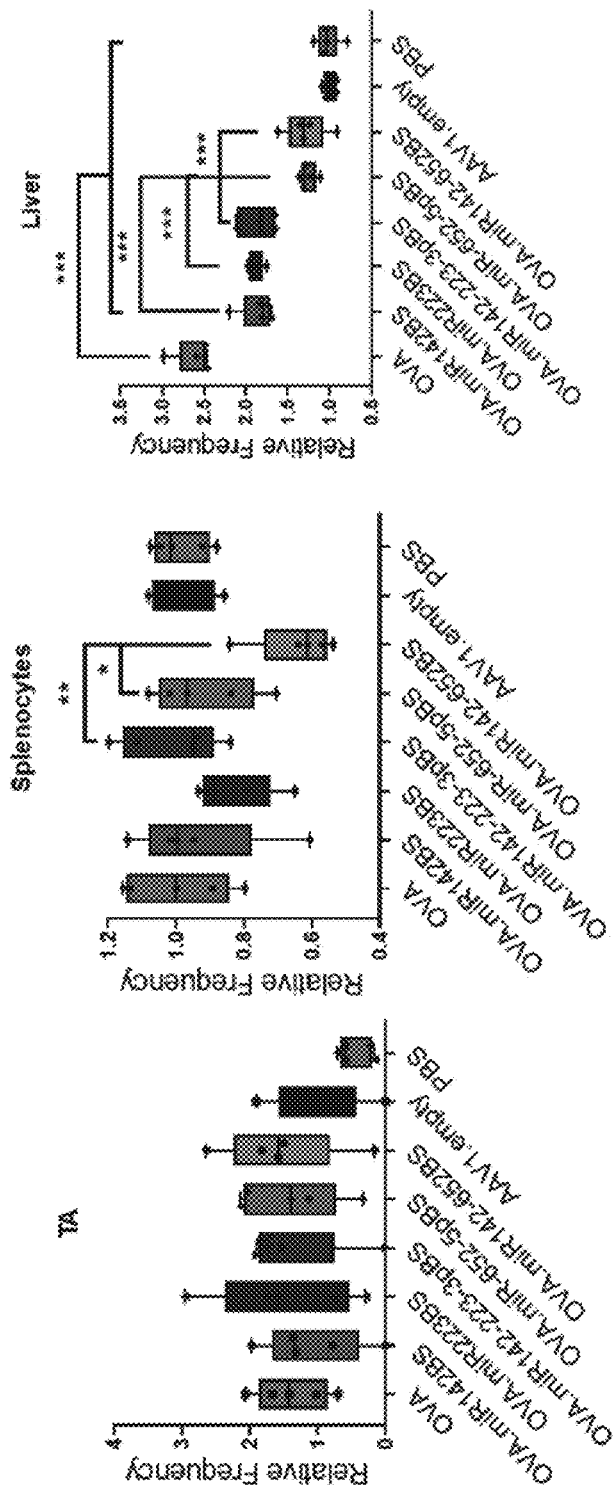
FIGS. 9A-9C show dendritic cell population in TA (FIG. 9A), splenocytes (FIG. 9B), and liver (FIG. 9C) at four weeks post-injection.
Figure 10:
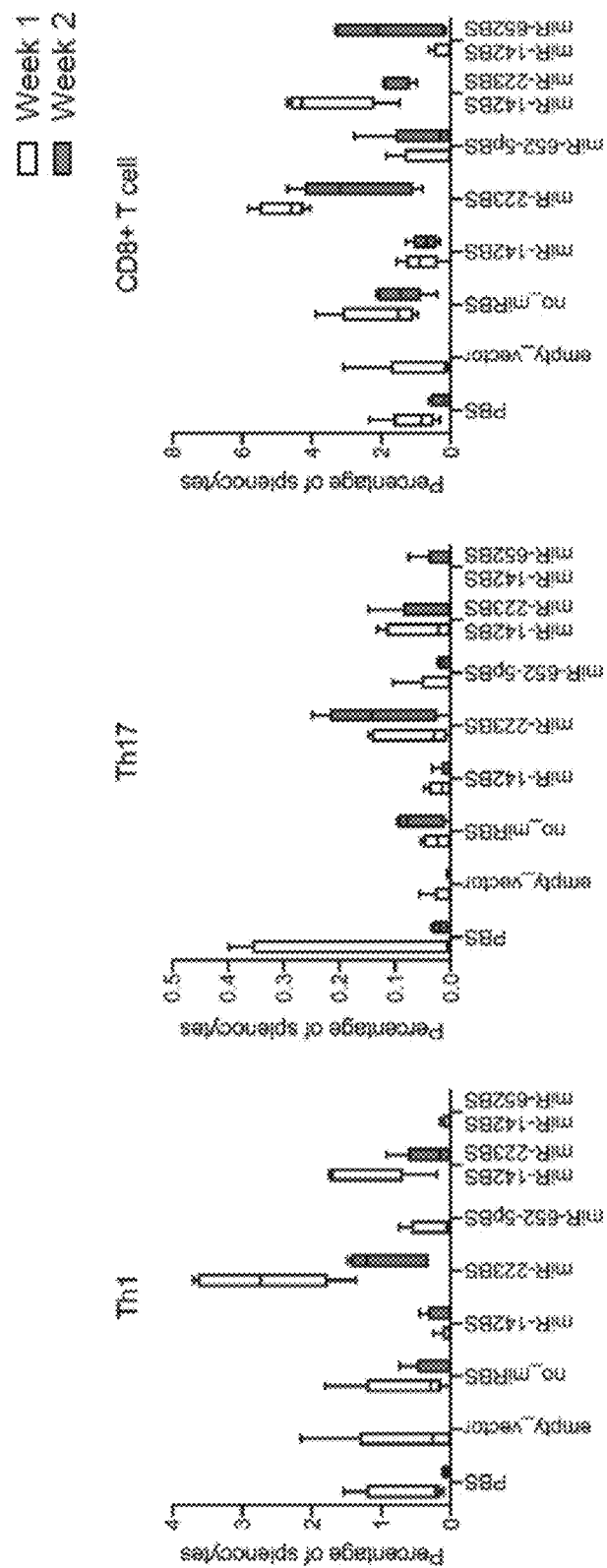
FIG. 10 shows in vivo response to novel individual and combinatorial miRBS cassette designs in rAAV OVA expression vectors. C57BL/6 male mice at 6- to 8-weeks old were injected by intramuscular injection of rAAV-OVA expression vectors at 6.8E10 vg/mouse. Mice were sacrificed at 2- and 4-weeks post-injection and splenocytes were harvested. Cultured splenocytes were then stimulated with OVA and five hours post-stimulation cells were assayed for Th1, Th17, or CD8 expression by flow cytometry. Week 2 values (white) and week 4 values (gray) are displayed as box plots representing means±SD, whiskers=min and max values (n=5 per group).

When tested in vivo as rAAV vectors, the novel miR-BS cassettes led to high transduction efficacy of vectors at levels that are equal to the prior art (FIGS. 4A-4B). This result demonstrates that the novel miR-BS cassettes did not inhibit rAAV transduction and robust transgene expression.

Mouse tissues (injected TAs, liver, and spleen) two- and four weeks post-injection were isolated and subjected to cell dissociation and immunophenotyping by cell staining and flow cytometry to quantify the abundance of CD8+ T cells, CD4+ T cells, mature DCs, and macrophages. In respect to these analytes, the combination of miR-142BS+miR-652BS cassette conferred an equal or stronger reduction in transgene-specific immune response than the miR-142BS cassette at the site of injection (tibialis anterior) (FIGS. 5A-5E), in the spleen and in the liver at four weeks post-injection (FIGS. 6A-6E, 7A-7F, 8A-8E, 9A-9C, and 10). These data indicate that the novel combination miR-142BS+miR-652BS cassette mutes vector transgene-related immunogenicity. Additionally, ex vivo OVA stimulation of splenocytes isolated from mice treated by vectors also showed that the combination miR-142BS+miR-652BS cassette led to Th1 and Th17 responses that were equivalent to those conferred by the miR-142BS cassette.

Figure 11B:
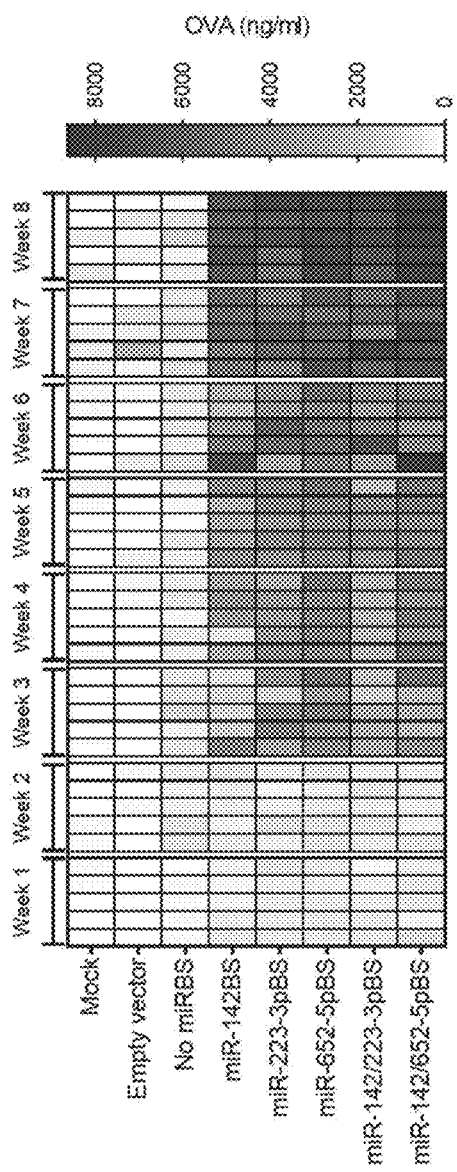
Figure 11C:
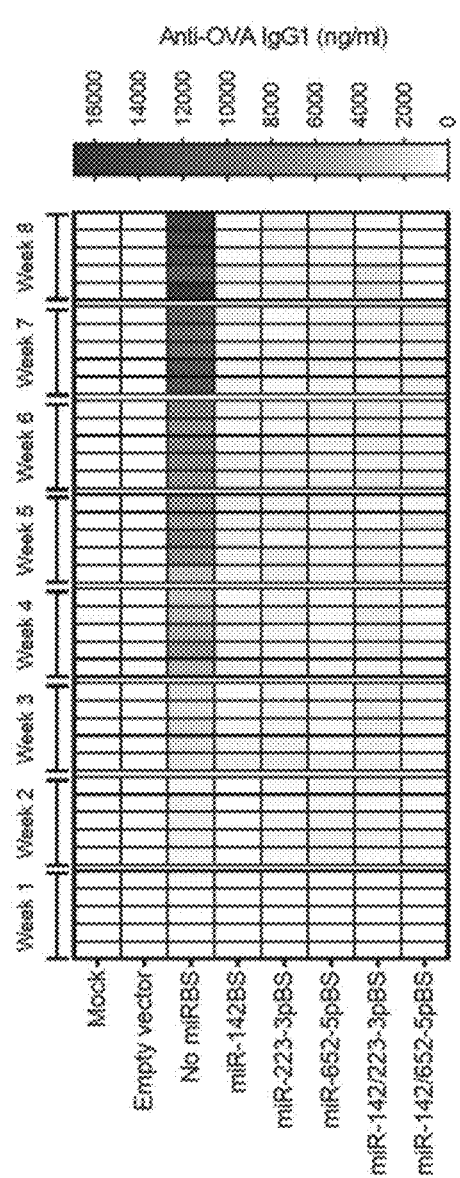
Figure 11F:
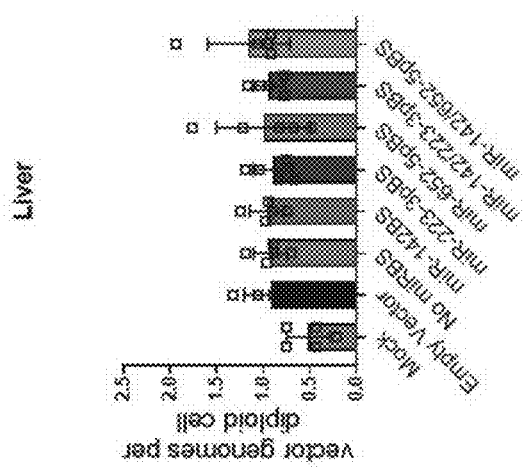
Figure 11E:
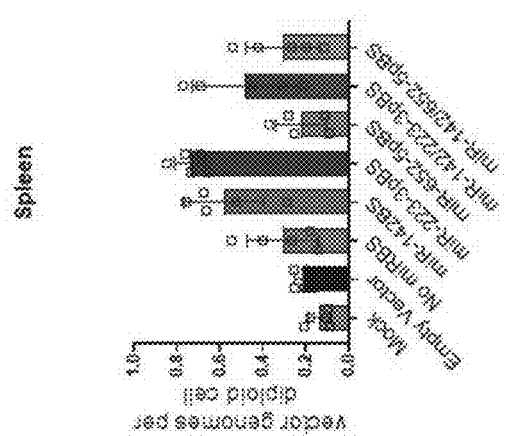
Figure 11D:
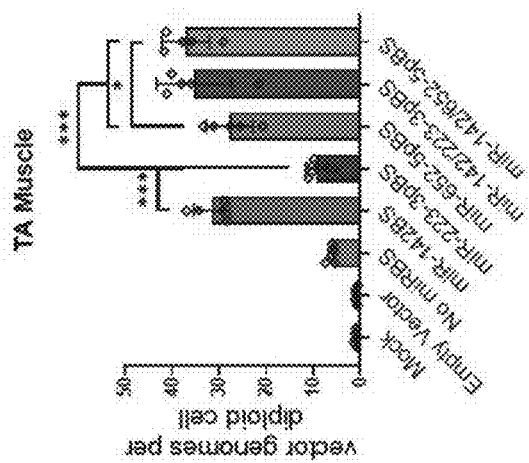
Figure 16A:
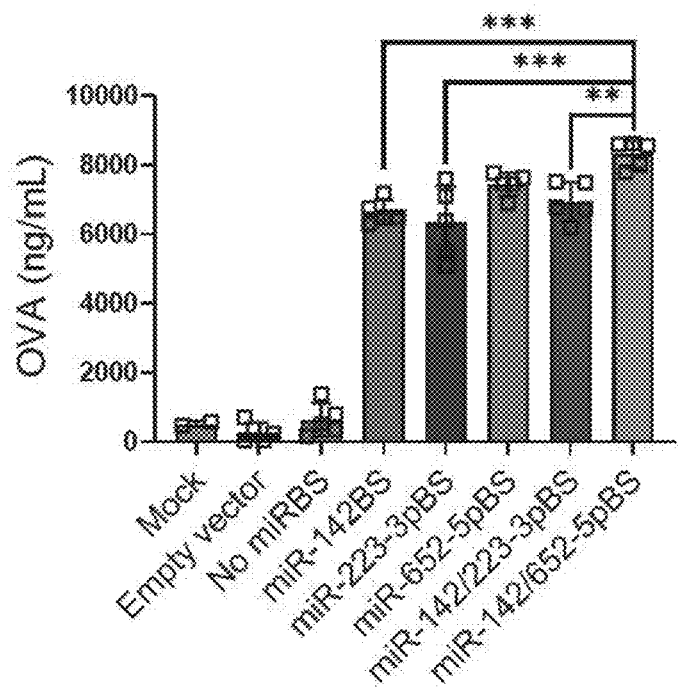
FIGS. 16A and 16B show that the miR-142/652-5pBS cassette was the most efficient at boosting OVA expression and achieved maximal suppression of anti-OVA antibody response. OVA (FIG. 16A) and anti-OVA IgG1 (FIG. 16B) levels in sera of mice eight weeks after rAAV1 injection were estimated by ELISA (mean±SD, n=5). p values were estimated by one-way ANOVA with Tukey's post hoc test. p<0.01, *p<0.001.
Figure 16B:
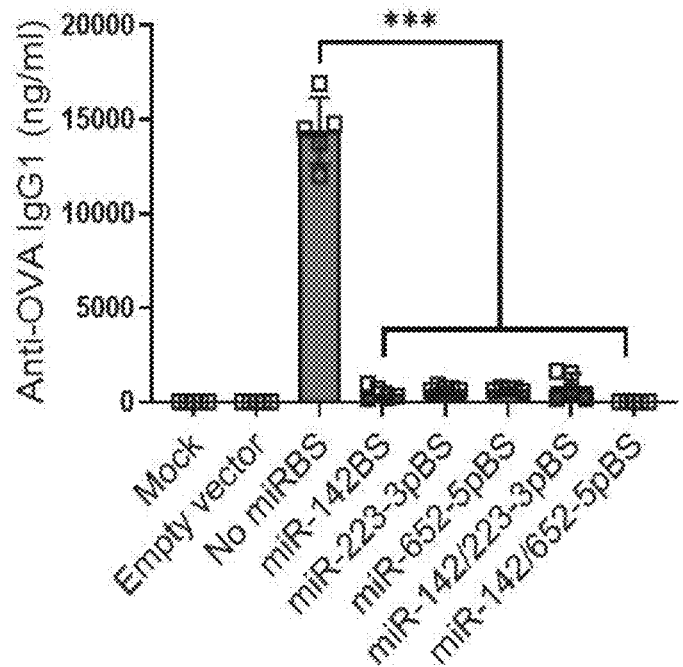

Animals injected with rAAV1.OVA.miR-BS vectors generated increasingly high and sustained levels of OVA expression in circulation, with a negligible anti-OVA antibody response (IgG1). In contrast, animals treated with rAAV1.OVA without miR-BSs showed baseline levels of OVA after eight weeks (FIGS. 11B and 11C). These animals also generated the highest levels of anti-OVA antibodies, which were substantially greater than the anti-OVA IgG levels produced in mice injected with rAAV1.OVA.miR-BS vectors (FIGS. 11B and 11C). The combination of miR-142 and 652-5p binding sites (miR-142/652-5pBS), or miR-652-5pBS alone, conferred the highest serum OVA levels. The differences in OVA expression levels between this combination and other miR-BS designs were most pronounced at eight weeks post-injection (p<0.001) (FIG. 16A). However, anti-OVA antibody production in mice injected with any of the miR-BS expressing vectors was not significantly different from each other, indicating that incorporation of any individual or combination of the tested miR-BSs led to similar levels of anti-transgene antibody suppression (FIG. 16B). With the exception of miR-223-3pBS, the levels of vector genomes detected in TAs eight weeks after injection were high (FIG. 11D). There was a greater than five-fold increase in the abundance of vector genomes in muscles treated with miR-BS-containing vectors, than in muscles treated with the rAAV-OVA construct that lacks miR-BSs (FIG. 11D). Consistent with immune clearance of transduced muscle fibers and loss of vector genomes, rAAV1.OVA.miR-142/652-5pBS-transduced muscle tissues showed at least a six-fold increase in vector genomes at eight weeks as compared to rAAV-OVA with no miR-BSs (FIG. 11D). FIGS. 11 E and 11F show that vector genome counts in the spleen and liver were at near background levels of detection.

In summary, these findings demonstrate that post-transcriptional regulation through the novel combinatorial miR-BS cassettes described here was a robust and improved method for overcoming transgene immunity towards secreted proteins, thereby improving the efficacy and safety of prophylactic and therapeutic gene delivery.

Example 3: miR-142135 and Other Novel miR-BS Designs Downregulate Macrophage Activation and Costimulatory Signals in DCs in Vivo It was hypothesized that any underlying immune responses against the vector and/or the transgene product might still preclude efficient OVA transduction, which may be overcome by optimizing APC detargeting. To test this, immune effector cell activation following vector treatment was analyzed. Mice injected intramuscularly with rAAV1 vectors with or without miR-BSs were sacrificed at four weeks post-injection and cells were isolated from injected TAs.

Without wishing to be bound by any theory, the antigen-specific T cell receptor (TCR) binds foreign peptide antigen-MHC complexes, and the CD28 receptor binds to B7 (CD80/CD86) costimulatory molecules expressed on the surface of APCs. This has been known as a process that is vital to initiating and maintaining the proliferation of T cells. Immunophenotyping of isolated cells by flow cytometry revealed an overall depletion of macrophages and CD80/CD86-positive DCs (CD11c+ cells) in mice injected with vectors carrying miR-BS at the four-week time point (FIGS. 12A and 12E). The greatest repression was achieved with vectors harboring the miR-652-5pBS or miR-142/652-5pBS cassettes. A substantial decrease in overall activated DCs in TA muscles across different vectors was observed.

Lymph nodes have been known as secondary lymphoid organs where different immune cell populations coordinate both the innate and adaptive arms of the immune response. Therefore, the number of CD80/CD86-positive DCs in draining lymph nodes of the injected limb at two and four weeks post-injection was also determined. A significant reduction in the population of activated macrophages, CD80/CD86-positive DCs in the animals treated with vectors carrying miR-BSs was observed (FIGS. 12B, 12F, 17B, and 18A-18C). However, the suppression in macrophage and DC activation did not significantly vary among the different miR-BS designs.

Figure 17C:
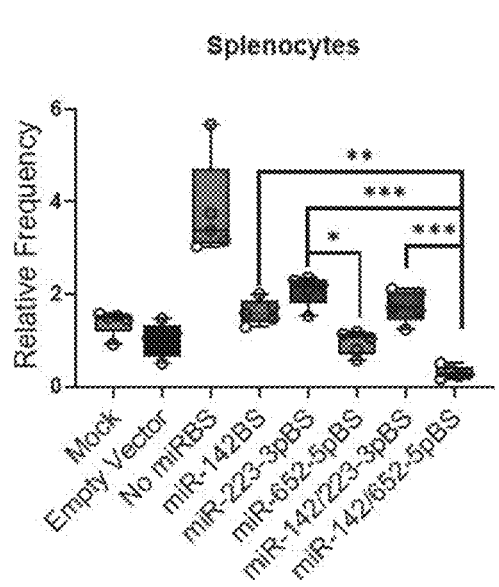
Figure 19A:
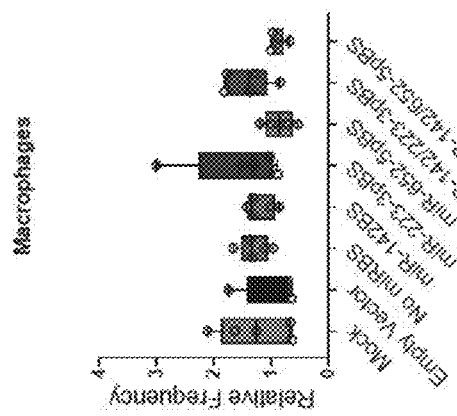
Figure 19B:
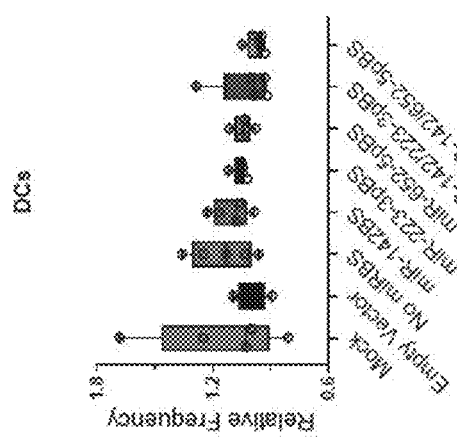
Figure 19C:
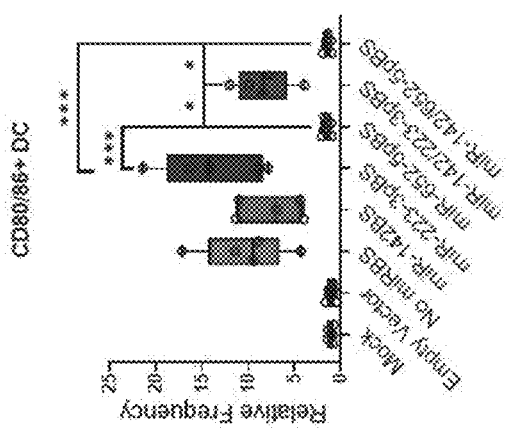
Figure 19D:
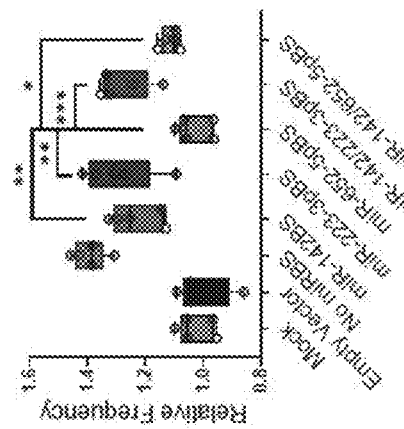
Figure 19E:
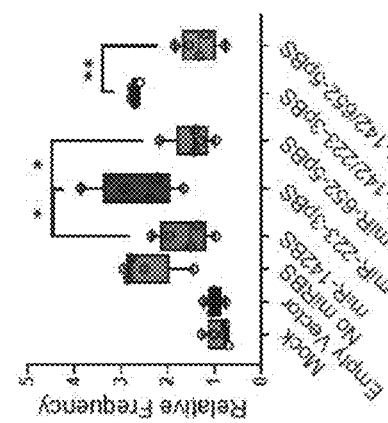
Figure 19F:
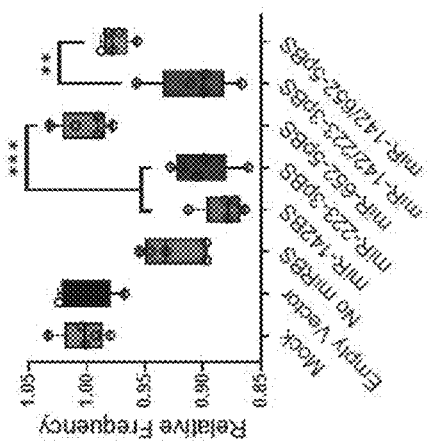

The inventors of the instant application have demonstrated that miR-142BS-mediated APC detargeting leads to a reduction of co-stimulatory molecule expression in isolated splenocytes. To further confirm this effect, splenocytes from injected mice were isolated and stained them for macrophage, DC, and DC co-stimulatory markers. All miR-BS-containing vectors significantly suppressed DC activation, macrophage activation, and CD80/86-positive DCs in splenocytes (FIGS. 12C, 12G and 17C). While most miR-BS designs mediated weak suppression at two weeks post-injection, indicating no change in the activation state of macrophages and DCs, miR-142BS-, miR-652-5pBS-, and miR-142/652-5pBS-containing vectors inhibited CD80/86 expression as early as two weeks following administration (FIGS. 19A-19C).

Figure 17D:
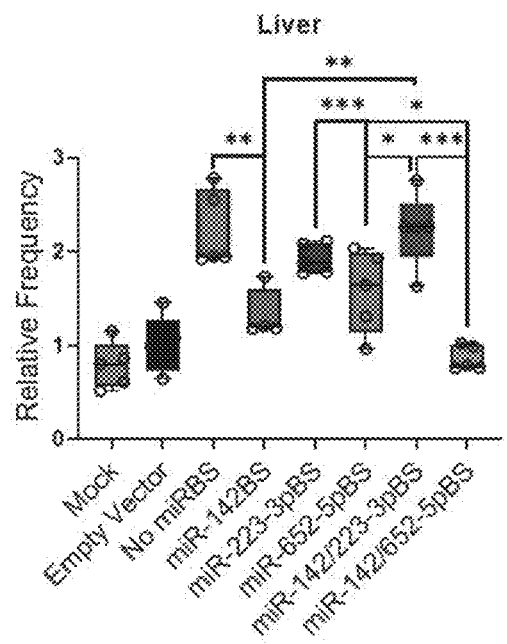

Immune cells from the livers of injected mice were also isolated and it was found that miR-142/652-5pBS-containing vectors mediated the strongest reduction of activated macrophages, DCs, and CD80/86-positive DCs (FIGS. 12D, 12H and 17D).

Additionally, to determine the activation status of circulating immune cells, peripheral blood lymphocytes (PBLs) isolated from the blood of treated mice four weeks post-injection were immunophenotyped. No differences in the levels of activated macrophages, DCs, and CD80/86-positive DCs in the presence of miR-BSs were observed (FIGS. 20A-20C), indicating that immune cell activation occurred within different tissue compartments, not systemically.

Example 4: miR-BS-Mediated APC Detargeting Downregulates OVA-Specific T Cell Activation In Vivo It has been previously established by the inventors of the instant application that miR-142BS-mediated APC detargeting achieves circumvention of adaptive immunity by blunting OVA-specific CD8+ T cell response, resulting in sustained transgene expression. To assay the ability of rAAV1.OVA-miR-BS vectors to engage the adaptive immune response, recruitment of CD4+ and CD8+ T cells was measured four weeks following vector administration in the injected TA muscles, lymph nodes proximal to the injection site, the spleen, and the liver. Analyses of the overall CD8+ T cell populations showed that all of the tested miR-BS designs significantly repressed CD8+ T cell response to the vector in all tissues (FIGS. 13A-13D).

Although CD8+ T cell responses in tissues were significantly repressed with groups treated with vectors harboring miR-BS cassettes, they were not indicative of the transgene-specific CD8+ T cell activation status. Therefore, potential reduction in CD8+ T cell response specific to OVA protein was assessed. The ovalbumin SIINFEKL (SEQ ID NO: 46) peptide fragment was recognized by the MHC class I molecule (H-2Kb) of T cells in mice. Therefore, OVA-specific CD8+ T cells could be identified by staining cells with H-2Kb/SIINFEKL (SEQ ID NO: 46) MHC Tetramers and quantified by flow cytometry. At four weeks post-injection, the levels of activated OVA-specific CD8+ T cells were reduced by all miR-BS designs. Vectors carrying miR-652-5pBS and miR-142/652-5pBS appeared to confer the strongest reduction (FIGS. 13E-13H). The extent of reduction in lymph nodes and splenocytes were nearly equal to those conferred by PBS and empty capsid treatments.

Figure 13A:
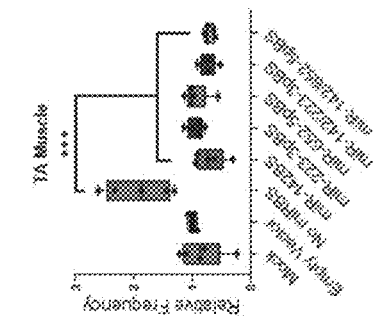
FIGS. 13A-13H show that miR-142BS-, miR-223BS-, and miR-652BS-mediated detargeting suppressed OVA specific CD8 T cell response. C57BL/6 male mice, six weeks old, were intramuscularly (i.m.) injected with mock, empty capsid, or rAAV1.OVA vectors with or without miR-BSs ($1 \times 10^{11}$ GCs/mouse). Mice were sacrificed four weeks after treatment and cells were isolated from TAs, lymph nodes, spleens and livers. Cells were then stained for CD8 T cell markers or with anti-CD8a/H-2Kb SIINFEKL (SEQ ID NO: 46) tetramer and quantified by flow cytometry (n=5). Relative frequencies of CD8+ T cells (FIGS. 13A-13D) and OVA-specific CD8+ T cells (FIGS. 13E-13H) are depicted as box plots with means, first and third quartile boundaries, and whiskers indicating max and min values (n=5). p values were estimated by one-way ANOVA with Tukey's post hoc test. *p<0.05, p<0.01, *p<0.001
Figure 13B:
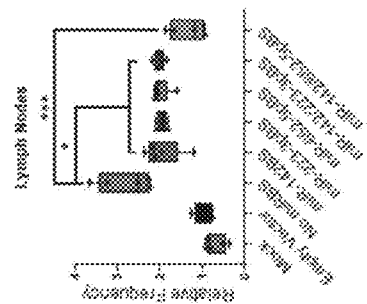
Figure 13C:
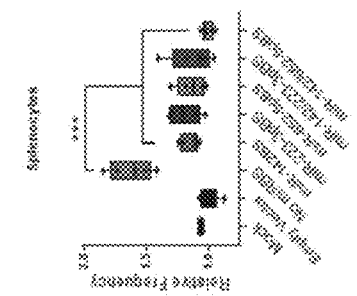
Figure 13D:
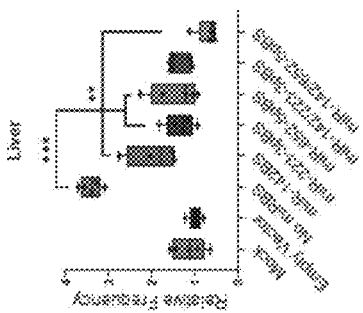
Figure 13E:
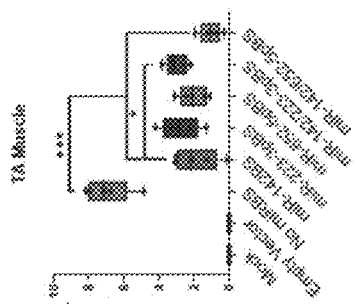
Figure 13F:
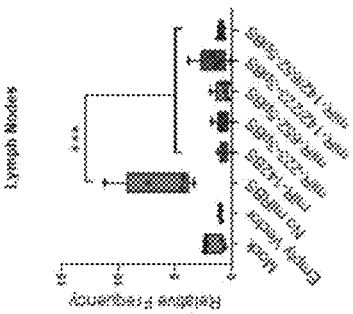
Figure 13G:
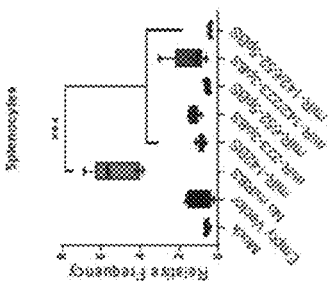
Figure 13H:
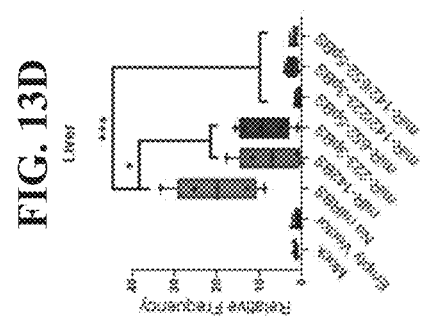
Figure 14A:
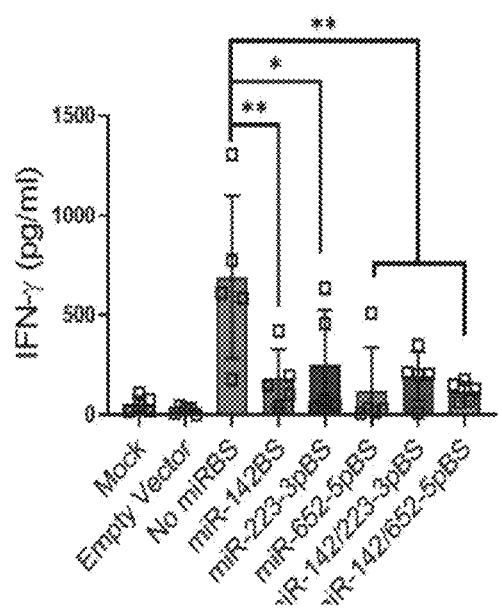
FIGS. 14A-14H show miR-BS incorporation diminishes transgene-specific Th1 and Th17 inflammatory responses.
Figure 14B:
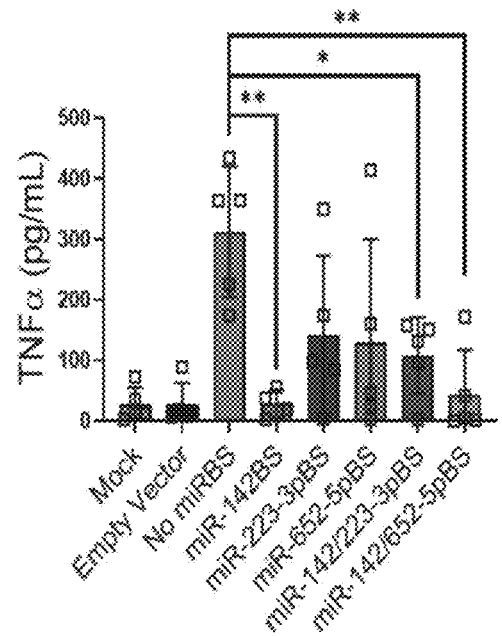
Figure 18C:
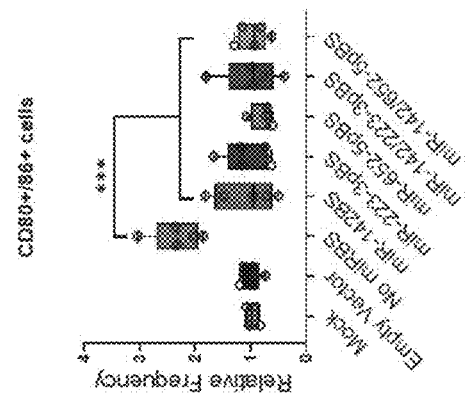
Figure 18F:
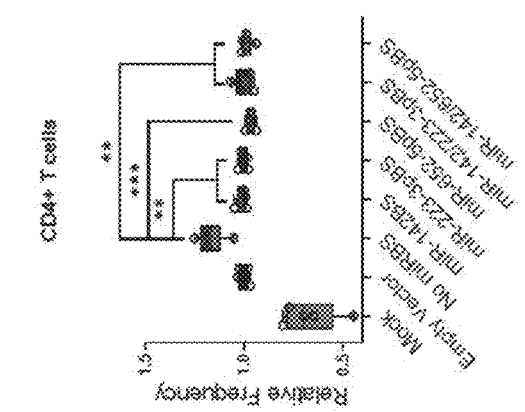
Figure 18B:
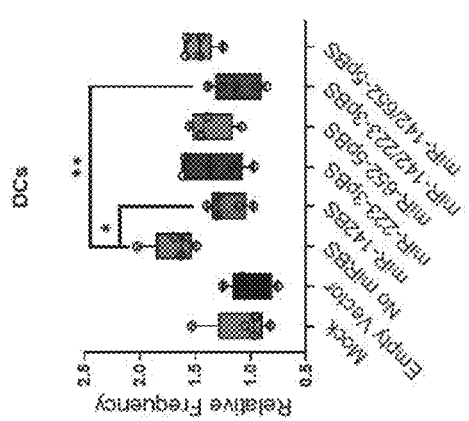
Figure 18E:
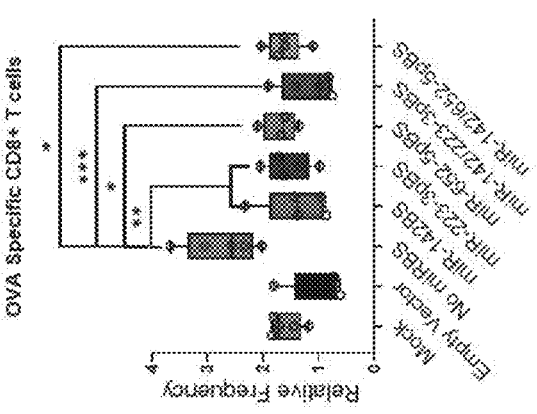
Figure 18A:
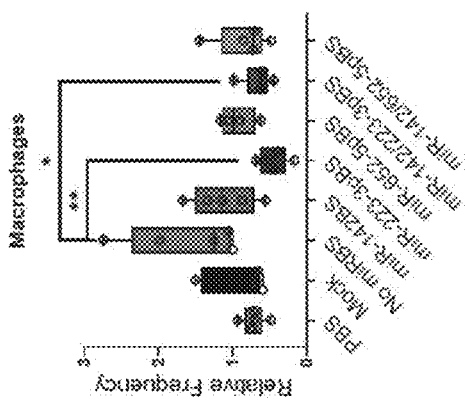
Figure 18D:
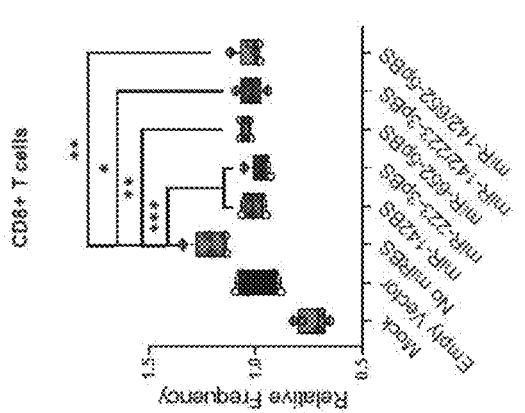

The miR-142BS and miR-223-3pBS cassettes were not as sufficient as other miR-BS designs in reducing OVA-specific CD8+ T cell responses in the liver (FIG. 13H). Furthermore, reduced activation of CD8+ T cells and OVA-specific CD8+ T cells was observed in lymph nodes and spleens as early as two weeks post-injection (FIGS. 18D, 18E, 19D, and 19E), but not in TA muscle and liver. Significant differences in OVA-specific CD8+ T cells were not observed between the different miR-BS combinations, except in lymph nodes at two weeks post-injection (FIG. 18E). Immunophenotyping of PBLs at four weeks post-injection revealed a significant reduction in circulating OVA-specific CD8+ T cells, but not overall CD8+ T cells for vectors containing miR-652-5pBS, miR-142/223-3pBS, and miR-142/652-5pBS combinations as compared to the vector without miR-BSs (FIGS. 14A and 14B).

Figure 21A:
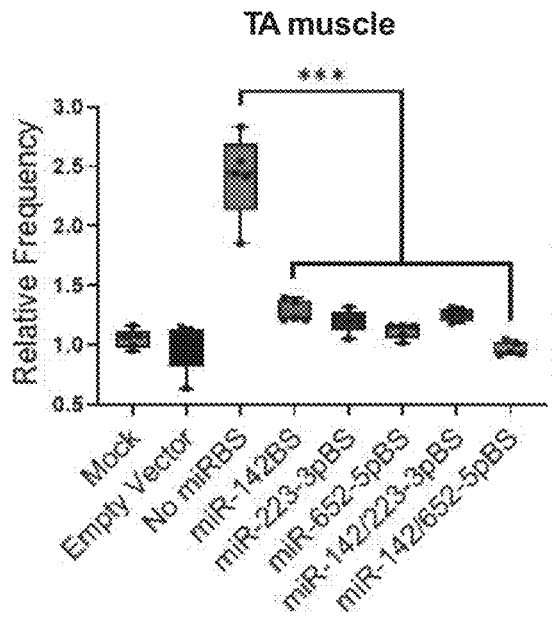
Figure 21B:
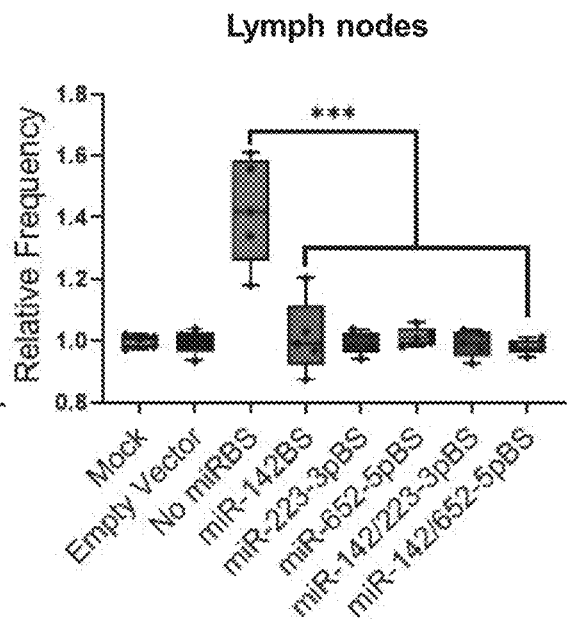
Figure 21C:
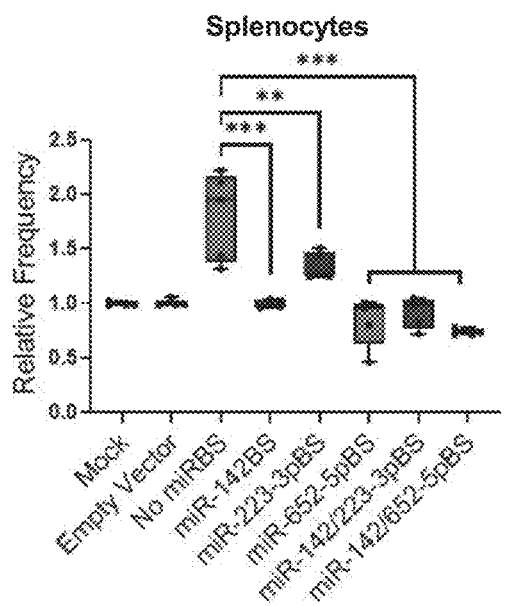
Figure 21D:
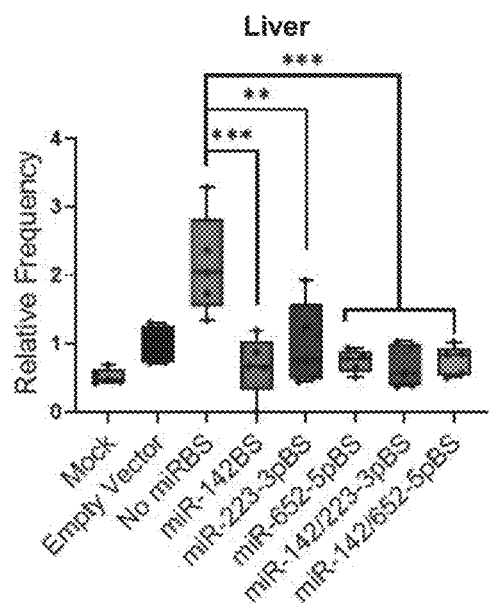
Figure 22A:
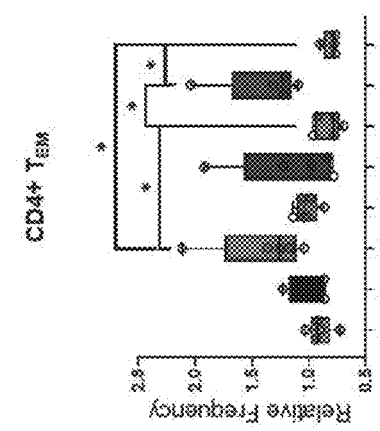
Figure 22D:
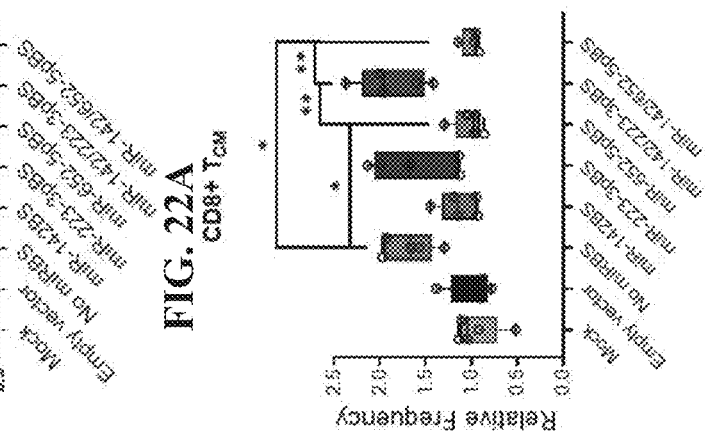
Figure 22B:
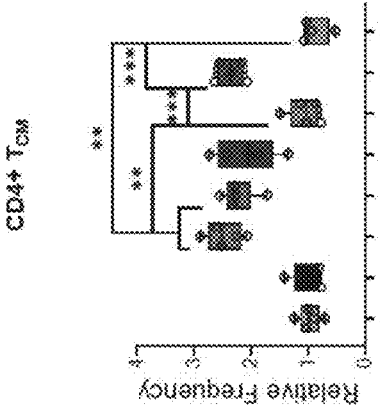
Figure 22E:
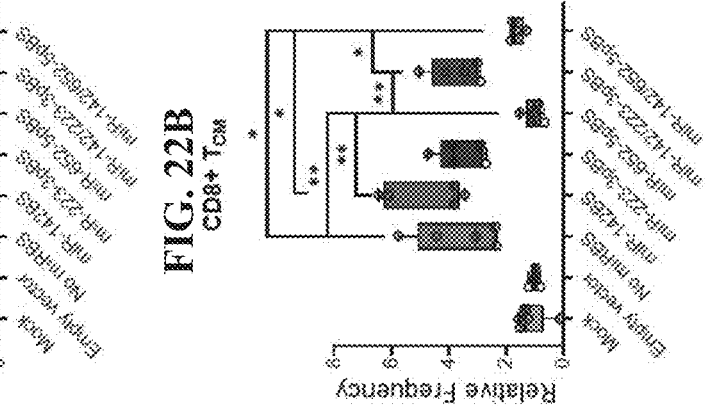
Figure 22C:
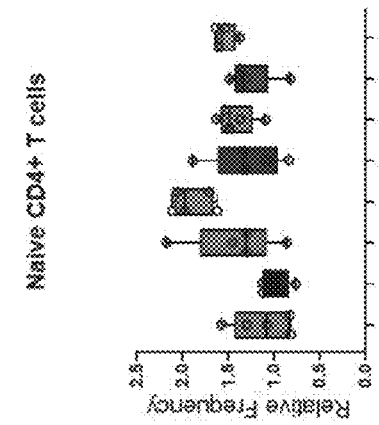
Figure 22F:
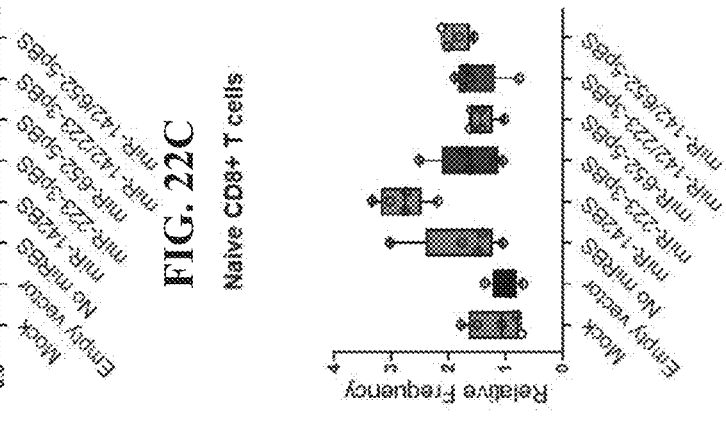

Next, the effect of vector injection on the CD4+ T cell population was tested. A significant reduction in CD4+ T cell counts was observed in the injected TAs across all vectors containing miR-BSs. Consistent with other cell types, miR-652-5pBS and miR-142/652-5pBS cassettes were the most efficient in suppressing CD4+ T cell activation (FIG. 21A). A similar decrease in CD4+ T cell numbers was also observed in lymph nodes, the spleen, and the liver (FIGS. 21B-21D). An overall reduction in the CD4+ T cell population in PBLs was also seen in treatment groups receiving vectors containing any combination of miR-BSs with no notable differences when compared to each other (FIG. 20C). Taken together, incorporation of miR-652-5pBS in the rAAV expression cassette mediated efficient suppression of macrophage, DC, CD4+, and CD8+ T cell activation and a decrease in the expression of co-stimulatory markers. In certain cases, this effect was enhanced when miR-652-5pBS was combined with miR-142BS.

Figure 14C:
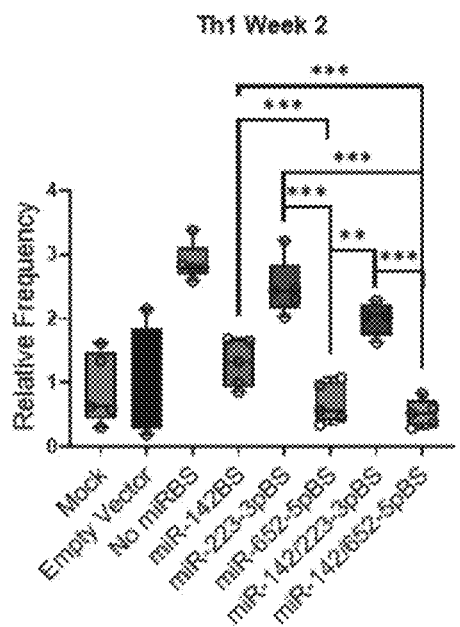
Figure 14D:
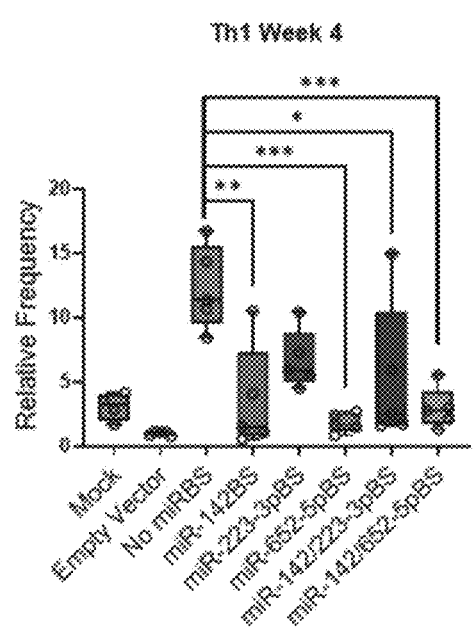

Example 5: miRBS-Mediated APC Detargeting Downregulates OVA-Specific Th1 Response, Inflammatory Cytokine Production, and Memory T Cells In Vivo It has been shown previously that TNF-α and IFN-γ are two principal pro-inflammatory cytokines produced in response to rAAV transduction. Without wishing to be bound by any theory, TNF-α is produced by DCs and other immune cells and is involved in both innate and adaptive immune responses. IFN-γ is the classic cytokine secreted by Th1 cells and promotes phagocytosis and upregulates microbial killing. Therefore, TNF-α and IFN-γ response to APC-detargeted vectors were determined. Splenocytes from mice that were injected with rAAV1.OVA vectors with or without miR-BSs at both two- and four-week timepoints were isolated and cultured. Upon OVA stimulation, splenocytes from mice treated with rAAV1.OVA with no binding sites secreted high levels of TNF-α and IFN-γ. In contrast, vectors carrying miR-BSs attenuated cytokine responses to levels that were on average greater than two-fold reduced, which was comparable to cytokines secreted by the splenocytes from mice that received PBS and empty capsids (FIGS. 14A and 14B). To further validate the suppression of Th1 response, the OVA stimulated splenocytes were stained for IFN-γ producing CD4 T cells and analyzed by flow cytometry. OVA-specific Th1 cell counts were high in rAAV1.OVA splenocytes as early as two weeks post-injection (FIGS. 14C and 14D). However, the reductions in the Th1 response became significant at two- and four-weeks post-injection only when miR-142BS, miR-652-5pBS, or both elements were incorporated into vectors. Splenocytes from rAAV1.OVA.miR-223-3pBS-treated mice showed no change at week 2 in IFN-γ-producing Th1 cells as compared to splenocytes from rAAV1.OVA-treated animals. Addition of miR-142BS to these vectors reduced responses to an extent at week 2 (FIG. 14C). miR-223-3pBS-containing vectors (in combination with or without miR-142BS) appeared to completely suppress Th1 activation by week 4 (FIG. 14D). This may suggest a possibility that the suppression of immune cell activation mediated by miR-223-3pBS incorporation follows kinetics that are slower than those conferred by miR-652-5pBS-mediated suppression.

Figure 14E:
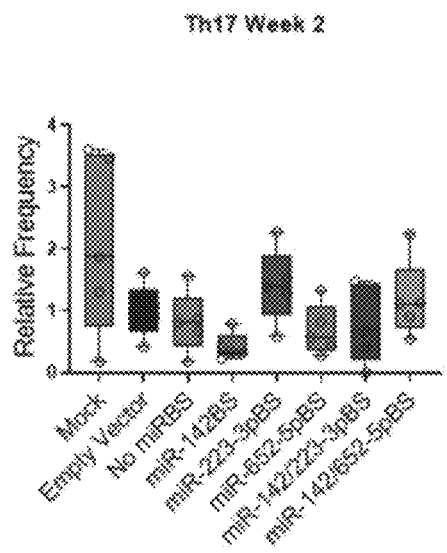
Figure 14F:
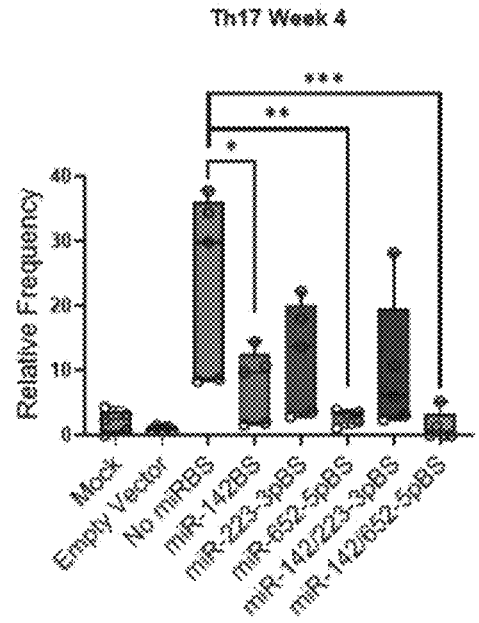
Figure 14G:
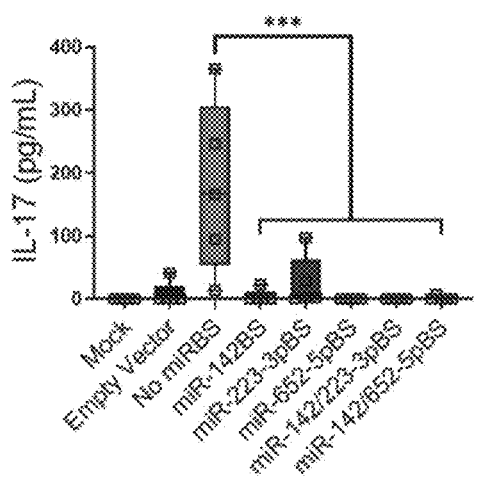
Figure 14H:
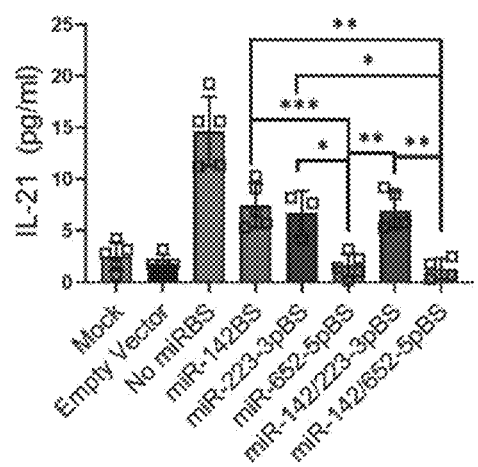

Example 6: The miR-142/652-5pBS Combination Effectively Suppresses Th17 Response In Vivo The pathway that is not well understood with respect to rAAV transgene immunogenicity is the involvement of Th17 cells. Th17 cells are a recently discovered cell type that secrete IL-17 as their primary effector cytokine and belong to the CD4+ T cell family. It was hypothesized that these pro-inflammatory cells might be involved in mounting an anti-transgene immune response. To investigate their contribution towards anti-transgene immunity, OVA-stimulated splenocytes at two- and four-weeks post-injection were quantified for IL-17A expressing CD4+ T cells by flow cytometry. While no OVA-specific Th17 response was observed at two weeks, rAAV1.OVA splenocytes showed elevation in the number of Th17 cells at four weeks (FIGS. 14E and 14F). With the exception of miR-223-3pBS, inclusion of the candidate miR-BSs in vectors significantly downregulated Th17 activation, with maximal repression imparted by miR-652-5pBS and miR-142/652-5pBS. This outcome was similar in fashion to Th1 responses under these treatments. Without wishing to be bound by any theory, both IL-17 and IL-21 are Th17 cell-secreted cytokines that accentuate the protective effects of Th17-mediated immune response. Therefore, Th17 activation was further confirmed by measuring IL-17 and IL-21 production from OVA-stimulated splenocytes. Consistent with the flow cytometry data, splenocytes from mice treated with rAAV1.OVA lacking miR-BSs produced high levels of IL-17. In contrast, vectors carrying miR-BSs conferred a significant reduction in Th17 activation, and hence a concomitant decrease in IL-17 production (FIG. 14G). Incorporation of miR-652-5pBS and miR-142/652-5pBS appeared to significantly suppress IL-21 secretion in stimulated splenocytes as well (FIG. 14H). Our data thus suggests that transgene-specific Th17 response might play a critical role in the suppression of transgene expression over time. Incorporation of miR-BSs in expression cassettes blunts this response, and in turn, boosts the levels of transgene expression.

Figure 23C:
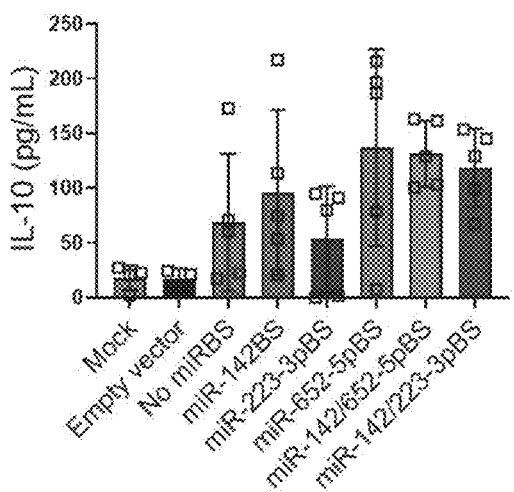
Figure 23D:
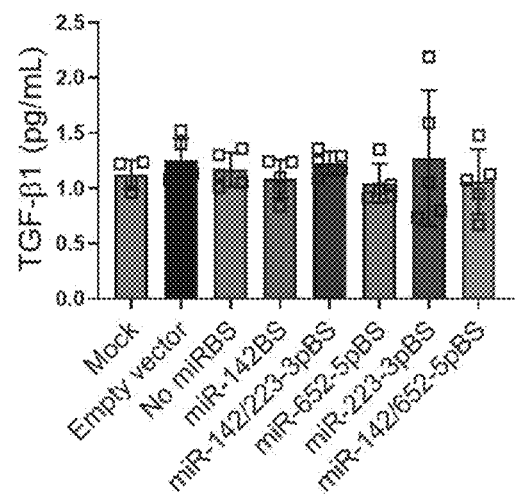

Example 7: miRNA-Mediated Detargeting does not Activate Regulatory T Cells to Enable Immunosuppression In Vivo The use of miR-142BS elements in lentiviral vectors induces immunologic tolerance and activates regulatory T cells (Tregs). To investigate if this effect was reproduced in rAAV-delivered transgenes containing miR-BSs, immune cells from TAs, lymph nodes, and spleens at two- and four-weeks post-injection were isolated and stained them for Treg-specific markers. The Treg population can be identified as CD4+ T cells that are also double-positive for CD25 and FOXP3. None of the miR-BS containing vectors led to an increase in the Treg cell numbers in any of the analyzed tissues (FIGS. 15A-15C and FIGS. 23A and 23B). Additionally, stimulated splenocytes from treated animals did not reveal any elevation of the anti-inflammatory cytokines IL-10 and TGF-β (FIGS. 23C and 23D). Therefore, the incorporation of miR-BSs into AAV vectors does not induce Treg activation nor induce tolerance by the suppression of other immune cell types as observed with lentiviral vectors.

Figure 15C:
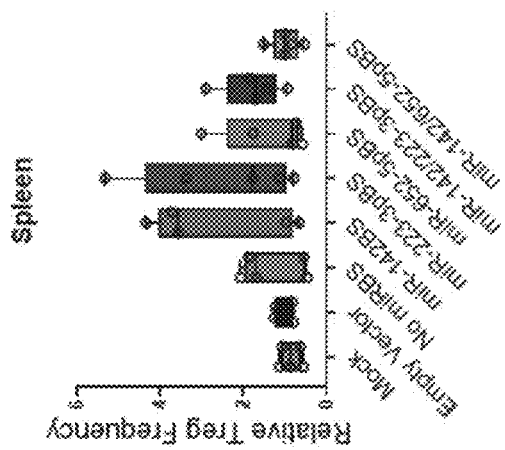
FIGS. 15A-15G show that miRNA-mediated detargeting acted independent of Treg immunosuppression and reduced tissue clearance by downregulation of OVA-specific CTL response.
Figure 15B:
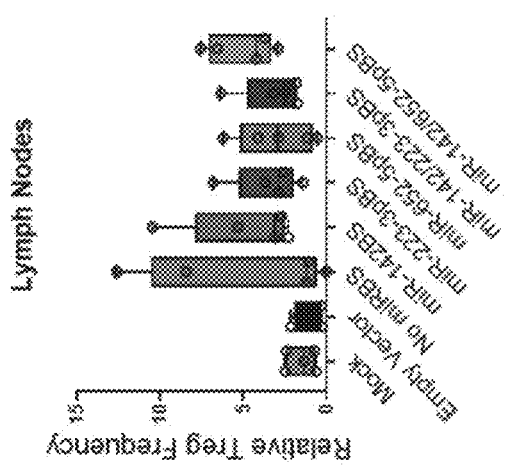
Figure 15A:
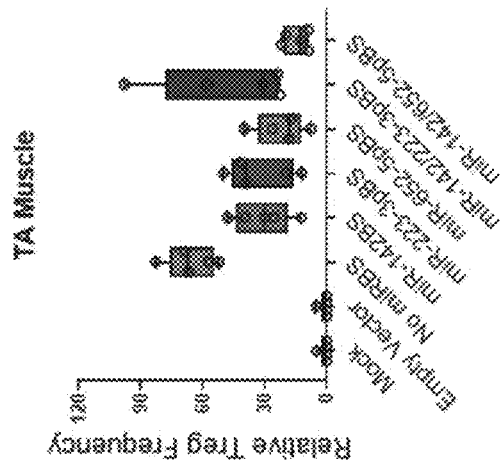
Figure 15D:
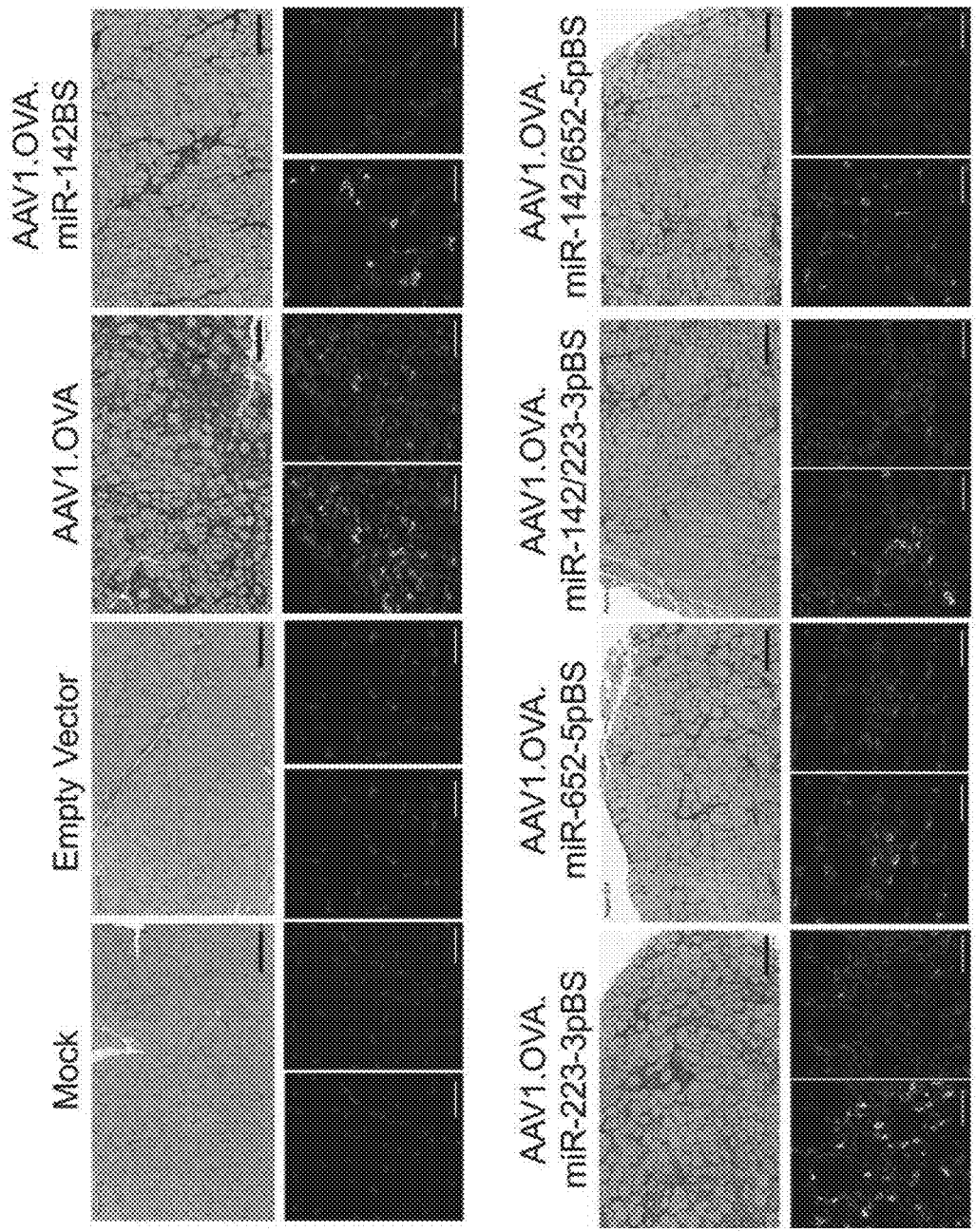
Figure 15G:
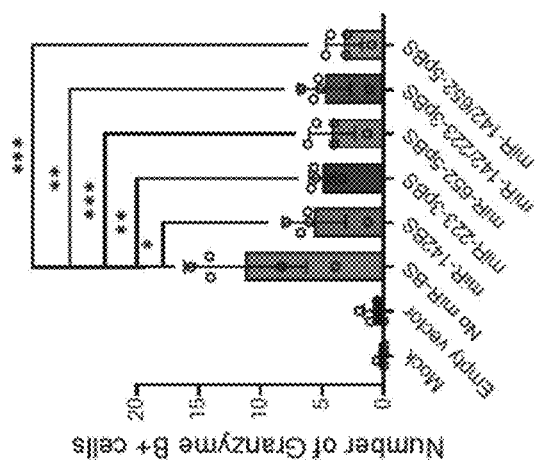
Figure 15F:
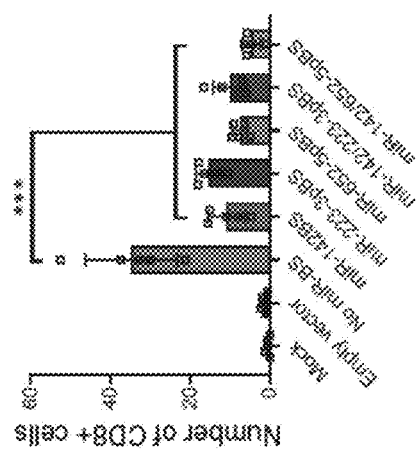
Figure 15E:
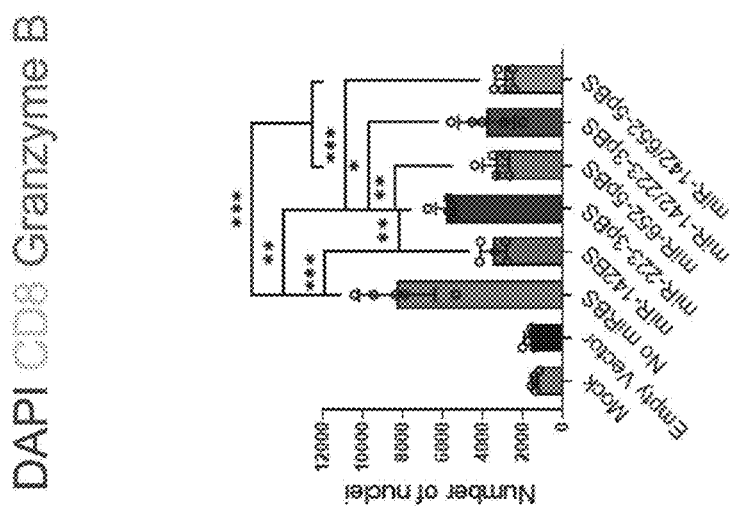

Example 8: miRBS-Mediated Suppression of CD8+ T Cell Response Reduces Clearance of Transduced Cells and Boosts Transgene Expression In Vivo It has been reported by the inventors of the instant application that inclusion of miR-142BS elements in the rAAV transgene cassette reduced infiltration of CD8+ T cells and subsequent clearance of transduced muscle fibers. A goal was to determine whether the novel miR-BS cassettes described herein have the same capacity to repress cytotoxic T cell recruitment and tissue clearance. Histopathology and immunohistopathology analyses of the injected TA muscle tissue was performed two weeks after rAAV treatment. H & E imaging showed that rAAV1.OVA-injected TAs had a high degree of cellular infiltration. Tissues injected with AAV vectors containing miR-BSs showed reductions in infiltrates (FIG. 15D; top panels). Quantification of the number of nuclei in TA cross-sections showed significant decreases in cellular infiltration in mice treated with vectors carrying miR-BSs. The miR-142/652-5pBS cassette conferred the lowest abundance of immune cell infiltrates (FIG. 15E). Moreover, H&E-stained cross-sections of TA muscles from animals treated with rAAV1.OVA and rAAV1.OVA.miR-223-3pBS vectors revealed a high degree of centrally located myonuclei. In healthy muscle fibers, myonuclei are located at the periphery of the muscle fiber. Centrally located myonuclei are indicators of myofiber regeneration following damage. These results are thus indicative of active clearance of transduced myofibers and muscle turnover. Notably, centrally located nuclei are absent in the TAs of mice treated with vectors carrying the miR-652-5pBS element (FIG. 6E).

Immunohistochemical staining of the treated muscle sections for CD8+ T cells, granzyme B, F4/80, and OVA was performed. Granzyme B is a marker for activated cytotoxic T cells and F4/80 is a cell surface marker for macrophages. Robust CD8+ T cell (CTL) infiltration in muscle samples from rAAV1.OVA-injected animals was observed, and about one-third of infiltrates were positive for granzyme B (FIG. 15D; bottom panels and FIGS. 15F and 15G). A significantly lower degree of CTL infiltration was observed among muscles injected with vectors bearing miR-142BS, miR-652-5pBS, miR-142/223-3pBS, and miR-142/652-5pBS elements, of which a very small portion expressed granzyme B. While the number of CD8+ T cells was reduced at least three-fold, a two-fold reduction observed in granzyme B expression with the incorporation of these miR-BSs was observed (FIGS. 15F and 15G). Although miR-223-3pBS-containing vectors showed relatively higher numbers of CD8+ T cells, granzyme B expression was considerably lower, indicating reduced CTL activity.

CTL infiltration was accompanied by macrophage infiltration in the injected muscle tissues of rAAV1.OVA-treated mice (FIGS. 24A and 24B). Tissues with a high abundance of CTLs and macrophages also had relatively low OVA expression (FIGS. 24A and 24B). Tissues of mice treated with OVA vectors that harbored miR-BS elements expressed high levels of OVA and conferred reduced levels of macrophage activation (~two-fold reduction). Consistent with CTL infiltration, miR-652-5pBS-bearing vectors showed the lowest degree of infiltration into injected TAs (more than four-fold reduction) by macrophages. These findings indicate that inclusion of miR-BS elements in the OVA transgene led to a reduction in cytotoxic CD8+ T cell and macrophage infiltration, resulting in reduced clearance of transduced muscle fibers, and ultimately efficient and stable transgene expression in the tissue.

Example 9: Materials and Methods Associated with Examples 1-8

Vector Plasmid Construction and rAAV Production rAAV expression cassette was made by inserting full-length OVA cDNA between the chicken β-actin (CB) promoter and rabbit β-globin (RBG) polyA signal to generate the pAAV.CB.OVA cis plasmid. For pAAV.CB.OVA.miR-BS constructs, two copies of the miR-BS sequence, individually or in combination with miR-142BS, were inserted between the OVA cDNA and RBG polyA signal. The sequences of the miR-BS are listed in Table 1. All expression cassettes were verified by Sanger sequencing. rAAV1 vectors were produced.

In Vitro Screening of OVA Constructs

OVA expression plasmids with or without the miR-142BS elements were transfected into mouse myoblast C2C12 cells (ATCC, CRL-1772) and the macrophage cell line RAW264.7 (ATCC, TIB-71) using jetPRIME transfection reagents (Polyplus-transfection SA) according to the manufacturer's instructions. C2C12 and RAW264.7 cells were cultured in Dulbecco's modified Eagle medium (Hyclone, SH30022) with 20% and 10% fetal bovine serum, respectively (FBS, Hyclone, SH30071), and 1% penicillin/streptomycin (Hyclone, SV30010). C2C12 cells were differentiated by culturing the cells in DMEM containing 2% horse serum (HyClone) and 1 µM insulin (Sigma-Aldrich). Mouse dendritic cells (JAWS II; ATCC, CRL-11904) were cultured in a minimum essential medium (MilliporeSigma, M8042) with ribonucleosides, deoxyribonucleosides, 4 mM L-glutamine, 1 mM sodium pyruvate, and 20% FBS with 5 ng/mL murine GM-CSF. JAWS II were transfected by Nucleofection. Briefly, 2.0×106 cells were collected and resuspended in 100 µL Nucleofector Solution (Lonza, V4XP-4024) at room temperature. Plasmids were then added, mixed, and transferred into Nucleocuvette Vessels. The P4 HF program for immature mouse DCs was selected and ran. 2 mL of medium was then added, and cells were split into a 24-well plate (500 µL/well) (Corning, CLS3527). Three days after transfection, supernatants were collected for OVA ELISA. A Gaussia luciferase expression plasmid was transfected along with OVA expression plasmids to account for transfection variabilities. Transfections were done in triplicate for each round.

Mice

C57BL/6 mice mice were housed under specific pathogen-free conditions. Six- to eight-week-old male mice were injected unilaterally into tibialis anterior (TA) muscles with $1.0 \times 10^{11}$ genome copies (GCs) of rAAV1 diluted in sterile phosphate-buffered saline (PBS). Blood samples were collected via facial vein by using an animal lancet (Goldenrod) and BD Microtainer tubes with serum separator additive (Becton Dickinson and Company).

ELISAs (Enzyme-Linked Immunoassays)

Serum levels of OVA and anti-OVA IgG were determined by ELISA. Briefly, 96-well Nunc Maxisorp Immunoplates (Thermo Fisher Scientific) were coated with 2 µg/mL of rabbit anti-OVA polyclonal antibodies or OVA protein in 100 µL coating buffer (KPL) per well. After an overnight incubation at 4° C., plates were washed with 0.05% Tween-20 in PBS, followed by incubation with blocking buffer (KPL) for two hours at room temperature. For OVA detection, the samples were diluted 100-fold with ELISA diluent (KPL), and OVA protein standards were two-fold serially diluted with 1% normal mouse serum starting from 50 ng/mL. 100 µL of sample or standard was then added to plates and incubated for one hour at room temperature. After washing four times, peroxidase-conjugated rabbit anti-OVA polyclonal antibody (200-4333-0100, Rockland Immunochemicals) (1:5,000 diluted) was added and incubated for one hour at room temperature. For anti-OVA IgG1 detection, samples were diluted 1:200, and the mouse anti-OVA IgG1 was used as the standard. After a one-hour incubation in OVA-coated plates, wells were washed, HRP-conjugated goat anti-mouse IgG1 (sc-2060, Santa Cruz Biotechnology) was added, and plates were incubated for another hour at room temperature. Plates were then washed four times and incubated with 100 µL of ABTS HRP Substrate (KPL). Optical density at 410 nm was measured using a Synergy HT microplate reader. Standard curves for OVA and IgG1 were generated by using the 4-parameter logistic regression with Gen5 software.

ELISA quantification of secreted cytokine levels was performed using customized ProcartaPlex Immunoassays. Briefly, the samples were incubated in a 96-well plate with magnetic beads conjugated to antibodies against desired cytokines for two hours at room temperature with shaking. Wells were then washed thrice with wash buffer, using a magnetic plate washer. This wash step was followed by incubation with detection antibody for one hour at room temperature with shaking. Following three washes, the samples were incubated with Streptavidin-PE for 30 mins at room temperature with shaking. The samples were finally resuspended in 1× reading buffer after three washes. Plates were read in a MAGPIX® System instrument. Standard curves were generated, and the levels of each cytokine were calculated using the 4-parameter logistic regression using GraphPad Prism 8.

Isolation of Immune Cells From Liver and TA Muscle

Mice were anesthetized and perfused with PBS by transcardial perfusion. Livers and injected TA muscles were harvested from perfused mice and stored temporarily in RPMI media on ice. Tissues were minced with a razor blade followed by enzymatic digestion (0.4% Collagenase type II and 300m/mL DNase I for 30 min at 37° C. Dissociated livers were strained through a 70 µm cell strainer and washed twice with 1× processing buffer (5% FBS in PBS). Cell pellets were resuspended in 40% Percoll and carefully overlaid onto 70% Percoll followed by centrifugation for 25 mins at 400 g, with the brakes off. Leukocytes that band at the 40-70% interphase were removed with a pipette onto a fresh tube and washed thrice with 1× processing buffer to prepare them for staining.

Minced TAs were incubated with 0.5 mg/mL DNase I and 0.25 mg/mL Liberase TL in processing buffer for two hours at 37° C. The digested pieces were pooled and strained through a 70 µm cell strainer. Cell suspensions were washed at 1,500 rpm for 7 min in complete RPMI followed by resuspension of the cell pellet in processing buffer for staining.

Flow Cytometry

Cells were suspended in 100 µL PBS with 5% FBS and washed once in PBS. For live/dead staining, cells were resuspended in PBS containing Fixable viability dye eFluor 506 (Thermo Fisher Scientific; 1:1000 dilution) and incubated for 30 min at 4° C. in the dark. Following one wash with FACS buffer (2% FBS in PBS), the cells were blocked with anti-CD16/32 (2.4G2) mAb (1:100 dilution) for 15 min at 4° C. After blocking, the corresponding antibodies were added at 1:100 dilution for 30 min at 4° C. in the dark. Following antibody staining, cells were washed twice in FACS buffer. Flow cytometry analyses were performed. Data were analyzed using FlowJo.

For intracellular staining, cells were permeabilized in a 1× solution of fixation/permeabilization solution for 30 min at 4° C. after blocking/cell surface staining. Thereafter, the cells were washed thrice in 1× Perm/Wash buffer. Antibody dilutions (1:100) were prepared in 1× Perm/Wash buffer and cells were resuspended in the antibody containing solution and incubated for 30 min at 4° C. Following antibody staining, cells were washed once in 1× Perm/Wash buffer and resuspended in FACS buffer for analyses by flow cytometry.

qPCR and RT-qPCR

Mouse tissue DNA was isolated using the QIAamp genomic DNA kit following manufacturer's instructions. Detection and quantification of vector genomes in extracted DNA were performed by real-time qPCR. Total RNA was isolated from mouse tissues or cells using Trizol. cDNA preparation for miRNA quantification was done using TaqMan™ MicroRNA Reverse Transcription Kit following manufacturer's instructions. qPCR to quantify expression levels of miR-142-3p, miR-652-3p, miR-652-5p, miR-223-3p, and miR-33-5p were done using TaqMan™ Fast Advanced Master Mix. Real-time qPCR was performed using the ViiA 7 real-time PCR system.

Immunohistochemistry

Mouse tissues were fixed in 10% buffered formalin overnight and embedded in paraffin. Sections (8 µm thick) were stained with H&E. Images were acquired on a TissueFAXS Whole Slide Scanning System using a 20× objective. Nuclei quantification was performed with Image J.

For immunofluorescence staining, muscle sections were de-paraffinized in xylene and rehydrated using a graded ethanol series culminating with PBS. Following antigen retrieval using a programmable pressure cooker with "target retrieval solution", pH 6.0, tissue sections were blocked with 10% goat serum in PBS. The slides were then stained for CD8 (1:500), granzyme B (1:40), F4/80 (1:100), and OVA (1:500) for 16 hours at 4° C. Species-specific secondary antibodies conjugated to Cy5 or Cy7 fluorophores were used and incubated for one hour at room temperature in the dark.

Sections were washed, counterstained with DAPI (100 ng/ml) and mounted using FluorSave mounting medium. Images were acquired on a laser scanning confocal microscope using a 40× oil-immersion objective. Quantification of the fluorescent signals of the respective markers was performed using QuPath.

Statistics

All data were shown as mean±SD. Unpaired Student's t tests (two-tailed), one-way ANOVA and two-way ANOVA, with or without post hoc testing, were calculated using GraphPad Prism 8. Differences were considered significant when $p$ values were less than 0.05.

```
Additional sequence information

>SEQ ID NO: 34 (rAAV comprising miR-223-3pBS)
ctgcgcgctcgctcgctcactgaggccgcccgggcaaagcccgggcgtcgggcgacctttggtcgcccggcctcagtgagcgagcga
gcgcgcagagagggagtggccaactccatcactaggggttccttgtagttaatgattaacccgccatgctacttatctaccagggtaatggg
gatcctctagaactatagctagtcgacattgattattgactagttattaatagtaatcaattacggggtcattagttcatagcccatatatggagtt
ccgcgttacataacttacggtaaatggcccgcctggctgaccgcccaacgaccccccgcccattgacgtcaataatgacgtatgttcccatag
taacgccaatagggactttccattgacgtcaatgggtggagtatttacggtaaactgcccacttggcagtacatcaagtgtatcatatgccaag
tacgccccctattgacgtcaatgacggtaaatggcccgcctggcattatgcccagtacatgaccttatgggactttcctacttggcagtacatc
tacgtattagtcatcgctattaccatgtcgaggccacgttctgcttcactctccccatctccccccctccccaccccccaattttgtatttatttattt
tttaattattttgtgcagcgatggggcggggggggggggcgcgcgccaggcggggcggggcgggcgagggggcgggcggggcg
aggcggagaggtgcggcggcagccaatcagagcggcgcgctccgaaagtttccttttatggcgaggcggcggcggcggcggccctat
aaaaagcgaagcgcgcggcgggcgggagcaagctttattgcggtagtttatcacagttaaattgctaacgcagtcagtgcttctgacacaa
cagtctcgaacttaagctgcagaagttggtcgtgaggcactgggcaggtaagtatcaaggttacaagacaggtttaaggagaccaatagaa
actgggcttgtcgagacagagaagactcttgcgtttctgataggcacctattggtcttactgacatccactttgcctttctctccacaggtgtcca
ctcccagttcaattacagctcttaaggctagagtacttaatacgactcactataggctagcggcgccatgggctccatcggcgcagcaagca
tggaattttgttttgatgtattcaaggagctcaaagtccaccatgccaatgagaacatcttctactgcccccattgccatcatgtcagctctagcca
tggtataccctgggtgcaaaagacagcaccaggacacaaataaataaggttgttcgctttgataaacttccaggattcggagacagtattgaa
gctcagtgtggcacatctgtaaacgttcactcttcacttagagacatcctcaaccaaatcaccaaaccaaatgatgtttattcgttcagccttgc
cagtagactttatgctgaagagagatacccaatcctgccagaatacttgcagtgtgtgaaggaactgtatagaggaggcttggaacctatca
actttcaaacagctgcagatcaagccagagagctcatcaattcctgggtagaaagtcagacaaatggaattatcagaaatgtccttcagcca
agctccgtggattctcaaactgcaatggttctggttaatgccattgtcttcaaaggactgtgggagaaaacatttaaggatgaagacacacaa
gcaatgcctttcagagtgactgagcaagaaagcaaacctgtgcagtgatgtaccagattggtttatttagagtggcatcaatggcttctgag
aaaatgaagatcctggagcttccatttgccagtgggacaatgagcatgtttggtgctgttgcctgatgaagtctcaggccttgagcagcttgag
agtataatcaactttgaaaaactgactgaatggaccagttctaatgttatggaagagaggaagatcaaagtgtacttacctcgcatgaagatg
gaggaaaaatacaacctcacatctgtcttaatggctatgggcattactgacgtgtttagctcttcagccaatctgtctggcatctcctcagcaga
gagcctgaagatatctcaagctgtccatgcagcacatgcagaaatcaatgaagcaggcagagaggtggtagggtcagcagaggctgga
gtggatgctgcaagcgtctctgaagaatttagggctgaccatccattcctcttctgtatcaagcacatcgcaaccaacgccgttctcttctttgg
cagatgtgtttcccctttaaaaagaagaaagctgaaaaactctgtcccttccaacaagacccagagcactgtagtatcaggggtaaaatgaaa
agtatgttctctgctgcatccagacttcataaaagctggagcttaatctagagtcgacctgcagaagcttgctgaattcTGGGGTATT
TGACAAACTGACATGGGGTATTTGACAAACTGACAggtacctctagagtcgaccccgggccggcctcgag
gacggggtgaactacgcctgaggatccgatcttttttccctctgccaaaaattatggggacatcatgaagcccttgagcatctgacttctggc
taataaaggaaatttattttcattgcaatagtgtgttggaattttttgtgtctctcactcggaagcaattcgttgatctgaattcgaccacccataat
acccattaccctggtagataagtagcatggcgggttaatcattaactacaaggaaccccctagtgatggagttggccactccctctctgcgcg
ctcgctcgctcactgaggccgggcgaccaaaggtcgcccgacgcccgggctttgcccgggcggcctcagtgagcgagcgagcgcgcag >SEQ ID NO: 35 (rAAV comprising miR-652BS)
ctgcgcgctcgctcgctcactgaggccgcccgggcaaagcccgggcgtcgggcgacctttggtcgcccggcctcagtgagcgagcga
gcgcgcagagagggagtggccaactccatcactaggggttccttgtagttaatgattaacccgccatgctacttatctaccagggtaatggg
gatcctctagaactatagctagtcgacattgattattgactagttattaatagtaatcaattacggggtcattagttcatagcccatatatggagtt
ccgcgttacataacttacggtaaatggcccgcctggctgaccgcccaacgaccccccgcccattgacgtcaataatgacgtatgttcccatag
taacgccaatagggactttccattgacgtcaatgggtggagtatttacggtaaactgcccacttggcagtacatcaagtgtatcatatgccaag
tacgccccctattgacgtcaatgacggtaaatggcccgcctggcattatgcccagtacatgaccttatgggactttcctacttggcagtacatc
tacgtattagtcatcgctattaccatgtcgaggccacgttctgcttcactctccccatctccccccctccccaccccccaattttgtatttatttattt
tttaattattttgtgcagcgatggggcggggggggggggcgcgcgccaggcggggcggggcgggcgagggggcgggcggggcg
aggcggagaggtgcggcggcagccaatcagagcggcgcgctccgaaagtttccttttatggcgaggcggcggcggcggcggccctat
aaaaagcgaagcgcgcggcgggcgggagcaagctttattgcggtagtttatcacagttaaattgctaacgcagtcagtgcttctgacacaa
cagtctcgaacttaagctgcagaagttggtcgtgaggcactgggcaggtaagtatcaaggttacaagacaggtttaaggagaccaatagaa
actgggcttgtcgagacagagaagactcttgcgtttctgataggcacctattggtcttactgacatccactttgcctttctctccacaggtgtcca
ctcccagttcaattacagctcttaaggctagagtacttaatacgactcactataggctagcggcgccatgggctccatcggcgcagcaagca
tggaattttgttttgatgtattcaaggagctcaaagtccaccatgccaatgagaacatcttctactgcccccattgccatcatgtcagctctagcca
tggtataccctgggtgcaaaagacagcaccaggacacaaataaataaggttgttcgctttgataaacttccaggattcggagacagtattgaa
gctcagtgtggcacatctgtaaacgttcactcttcacttagagacatcctcaaccaaatcaccaaaccaaatgatgtttattcgttcagccttgc
cagtagactttatgctgaagagagatacccaatcctgccagaatacttgcagtgtgtgaaggaactgtatagaggaggcttggaacctatca
actttcaaacagctgcagatcaagccagagagctcatcaattcctgggtagaaagtcagacaaatggaattatcagaaatgtccttcagcca
agctccgtggattctcaaactgcaatggttctggttaatgccattgtcttcaaaggactgtgggagaaaacatttaaggatgaagacacacaa
gcaatgcctttcagagtgactgagcaagaaagcaaacctgtgcagtgatgtaccagattggtttatttagagtggcatcaatggcttctgag
aaaatgaagatcctggagcttccatttgccagtgggacaatgagcatgtttggtgctgttgcctgatgaagtctcaggccttgagcagcttgag
agtataatcaactttgaaaaactgactgaatggaccagttctaatgttatggaagagaggaagatcaaagtgtacttacctcgcatgaagatg
gaggaaaaatacaacctcacatctgtcttaatggctatgggcattactgacgtgtttagctcttcagccaatctgtctggcatctcctcagcaga
gagcctgaagatatctcaagctgtccatgcagcacatgcagaaatcaatgaagcaggcagagaggtggtagggtcagcagaggctgga
gtggatgctgcaagcgtctctgaagaatttagggctgaccatccattcctcttctgtatcaagcacatcgcaaccaacgccgttctcttctttgg
cagatgtgtttcccctttaaaaagaagaaagctgaaaaactctgtcccttccaacaagacccagagcactgtagtatcaggggtaaaatgaaa
agtatgttctctgctgcatccagacttcataaaagctggagcttaatctagagtcgacctgcagaagcttgctgaattcGAATGGCAC
CCCCTCCTAGGGTTGGAATGGCACCCCCTCCTAGGGTTGggtacctctagagtcgaccccgggccggcc
tcgaggacggggtgaactacgcctgaggatccgatctattccctctgccaaaaattatggggacatcatgaagcccttgagcatctgactt
ctggctaataaaggaaatttattttcattgcaatagtgtgttggaattttttgtgtctctcactcggaagcaattcgttgatctgaattcgaccacc
cataatacccattaccctggtagataagtagcatggcgggttaatcattaactacaaggaaccccctagtgatggagttggccactccctctct
gcgcgctcgctcgctcactgaggccgggcgaccaaaggtcgcccgacgcccgggctttgcccgggcggcctcagtgagcgagcgagcgcgcag >SEQ ID NO: 36 (rAAV comprising miR-142BS + miR-652BS)
ctgcgcgctcgctcgctcactgaggccgcccgggcaaagcccgggcgtcgggcgacctttggtcgcccggcctcagtgagcgagcga
gcgcgcagagagggagtggccaactccatcactaggggttccttgtagttaatgattaacccgccatgctacttatctaccagggtaatggg
```

-continued

Additional sequence information gatcctctagaactatagctagtcgacattgattattgactagttattaatagtaatcaattacggggtcattagttcatagcccatatatggagtt
ccgcgttacataacttacggtaaatggcccgcctggctgaccgcccaacgaccccgcccattgacgtcaataatgacgtatgttcccatag
taacgccaatagggactttccattgacgtcaatgggtggagtatttacggtaaactgcccacttggcagtacatcaagtgtatcatatgccaag
tacgccccctattgacgtcaatgacggtaaatggcccgcctggcattatgcccagtacatgaccttatgggactttcctacttggcagtacatc
tacgtattagtcatcgctattaccatgtcgaggccacgttctgcttcactctccccatctcccccccctccccaccccaatttttgtatttatttattt
tttaattattttgtgcagcgatggggcggggggggggcgcgcgccaggcggggcggggcggggcgagggcggggcgggcg
aggcggagaggtgcggcggcagccaatcagagcggcgcgctccgaaagtttcctttttatggcgaggcggcggcggcggcgccctat
aaaaagcgaagcgcgcggcgggcgggagcaagctttattgcggtagtttatcacagttaaattgctaacgcagtcagtgcttctgacacaa
cagtctcgaacttaagctgcagaagttggtcgtgaggcactgggcaggtaagtatcaaggttacaagacaggtttaaggagaccaataga
actgggcttgtcgagacagagaagactcttgcgtttctgataggcacctattggtcttactgacatccactttgcctttctctccacaggtgtcca
ctcccagttcaattacagctcttaaggctagagtacttaatacgactcactataggctagcggcgccatgggctccatcggcgcagcaagca
tggaatttttgttttgatgtattcaaggagctcaaagtccaccatgccaatgagaacatcttctactgccccattgccatcatgtcagctctagcca
tggtatacctgggtgcaaaagacagcaccaggacacaaataaataaggttgttcgctttgataaacttccaggattcggagacagtattgaa
gctcagtgtggcacatctgtaaacgttcactcttcacttagagacatcctcaaccaaatcaccaaaccaaatgatgtttattcgttcagccttgc
cagtagactttatgctgaagagagatacccaatcctgccagaatacttgcagtgtgtgaaggaactgtatagaggaggcttggaacctatca
actttcaaacagctgcagatcaagccagagagctcatcaattcctgggtagaaagtcagacaaatggaattatcagaaatgtccttcagcca
agctccgtggattctcaaactgcaatggttctggttaatgccattgtcttcaaaggactgtgggagaaaacatttaaggatgaagacacacaa
gcaatgcctttcagagtgactgagcaagaaagcaaacctgtgcagatgatgtaccagattggttatttagagtggcatcaatggctctgag
aaaatgaagatcctggagcttccatttgccagtgggacaatgagcatgttggtgctgttgcctgatgaagtctcaggccttgagcagcttgag
agtataatcaactttgaaaaactgactgaatggaccagttctaatgttatggaagagaggaagatcaaagtgtacttacctcgcatgaagatg
gaggaaaaatacaacctcacatctgtcttaatggctatgggcattactgacgtgtttagctcttcagccaatctgtctggcatctcctcagcaga
gagcctgaagatatctcaagctgtccatgcagcacatgcagaaatcaatgaagcaggcagagaggtggtagggtcagcagaggctgga
gtggatgctgcaagcgtctctgaagaatttagggctgaccatccattcctcttctgtatcaagcacatcgcaaccaacgccgttctcttctttgg
cagatgtgtttccccttaaaaagaagaaagctgaaaaactctgtcccttccaacaagacccagagcactgtagtatcaggggtaaaatgaaa
agtatgttctctgctgcatccagacttcataaaagctggagcttaatctagagtcgacctgcagaagcttgctgaattctccataaagtaggaa
acactacatccataaagtaggaaacactacaGAATGGCACCCCCTCCTAGGGTTGGAATGGCACCCCC
TCCTAGGGTTGggtacctctagagtcgacccgggcggcctcgaggacggggtgaactacgcctgaggatccgatctttttccct
ctgccaaaaattatggggacatcatgaagcccttgagcatctgactctggctaataaaggaaattttatttcattgcaatagtgtgttggaatt
ttttgtgtctctcactcggaagcaattcgttgatctgaattttcgaccacccataatacccattaccctggtagataagtagcatggcgggttaatc
attaactacaaggaaccctagtgatggagttggccactccctctctgcgcgctcgctcgctcactgaggccgggcgaccaaaggtcgcc
cgacgcccgggctttgcccgggcggcctcagtgagcgagcgagcgcgcag >SEQ ID NO: 37 (rAAV comprising miR-142BS + miR-223-3pBS)
ctgcgcgctcgctcgctcactgaggccgcccgggcaaagcccgggcgtcgggcgacctttggtcgcccggcctcagtgagc
gagcgagcgcgcagagagggagtggccaactccatcactaggggttccttgtagttaatgattaacccgccatgctacttatctaccagggt
aatgggatcctctagaactatagctagtcgacattgattattgactagttattaatagtaatcaattacggggtcattagttcatagcccatatat
ggagttccgcgttacataacttacggtaaatggcccgcctggctgaccgcccaacgaccccgcccattgacgtcaataatgacgtatgttc
ccatagtaacgccaatagggactttccattgacgtcaatgggtggagtatttacggtaaactgcccacttggcagtacatcaagtgtatcatat
gccaagtacgccccctattgacgtcaatgacggtaaatggcccgcctggcattatgcccagtacatgaccttatgggactttcctacttggca
gtacatctacgtattagtcatcgctattaccatgtcgaggccacgttctgcttcactctccccatctcccccccctccccaccccaatttttgtatt
tatttattttttaattattttgtgcagcgatggggcggggggggggcgcgcgccaggcggggcggggcggggcgagggcggggc
ggggcgaggcggagaggtgcggcggcagccaatcagagcggcgcgctccgaaagtttcctttttatggcgaggcggcggcggcg
gcctataaaaagcgaagcgcgcggcgggcgggagcaagctttattgcggtagtttatcacagttaaattgctaacgcagtcagtgcttctg
acacaacagtctcgaacttaagctgcagaagttggtcgtgaggcactgggcaggtaagtatcaaggttacaagacaggtttaaggagacc
aatagaactgggcttgtcgagacagagaagactcttgcgtttctgataggcacctattggtcttactgacatccactttgcctttctctccaca
ggtgtccactcccagttcaattacagctcttaaggctagagtacttaatacgactcactataggctagcggcgccatgggctccatcggcgc
agcaagcatggaatttttgttttgatgtattcaaggagctcaaagtccaccatgccaatgagaacatcttctactgccccattgccatcatgtcag
ctctagccatggtatacctgggtgcaaaagacagcaccaggacacaaataaataaggttgttcgctttgataaacttccaggattcggagac
agtattgaagctcagtgtggcacatctgtaaacgttcactcttcacttagagacatcctcaaccaaatcaccaaaccaaatgatgtttattcgttc
agccttgccagtagactttatgctgaagagagatacccaatcctgccagaatacttgcagtgtgtgaaggaactgtatagaggaggcttgga
acctatcaactttcaaacagctgcagatcaagccagagagctcatcaattcctgggtagaaagtcagacaaatggaattatcagaaatgtcct
tcagccaagctccgtggattctcaaactgcaatggttctggttaatgccattgtcttcaaaggactgtgggagaaaacatttaaggatgaaga
cacacaagcaatgcctttcagagtgactgagcaagaaagcaaacctgtgcagatgatgtaccagattggttatttagagtggcatcaatgg
cttctgagaaaatgaagatcctggagcttccatttgccagtgggacaatgagcatgttggtgctgttgcctgatgaagtctcaggccttgagc
agcttgagagtataatcaactttgaaaaactgactgaatggaccagttctaatgttatggaagagaggaagatcaaagtgtacttacctcgcat
gaagatggaggaaaaatacaacctcacatctgtcttaatggctatgggcattactgacgtgtttagctcttcagccaatctgtctggcatctcct
cagcagagagcctgaagatatctcaagctgtccatgcagcacatgcagaaatcaatgaagcaggcagagaggtggtagggtcagcaga
ggctggagtggatgctgcaagcgtctctgaagaatttagggctgaccatccattcctcttctgtatcaagcacatcgcaaccaacgccgttct
cttctttggcagatgtgtttccccttaaaaagaagaaagctgaaaaactctgtcccttccaacaagacccagagcactgtagtatcaggggta
aaatgaaaagtatgttctctgctgcatccagacttcataaaagctggagcttaatctagagtcgacctgcagaagcttgctgaattctccataa
agtaggaaacactacatccataaagtaggaaacactacatggggtatttgacaaactgacatggggtatttgacaaactgacaggtacctct
agagtcgacccgggcggcctcgaggacggggtgaactacgcctgaggatccgatctttttccctctgccaaaaattatggggacatcatga
agccccttgagcatctgacttctggctaataaaggaaattttattttcattgcaatagtgtgttggaattttttgtgtctctcactcggaagcaattcg
ttgatctgaatttcgaccacccataatacccattaccctggtagataagtagcatggcgggttaatcattaactacaaggaaccctagtgatg
gagttggccactccctctctgcgcgctcgctcgctcactgaggccgggcgaccaaaggtcgcccgacgcccgggctttgcccgggcgg
cctcagtgagcgagcgagcgcgcag >SEQ ID NO: 38 (miR-223-3p BS)
TGGGGTATTTGACAAACTGACA >SEQ ID NO: 39 (miR-652-5p BS)
GAATGGCACCCCCTCCTAGGGTTG >SEQ ID NO: 40 (miR-142BS + miR-652-5p BS)
TCCATAAAGTAGGAAACACTACATCCATAAAGTAGGAAACACTACAGAATGGCACC
CCCTCCTAGGGTTGGAATGGCACCCCCTCCTAGGGTTGGG

```
                   Additional sequence information

>SEQ ID NO: 41 (miR-142BS + miR-223-3p BS)
TCCATAAAGTAGGAAACACTACATCCATAAAGTAGGAAACACTACATGGGGTATTT
GACAAACTGACATGGGGTATTTGACAAACTGACA

>SEQ ID NO: 42 (miR-223-3p BS)
UGGGGUAUUUGACAAACUGACA

>SEQ ID NO: 43 (miR-652-5p BS)
GAAUGGCACCCCCUCCUAGGGUUG

>SEQ ID NO: 44 (miR-142BS + miR-652-5p BS)
UCCAUAAAGUAGGAAACACUACAUCCAUAAAGUAGGAAACACUACAGAAUGGCA
CCCCCUCCUAGGGUUGGAAUGGCACCCCCUCCUAGGGUUGGG

>SEQ ID NO: 45 (miR-142BS + miR-223-3p BS)
UCCAUAAAGUAGGAAACACUACAUCCAUAAAGUAGGAAACACUACAUGGGGUAU
UUGACAAACUGACAUGGGGUAUUUGACAAACUGACA
```

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, and/or method described herein. In addition, any combination of two or more such features, systems, articles, materials, and/or methods, if such features, systems, articles, materials, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

What is claimed is:

1. A method of delivering a transgene to target cells of a subject, the method comprising administering to the subject a recombinant Adeno-Associated Virus (rAAV) comprising a transgene, wherein the transgene comprises a promoter operably linked to a nucleic acid sequence that encodes an RNA transcript that comprises at least one immune-associated miRNA binding site (BS), wherein the rAAV infects target cells of the subject thereby delivering the transgene to the target cells, wherein the at least one immune-associated miRNA binding site comprises a miR-652-5pBS and a miR142BS.

2. The method of claim 1, wherein the at least one immune-associated miRNA is expressed in dendritic cells, macrophages, T-lymphocytes, B-lymphocytes, monocytes, or myeloid cells.

3. The method of claim 1, wherein the at least one immune-associated miRNA binding site further comprises a binding site for one of the following miRNAs:
miR-33-5pBS, a miR-223BS, miR-106, miR-125a, miR-125b, miR-126a, miR-142, miR-146a, miR-15, miR-150, miR-155, miR-16, miR-17, miR-18, miR-181a, miR-19a, miR-19b, miR-20, miR-21a, miR-223, miR-24-3p, miR-29a, miR-29b, miR-29c, miR-302a-3p, miR-30b, miR-33-5p, miR-34a, miR-424, miR-652-3p, miR-652-5p, miR-9-3p, miR-9-5p, miR-92a, and miR-99b 5p.

4. The method of claim 1, wherein the miR-652-5p BS is encoded by a nucleic acid having the sequence set forth in SEQ ID NO: 39.

5. The method of claim 1, wherein the at least one miRNA binding site is encoded by a nucleic acid having the sequence set forth in SEQ ID NO: 40.

6. The method of claim 1, wherein the RNA transcript is a messenger RNA (mRNA) and at least one of the miRNA binding sites is present in the 3'-UTR of the messenger RNA.

7. The method of claim 1, wherein the RNA transcript encodes a therapeutic protein.

8. The method of claim 1, wherein the administration is intramuscular.

9. The method of claim 1, wherein the subject is a human.

10. A recombinant Adeno-Associated Virus (rAAV) comprising a transgene encoding an RNA transcript that comprises at least one immune-associated miRNA binding site, wherein the at least one immune-associated miRNA binding site comprises a miR-652-5pBS and a miR142BS.

11. The rAAV of claim 10, further comprising a binding site for one of the following miRNAs: miR-33-5pBS, a miR-223BS, miR-106, miR-125a, miR-125b, miR-126a, miR-142, miR-146a, miR-15, miR-150, miR-155, miR-16, miR-17, miR-18, miR-181a, miR-19a, miR-19b, miR-20, miR-21a, miR-223, miR-24-3p, miR-29a, miR-29b, miR-29c, miR-302a-3p, miR-30b, miR-33-5p, miR-34a, miR-424, miR-652-3p, miR-652-5p, miR-9-3p, miR-9-5p, miR-92a, and miR-99b 5p.

12. The rAAV of claim 10 wherein the rAAV comprises the sequence set forth in SEQ ID NO: 43.

13. The rAAV of claim 10, wherein the rAAV comprises the sequence set forth in SEQ ID NO: 44.

14. The rAAV of claim 10, wherein the RNA transcript is a messenger RNA (mRNA) and at least one of the miRNA binding sites is present in the 3'-UTR of the messenger RNA.

15. The rAAV of claim 10, wherein the RNA transcript encodes a therapeutic protein or an inhibitory RNA selected from an shRNA, miRNA, antisense RNA, miRNA sponge, TuD RNA, and artificial miRNA.

16. The rAAV of claim 10, wherein the rAAV comprises a capsid of a serotype selected from: AAV1, AAV2, AAV3, AAV4, AAV5, AAV6, AAV7, AAV8, AAV9, AAV10, AAV11, AAV12, and variants thereof.

17. The rAAV of claim 10, wherein the transgene is flanked by inverted terminal repeat (ITR) sequences.

18. A host cell comprising the rAAV of claim 10.

19. The host cell of claim 18, wherein the host cell is a mammalian cell.

* * * * *

```
                          SEQUENCE LISTING

<160> NUMBER OF SEQ ID NOS: 46

<210> SEQ ID NO 1
<211> LENGTH: 46
<212> TYPE: DNA
<213> ORGANISM: Artificial Sequence
<220> FEATURE:
<223> OTHER INFORMATION: Synthetic

<400> SEQUENCE: 1
ctacctgcac tgttagcact ttgctacctg cactgttagc actttg              46

<210> SEQ ID NO 2
<211> LENGTH: 48
<212> TYPE: DNA
<213> ORGANISM: Artificial Sequence
<220> FEATURE:
<223> OTHER INFORMATION: Synthetic

<400> SEQUENCE: 2
tcacaggtta aagggtctca gggatcacag gttaaagggt ctcaggga            48

<210> SEQ ID NO 3
<211> LENGTH: 44
<212> TYPE: DNA
<213> ORGANISM: Artificial Sequence
<220> FEATURE:
<223> OTHER INFORMATION: Synthetic

<400> SEQUENCE: 3
tcacaagtta gggtctcagg gatcacaagt tagggtctca ggga                44

<210> SEQ ID NO 4
<211> LENGTH: 44
<212> TYPE: DNA
<213> ORGANISM: Artificial Sequence
<220> FEATURE:
<223> OTHER INFORMATION: Synthetic

<400> SEQUENCE: 4
cgcattatta ctcacggtac gacgcattat tactcacggt acga                44

<210> SEQ ID NO 5
<211> LENGTH: 46
<212> TYPE: DNA
<213> ORGANISM: Artificial Sequence
<220> FEATURE:
<223> OTHER INFORMATION: Synthetic

<400> SEQUENCE: 5
tccataaagt aggaaacact acatccataa agtaggaaac actaca              46

<210> SEQ ID NO 6
<211> LENGTH: 44
<212> TYPE: DNA
<213> ORGANISM: Artificial Sequence
<220> FEATURE:
<223> OTHER INFORMATION: Synthetic
```

<400> SEQUENCE: 6
aacccatgga attcagttct caaacccatg gaattcagtt ctca                    44

<210> SEQ ID NO 7
<211> LENGTH: 44
<212> TYPE: DNA
<213> ORGANISM: Artificial Sequence
<220> FEATURE:
<223> OTHER INFORMATION: Synthetic

<400> SEQUENCE: 7
cacaaaccat tatgtgctgc tacacaaacc attatgtgct gcta                    44

<210> SEQ ID NO 8
<211> LENGTH: 44
<212> TYPE: DNA
<213> ORGANISM: Artificial Sequence
<220> FEATURE:
<223> OTHER INFORMATION: Synthetic

<400> SEQUENCE: 8
cactggtaca agggttggga gacactggta caagggttgg gaga                    44

<210> SEQ ID NO 9
<211> LENGTH: 46
<212> TYPE: DNA
<213> ORGANISM: Artificial Sequence
<220> FEATURE:
<223> OTHER INFORMATION: Synthetic

<400> SEQUENCE: 9
acccctatca caattagcat taaacccta tcacaattag cattaa                   46

<210> SEQ ID NO 10
<211> LENGTH: 44
<212> TYPE: DNA
<213> ORGANISM: Artificial Sequence
<220> FEATURE:
<223> OTHER INFORMATION: Synthetic

<400> SEQUENCE: 10
cgccaatatt tacgtgctgc tacgccaata tttacgtgct gcta                    44

<210> SEQ ID NO 11
<211> LENGTH: 46
<212> TYPE: DNA
<213> ORGANISM: Artificial Sequence
<220> FEATURE:
<223> OTHER INFORMATION: Synthetic

<400> SEQUENCE: 11
ctacctgcac tgtaagcact ttgctacctg cactgtaagc actttg                  46

<210> SEQ ID NO 12
<211> LENGTH: 46
<212> TYPE: DNA
<213> ORGANISM: Artificial Sequence
<220> FEATURE:
<223> OTHER INFORMATION: Synthetic

<400> SEQUENCE: 12
ctatctgcac tagatgcacc ttactatctg cactagatgc accta                   46

<210> SEQ ID NO 13

<211> LENGTH: 46
<212> TYPE: DNA
<213> ORGANISM: Artificial Sequence
<220> FEATURE:
<223> OTHER INFORMATION: Synthetic

<400> SEQUENCE: 13
actcaccgac agcgttgaat gttactcacc gacagcgttg aatgtt       46

<210> SEQ ID NO 14
<211> LENGTH: 46
<212> TYPE: DNA
<213> ORGANISM: Artificial Sequence
<220> FEATURE:
<223> OTHER INFORMATION: Synthetic

<400> SEQUENCE: 14
tcagttttgc atagatttgc acatcagttt tgcatagatt tgcaca       46

<210> SEQ ID NO 15
<211> LENGTH: 46
<212> TYPE: DNA
<213> ORGANISM: Artificial Sequence
<220> FEATURE:
<223> OTHER INFORMATION: Synthetic

<400> SEQUENCE: 15
tcagttttgc atggatttgc acatcagttt tgcatggatt tgcaca       46

<210> SEQ ID NO 16
<211> LENGTH: 46
<212> TYPE: DNA
<213> ORGANISM: Artificial Sequence
<220> FEATURE:
<223> OTHER INFORMATION: Synthetic

<400> SEQUENCE: 16
ctacctgcac tataagcact ttactacctg cactataagc acttta       46

<210> SEQ ID NO 17
<211> LENGTH: 44
<212> TYPE: DNA
<213> ORGANISM: Artificial Sequence
<220> FEATURE:
<223> OTHER INFORMATION: Synthetic

<400> SEQUENCE: 17
tcaacatcag tctgataagc tatcaacatc agtctgataa gcta       44

<210> SEQ ID NO 18
<211> LENGTH: 44
<212> TYPE: DNA
<213> ORGANISM: Artificial Sequence
<220> FEATURE:
<223> OTHER INFORMATION: Synthetic

<400> SEQUENCE: 18
tggggtattt gacaaactga catggggtat ttgacaaact gaca       44

<210> SEQ ID NO 19
<211> LENGTH: 44
<212> TYPE: DNA
<213> ORGANISM: Artificial Sequence
<220> FEATURE:
<223> OTHER INFORMATION: Synthetic

<400> SEQUENCE: 19
ctgttcctgc tgaactgagc cactgttcct gctgaactga gcca        44

<210> SEQ ID NO 20
<211> LENGTH: 44
<212> TYPE: DNA
<213> ORGANISM: Artificial Sequence
<220> FEATURE:
<223> OTHER INFORMATION: Synthetic

<400> SEQUENCE: 20
taaccgattt cagatggtgc tataaccgat ttcagatggt gcta        44

<210> SEQ ID NO 21
<211> LENGTH: 46
<212> TYPE: DNA
<213> ORGANISM: Artificial Sequence
<220> FEATURE:
<223> OTHER INFORMATION: Synthetic

<400> SEQUENCE: 21
aacactgatt tcaaatggtg ctaaacactg atttcaaatg gtgcta      46

<210> SEQ ID NO 22
<211> LENGTH: 44
<212> TYPE: DNA
<213> ORGANISM: Artificial Sequence
<220> FEATURE:
<223> OTHER INFORMATION: Synthetic

<400> SEQUENCE: 22
taaccgattt caaatggtgc tataaccgat ttcaaatggt gcta        44

<210> SEQ ID NO 23
<211> LENGTH: 46
<212> TYPE: DNA
<213> ORGANISM: Artificial Sequence
<220> FEATURE:
<223> OTHER INFORMATION: Synthetic

<400> SEQUENCE: 23
tcaccaaaac atggaagcac ttatcaccaa aacatggaag cactta      46

<210> SEQ ID NO 24
<211> LENGTH: 44
<212> TYPE: DNA
<213> ORGANISM: Artificial Sequence
<220> FEATURE:
<223> OTHER INFORMATION: Synthetic

<400> SEQUENCE: 24
agctgagtgt aggatgttta caagctgagt gtaggatgtt taca        44

<210> SEQ ID NO 25
<211> LENGTH: 42
<212> TYPE: DNA
<213> ORGANISM: Artificial Sequence
<220> FEATURE:
<223> OTHER INFORMATION: Synthetic

<400> SEQUENCE: 25
tgcaatgcaa ctacaatgca ctgcaatgca actacaatgc ac          42

<210> SEQ ID NO 26

<210> SEQ ID NO 26
<211> LENGTH: 44
<212> TYPE: DNA
<213> ORGANISM: Artificial Sequence
<220> FEATURE:
<223> OTHER INFORMATION: Synthetic

<400> SEQUENCE: 26
acaaccagct aagacactgc caacaaccag ctaagacact gcca        44

<210> SEQ ID NO 27
<211> LENGTH: 44
<212> TYPE: DNA
<213> ORGANISM: Artificial Sequence
<220> FEATURE:
<223> OTHER INFORMATION: Synthetic

<400> SEQUENCE: 27
ttcaaaacat gaattgctgc tgttcaaaac atgaattgct gctg        44

<210> SEQ ID NO 28
<211> LENGTH: 42
<212> TYPE: DNA
<213> ORGANISM: Artificial Sequence
<220> FEATURE:
<223> OTHER INFORMATION: Synthetic

<400> SEQUENCE: 28
aatggcgcca ctagggttgt gaatggcgcc actagggttg tg          42

<210> SEQ ID NO 29
<211> LENGTH: 48
<212> TYPE: DNA
<213> ORGANISM: Artificial Sequence
<220> FEATURE:
<223> OTHER INFORMATION: Synthetic

<400> SEQUENCE: 29
gaatggcacc ccctcctagg gttggaatgg caccccctcc tagggttg    48

<210> SEQ ID NO 30
<211> LENGTH: 44
<212> TYPE: DNA
<213> ORGANISM: Artificial Sequence
<220> FEATURE:
<223> OTHER INFORMATION: Synthetic

<400> SEQUENCE: 30
actttcggtt atctagcttt atactttcgg ttatctagct ttat        44

<210> SEQ ID NO 31
<211> LENGTH: 46
<212> TYPE: DNA
<213> ORGANISM: Artificial Sequence
<220> FEATURE:
<223> OTHER INFORMATION: Synthetic

<400> SEQUENCE: 31
tcatacagct agataaccaa agatcataca gctagataac caaaga      46

<210> SEQ ID NO 32
<211> LENGTH: 42
<212> TYPE: DNA
<213> ORGANISM: Artificial Sequence
<220> FEATURE:
<223> OTHER INFORMATION: Synthetic -continued

<400> SEQUENCE: 32
caggccggga caagtgcaat acaggccggg acaagtgcaa ta                42

<210> SEQ ID NO 33
<211> LENGTH: 44
<212> TYPE: DNA
<213> ORGANISM: Artificial Sequence
<220> FEATURE:
<223> OTHER INFORMATION: Synthetic

<400> SEQUENCE: 33
cgcaaggtcg gttctacggg tgcgcaaggt cggttctacg ggtg              44

<210> SEQ ID NO 34
<211> LENGTH: 2934
<212> TYPE: DNA
<213> ORGANISM: Artificial Sequence
<220> FEATURE:
<223> OTHER INFORMATION: Synthetic

<400> SEQUENCE: 34
ctgcgcgctc gctcgctcac tgaggccgcc cgggcaaagc ccgggcgtcg ggcgaccttt     60
ggtcgcccgg cctcagtgag cgagcgagcg cgcagagagg gagtggccaa ctccatcact    120
aggggttcct tgtagttaat gattaacccg ccatgctact tatctaccag ggtaatgggg    180
atcctctaga actatagcta gtcgacattg attattgact agttattaat agtaatcaat    240
tacggggtca ttagttcata gcccatatat ggagttccgc gttacataac ttacggtaaa    300
tggcccgcct ggctgaccgc ccaacgaccc ccgcccattg acgtcaataa tgacgtatgt    360
tcccatagta acgccaatag ggactttcca ttgacgtcaa tgggtggagt atttacggta    420
aactgcccac ttggcagtac atcaagtgta tcatatgcca agtacgcccc ctattgacgt    480
caatgacggt aaatggcccg cctggcatta tgcccagtac atgaccttat gggactttcc    540
tacttggcag tacatctacg tattagtcat cgctattacc atgtcgaggc cacgttctgc    600
ttcactctcc ccatctcccc ccctcccca ccccaattt tgtatttatt tatttttaa       660 ttattttgtg cagcgatggg ggcggggggg ggggcgcgc gccaggcggg gcggggcggg     720
gcgaggggcg gggcggggcg aggcggagag gtgcggcggc agccaatcag agcggcgcgc    780
tccgaaagtt tccttttatg gcgaggcggc ggcggcggcg gccctataaa aagcgaagcg    840
cgcggcgggc gggagcaagc tttattgcgg tagtttatca cagttaaatt gctaacgcag    900
tcagtgcttc tgacacaaca gtctcgaact taagctgcag aagttggtcg tgaggcactg    960
ggcaggtaag tatcaaggtt acaagacagg tttaaggaga ccaatagaaa ctgggcttgt   1020
cgagacagag aagactcttg cgtttctgat aggcacctat tggtcttact gacatccact   1080
ttgcctttct ctccacaggt gtccactccc agttcaatta cagctcttaa ggctagagta   1140
cttaatacga ctcactatag gctagcgcg ccatgggctc catcggcgca gcaagcatgg   1200 aatttttgttt tgatgtattc aaggagctca agtccacca tgccaatgag aacatcttct   1260
actgccccat tgccatcatg tcagctctag ccatggtata cctgggtgca aaagacagca   1320
ccaggacaca aataaataag gttgttcgct ttgataaact tccaggattc ggagacagta   1380
ttgaagctca gtgtggcaca tctgtaaacg ttcactcttc acttagagac atcctcaacc   1440
aaatcaccaa accaaatgat gtttattcgt tcagccttgc cagtagactt tatgctgaag   1500
agagataccc aatcctgcca gaatacttgc agtgtgtgaa ggaactgtat agaggaggct   1560

```
tggaacctat caactttcaa acagctgcag atcaagccag agagctcatc aattcctggg    1620
tagaaagtca gacaaatgga attatcagaa atgtccttca gccaagctcc gtggattctc    1680
aaactgcaat ggttctggtt aatgccattg tcttcaaagg actgtgggag aaaacattta    1740
aggatgaaga cacacaagca atgcctttca gagtgactga gcaagaaagc aaacctgtgc    1800
agatgatgta ccagattggt ttatttagag tggcatcaat ggcttctgag aaaatgaaga    1860
tcctggagct tccatttgcc agtgggacaa tgagcatgtt ggtgctgttg cctgatgaag    1920
tctcaggcct tgagcagctt gagagtataa tcaactttga aaaactgact gaatggacca    1980
gttctaatgt tatggaagag aggaagatca aagtgtactt acctcgcatg aagatggagg    2040
aaaaatacaa cctcacatct gtcttaatgg ctatgggcat tactgacgtg tttagctctt    2100
cagccaatct gtctggcatc tcctcagcag agagcctgaa gatatctcaa gctgtccatg    2160
cagcacatgc agaaatcaat gaagcaggca gagaggtggt agggtcagca gaggctggag    2220
tggatgctgc aagcgtctct gaagaattta gggctgacca tccattcctc ttctgtatca    2280
agcacatcgc aaccaacgcc gttctcttct ttggcagatg tgtttcccct taaaaagaag    2340
aaagctgaaa aactctgtcc cttccaacaa gacccagagc actgtagtat caggggtaaa    2400
atgaaaagta tgttctctgc tgcatccaga cttcataaaa gctggagctt aatctagagt    2460
cgacctgcag aagcttgctg aattctgggg tatttgacaa actgacatgg ggtatttgac    2520
aaactgacag gtacctctag agtcgacccg ggcggcctcg aggacggggt gaactacgcc    2580
tgaggatccg atcttttttcc ctctgccaaa aattatgggg acatcatgaa gccccttgag    2640
catctgactt ctggctaata aaggaaattt attttcattg caatagtgtg ttggaatttt    2700
ttgtgtctct cactcggaag caattcgttg atctgaattt cgaccaccca taatacccat    2760
taccctggta gataagtagc atggcgggtt aatcattaac tacaaggaac ccctagtgat    2820
ggagttggcc actccctctc tgcgcgctcg ctcgctcact gaggccgggc gaccaaaggt    2880
cgcccgacgc ccgggctttg cccgggcggc ctcagtgagc gagcgagcgc gcag          2934
```

<210> SEQ ID NO 35
<211> LENGTH: 2938
<212> TYPE: DNA
<213> ORGANISM: Artificial Sequence
<220> FEATURE:
<223> OTHER INFORMATION: Synthetic

<400> SEQUENCE: 35

```
ctgcgcgctc gctcgctcac tgaggccgcc cgggcaaagc ccgggcgtcg ggcgaccttt      60
ggtcgcccgg cctcagtgag cgagcgagcg cgcagagagg gagtggccaa ctccatcact     120 agggggttcct tgtagttaat gattaacccg ccatgctact tatctaccag ggtaatgggg    180
atcctctaga actatagcta gtcgacattg attattgact agttattaat agtaatcaat    240 tacgggtca ttagttcata gcccatatat ggagttccgc gttacataac ttacggtaaa     300
tggcccgcct ggctgaccgc ccaacgaccc ccgcccattg acgtcaataa tgacgtatgt    360
tcccatagta acgccaatag ggactttcca ttgacgtcaa tgggtggagt atttacggta    420
aactgcccac ttggcagtac atcaagtgta tcatatgcca gtacgcccc ctattgacgt     480 caatgacggt aaatggcccg cctggcatta tgcccagtac atgaccttat ggactttcc    540 tacttggcag tacatctacg tattagtcat cgctattacc atgtcgaggc cacgttctgc    600
ttcactctcc ccatctcccc cccctcccca ccccaatttt gtatttatt tattttttaa     660 ttattttgtg cagcgatggg ggcggggggg ggggcgcgcg ccaggcgggg gcggggcggg    720
```

```
gcgaggggcg ggGcggggcg aggcggagag gtgcggcggc agccaatcag agcggcgcgc    780
tccgaaagtt tccttttatg gcgaggcggc ggcggcgggcg gccctataaa aagcgaagcg    840
cgcggcgggc gggagcaagc tttattgcgg tagtttatca cagttaaatt gctaacgcag    900
tcagtgcttc tgacacaaca gtctcgaact taagctgcag aagttggtcg tgaggcactg    960
ggcaggtaag tatcaaggtt acaagacagg tttaaggaga ccaatagaaa ctgggcttgt   1020
cgagacagag aagactcttg cgtttctgat aggcacctat tggtcttact gacatccact   1080
ttgcctttct ctccacaggt gtccactccc agttcaatta cagctcttaa ggctagagta   1140
cttaatacga ctcactatag gctagcgcg ccatgggctc catcggcgca gcaagcatgg    1200
aattttgttt tgatgtattc aaggagctca agtccacca tgccaatgag aacatcttct   1260
actgccccat tgccatcatg tcagctctag ccatggtata cctgggtgca aaagacagca   1320
ccaggacaca ataaataag gttgttcgct ttgataaact tccaggattc ggagacagta    1380
ttgaagctca gtgtggcaca tctgtaaacg ttcactcttc acttagagac atcctcaacc   1440
aaatcaccaa accaaatgat gtttattcgt tcagccttgc cagtagactt tatgctgaag   1500
agagataccc aatcctgcca gaatacttgc agtgtgtgaa ggaactgtat agaggaggct   1560
tggaacctat caactttcaa acagctgcag atcaagccag agagctcatc aattcctggg   1620
tagaaagtca gacaaatgga attatcagaa atgtccttca gccaagctcc gtggattctc   1680
aaactgcaat ggttctggtt aatgccattg tcttcaaagg actgtgggag aaaacattta   1740
aggatgaaga cacacaagca atgcctttca gagtgactga gcaagaaagc aaacctgtgc   1800
agatgatgta ccagattggt ttatttagag tggcatcaat ggcttctgag aaaatgaaga   1860
tcctggagct tccatttgcc agtgggacaa tgagcatgtt ggtgctgttg cctgatgaag   1920
tctcaggcct tgagcagctt gagagtataa tcaactttga aaaactgact gaatggacca   1980
gttctaatgt tatggaagag aggaagatca aagtgtactt acctcgcatg aagatggagg   2040
aaaaatacaa cctcacatct gtcttaatgg ctatgggcat tactgacgtg tttagctctt   2100
cagccaatct gtctggcatc tcctcagcag agagcctgaa gatatctcaa gctgtccatg   2160
cagcacatgc agaaatcaat gaagcaggca gagaggtggt agggtcagca gaggctggag   2220
tggatgctgc aagcgtctct gaagaattta gggctgacca tccattcctc ttctgtatca   2280
agcacatcgc aaccaacgcc gttctcttct ttggcagatg tgtttcccct taaaaagaag   2340
aaagctgaaa aactctgtcc cttccaacaa gacccagagc actgtagtat caggggtaaa   2400
atgaaaagta tgttctctgc tgcatccaga cttcataaaa gctggagctt aatctagagt   2460
cgacctgcag aagcttgctg aattcgaatg gcaccccctc ctagggttgg aatggcaccc   2520
cctcctaggt ttgggtacct ctagagtcga cccgggcggc ctcgaggacg gggtgaacta   2580
cgcctgagga tccgatcttt ttccctctgc caaaaattat ggggacatca tgaagcccct   2640
tgagcatctg acttctggct aataaaggaa atttattttc attgcaatag tgtgttggaa   2700
ttttttgtgt ctctcactcg gaagcaattc gttgatctga atttcgacca cccataatac   2760
ccattaccct ggtagataag tagcatggcg ggttaatcat taactacaag gaacccctag   2820
tgatggagtt ggccactccc tctctgcgcg ctcgctcgct cactgaggcc gggcgaccaa   2880
aggtcgcccg acgcccgggc tttgcccggg cggcctcagt gagcgagcga gcgcgcag    2938
```

<210> SEQ ID NO 36
<211> LENGTH: 2984
<212> TYPE: DNA

<213> ORGANISM: Artificial Sequence
<220> FEATURE:
<223> OTHER INFORMATION: Synthetic

<400> SEQUENCE: 36

```
ctgcgcgctc gctcgctcac tgaggccgcc cgggcaaagc ccggggcgtcg ggcgaccttt      60
ggtcgcccgg cctcagtgag cgagcgagcg cgcagagagg gagtggccaa ctccatcact     120
aggggttcct tgtagttaat gattaacccg ccatgctact tatctaccag ggtaatgggg     180
atcctctaga actatagcta gtcgacattg attattgact agttattaat agtaatcaat     240
tacggggtca ttagttcata gcccatatat ggagttccgc gttacataac ttacggtaaa     300
tggcccgcct ggctgaccgc ccaacgaccc ccgcccattg acgtcaataa tgacgtatgt     360
tcccatagta acgccaatag ggactttcca ttgacgtcaa tgggtggagt atttacggta     420
aactgcccac ttggcagtac atcaagtgta tcatatgcca gtacgccccc ctattgacgt     480
caatgacggt aaatggcccg cctggcatta tgcccagtac atgaccttat gggactttcc     540
tacttggcag tacatctacg tattagtcat cgctattacc atgtcgaggc cacgttctgc     600
ttcactctcc ccatctcccc ccctccccca cccccaattt tgtatttatt tattttttaa     660
ttattttgtg cagcgatggg ggcgggggg ggggcgcgc gccaggcggg gcggggcggg     720
gcgaggggcg gggcggggcg aggcggagag gtgcggcggc agccaatcag agcggcgcgc     780
tccgaaagtt tccttttatg gcgaggcggc ggcggcggcg gccctataaa aagcgaagcg     840
cgcggcgggc gggagcaagc tttattgcgg tagtttatca cagttaaatt gctaacgcag     900
tcagtgcttc tgacacaaca gtctcgaact taagctgcag aagttggtcg tgaggcactg     960
ggcaggtaag tatcaaggtt acaagacagg tttaaggaga ccaatagaaa ctgggcttgt    1020
cgagacagag aagactcttg cgtttctgat aggcacctat tggtcttact gacatccact    1080
ttgcctttct ctccacaggt gtccactccc agttcaatta cagctcttaa ggctagagta    1140
cttaatacga ctcactatag gctagcgcg ccatgggctc catcggcgca gcaagcatgg    1200
aattttgttt tgatgtattc aaggagctca agtccacca tgccaatgag aacatcttct    1260
actgccccat tgccatcatg tcagctctag ccatggtata cctgggtgca aaagacagca    1320
ccaggacaca aataaataag gttgttcgct ttgataaact tccaggattc ggagacagta    1380
ttgaagctca gtgtggcaca tctgtaaacg ttcactcttc acttagagac atcctcaacc    1440
aaatcaccaa accaaatgat gtttattcgt tcagccttgc cagtagactt tatgctgaag    1500
agagatacccc aatcctgcca gaatacttgc agtgtgtgaa ggaactgtat agaggaggct    1560
tggaacctat caactttcaa acagctgcag atcaagccag agagctcatc aattcctggg    1620
tagaaagtca gacaaatgga attatcagaa atgtccttca gccaagctcc gtggattctc    1680
aaactgcaat ggttctggtt aatgccattg tcttcaaagg actgtgggag aaaacattta    1740
aggatgaaga cacacaagca atgcctttca gagtgactga gcaagaaagc aaacctgtgc    1800
agatgatgta ccagattggt ttatttagag tggcatcaat ggcttctgag aaaatgaaga    1860
tcctggagct tccatttgcc agtgggacaa tgagcatgtt ggtgctgttg cctgatgaag    1920
tctcaggcct tgagcagctt gagagtataa tcaactttga aaaactgact gaatggacca    1980
gttctaatgt tatggaagag aggaagatca agtgtactt acctcgcatg aagatggagg    2040
aaaaatacaa cctcacatct gtcttaatgg ctatgggcat tactgacgtg tttagctctt    2100
cagccaatct gtctggcatc tcctcagcag agagcctgaa gatatctcaa gctgtccatg    2160
cagcacatgc agaaatcaat gaagcaggca gagaggtggt agggtcagca gaggctggag    2220
```

```
tggatgctgc aagcgtctct gaagaattta gggctgacca tccattcctc ttctgtatca    2280
agcacatcgc aaccaacgcc gttctcttct ttggcagatg tgtttcccct taaaaagaag    2340
aaagctgaaa aactctgtcc cttccaacaa gacccagagc actgtagtat cagggtaaa     2400 atgaaaagta tgttctctgc tgcatccaga cttcataaaa gctggagctt aatctagagt    2460
cgacctgcag aagcttgctg aattctccat aaagtaggaa acactacatc cataaagtag    2520
gaaacactac agaatggcac cccctcctag ggttggaatg gcaccccctc ctagggttgg    2580
gtacctctag agtcgacccg ggcggcctcg aggacggggt gaactacgcc tgaggatccg    2640
atctttttcc ctctgccaaa aattatgggg acatcatgaa gccccttgag catctgactt    2700
ctggctaata aaggaaattt attttcattg caatagtgtg ttggaatttt ttgtgtctct    2760
cactcggaag caattcgttg atctgaattt cgaccaccca taatacccat taccctggta    2820
gataagtagc atggcgggtt aatcattaac tacaaggaac ccctagtgat ggagttggcc    2880
actccctctc tgcgcgctcg ctcgctcact gaggccgggc gaccaaaggt cgcccgacgc    2940
ccgggctttg cccgggcggc ctcagtgagc gagcgagcgc gcag                     2984

<210> SEQ ID NO 37
<211> LENGTH: 2980
<212> TYPE: DNA
<213> ORGANISM: Artificial Sequence
<220> FEATURE:
<223> OTHER INFORMATION: Synthetic

<400> SEQUENCE: 37
ctgcgcgctc gctcgctcac tgaggccgcc cgggcaaagc ccgggcgtcg ggcgaccttt      60
ggtcgcccgg cctcagtgag cgagcgagcg cgcagagagg gagtggccaa ctccatcact    120
aggggttcct tgtagttaat gattaacccg ccatgctact tatctaccag ggtaatgggg    180
atcctctaga actatagcta gtcgacattg attattgact agttattaat agtaatcaat    240 tacgggtca ttagttcata gcccatatat ggagttccgc gttacataac ttacggtaaa     300
tggcccgcct ggctgaccgc ccaacgaccc ccgcccattg acgtcaataa tgacgtatgt    360
tcccatagta acgccaatag ggactttcca ttgacgtcaa tgggtggagt atttacggta    420
aactgcccac ttggcagtac atcaagtgta tcatatgcca agtacgcccc ctattgacgt    480
caatgacggt aaatggcccg cctggcatta tgcccagtac atgaccttat gggactttcc    540
tacttggcag tacatctacg tattagtcat cgctattacc atgtcgaggc cacgttctgc    600
ttcactctcc ccatctcccc ccctccccac ccccaatttt gtatttatt tatttttaa      660 ttatttgtg cagcgatggg ggcggggggg ggggcgcgc gccaggcggg gcggggcggg      720 gcgagggggcg gggcggggcg aggcggagag gtgcggcggc agccaatcag agcggcgcgc    780
tccgaaagtt cccttttatg gcgaggcggc ggcggcggcg ccctataaa aagcgaagcg     840 cgcggcgggc gggagcaagc tttattgcgg tagtttatca cagttaaatt gctaacgcag    900
tcagtgcttc tgacacaaca gtctcgaact taagctgcag aagttggtcg tgaggcactg    960
ggcaggtaag tatcaaggtt acaagacagg tttaaggaga ccaatagaaa ctgggcttgt   1020
cgagacagag aagactcttg cgtttctgat aggcacctat tggtcttact gacatccact   1080
ttgcctttct ctccacaggt gtccactccc agttcaatta cagctcttaa ggctagagta   1140
cttaatacga ctcactatag gctagcgcg ccatgggctc catcggcgca gcaagcatgg   1200
aattttgttt tgatgtattc aaggagctca agtccacca tgccaatgag aacatcttct   1260
```

```
actgccccat tgccatcatg tcagctctag ccatggtata cctgggtgca aaagacagca    1320
ccaggacaca aataaataag gttgttcgct ttgataaact tccaggattc ggagacagta    1380
ttgaagctca gtgtggcaca tctgtaaacg ttcactcttc acttagagac atcctcaacc    1440
aaatcaccaa accaaatgat gtttattcgt tcagccttgc cagtagactt tatgctgaag    1500
agagataccc aatcctgcca gaatacttgc agtgtgtgaa ggaactgtat agaggaggct    1560
tggaacctat caactttcaa acagctgcag atcaagccag agagctcatc aattcctggg    1620
tagaaagtca gacaaatgga attatcagaa atgtccttca gccaagctcc gtggattctc    1680
aaactgcaat ggttctggtt aatgccattg tcttcaaagg actgtgggag aaaacattta    1740
aggatgaaga cacacaagca atgcctttca gagtgactga gcaagaaagc aaacctgtgc    1800
agatgatgta ccagattggt ttatttagag tggcatcaat ggcttctgag aaaatgaaga    1860
tcctggagct tccatttgcc agtgggacaa tgagcatgtt ggtgctgttg cctgatgaag    1920
tctcaggcct tgagcagctt gagagtataa tcaactttga aaaactgact gaatggacca    1980
gttctaatgt tatggaagag aggaagatca aagtgtactt acctcgcatg aagatggagg    2040
aaaaatacaa cctcacatct gtcttaatgg ctatgggcat tactgacgtg tttagctctt    2100
cagccaatct gtctggcatc tcctcagcag agagcctgaa gatatctcaa gctgtccatg    2160
cagcacatgc agaaatcaat gaagcaggca gagaggtggt agggtcagca gaggctggag    2220
tggatgctgc aagcgtctct gaagaattta gggctgacca tccattcctc ttctgtatca    2280
agcacatcgc aaccaacgcc gttctcttct ttggcagatg tgtttcccct taaaaagaag    2340
aaagctgaaa aactctgtcc cttccaacaa gacccagagc actgtagtat caggggtaaa    2400
atgaaaagta tgttctctgc tgcatccaga cttcataaaa gctggagctt aatctagagt    2460
cgacctgcag aagcttgctg aattctccat aaagtaggaa acactacatc cataaagtag    2520
gaaacactac atgggtatt tgacaaactg acatgggta tttgacaaac tgacaggtac    2580
ctctagagtc gacccgggcg gcctcgagga cggggtgaac tacgcctgag gatccgatct    2640 tttccctct gccaaaaatt atggggacat catgaagccc cttgagcatc tgacttctgg    2700
ctaataaagg aaatttattt tcattgcaat agtgtgttgg aatttttgt gtctctcact    2760 cggaagcaat tcgttgatct gaatttcgac cacccataat acccattacc ctggtagata    2820
agtagcatgg cgggttaatc attaactaca aggaacccct agtgatggag ttggccactc    2880
cctctctgcg cgctcgctcg ctcactgagg ccgggcgacc aaaggtcgcc cgacgcccgg    2940
gctttgcccg ggcggcctca gtgagcgagc gagcgcgcag                          2980
```

<210> SEQ ID NO 38
<211> LENGTH: 22
<212> TYPE: DNA
<213> ORGANISM: Artificial Sequence
<220> FEATURE:
<223> OTHER INFORMATION: Synthetic

<400> SEQUENCE: 38

```
tggggtattt gacaaactga ca                                               22
```

<210> SEQ ID NO 39
<211> LENGTH: 24
<212> TYPE: DNA
<213> ORGANISM: Artificial Sequence
<220> FEATURE:
<223> OTHER INFORMATION: Synthetic

<400> SEQUENCE: 39
gaatggcacc ccctcctagg gttg                                          24

<210> SEQ ID NO 40
<211> LENGTH: 96
<212> TYPE: DNA
<213> ORGANISM: Artificial Sequence
<220> FEATURE:
<223> OTHER INFORMATION: Synthetic

<400> SEQUENCE: 40
tccataaagt aggaaacact acatccataa agtaggaaac actacagaat ggcacccct   60 cctagggttg gaatggcacc ccctcctagg gttggg                            96

<210> SEQ ID NO 41
<211> LENGTH: 90
<212> TYPE: DNA
<213> ORGANISM: Artificial Sequence
<220> FEATURE:
<223> OTHER INFORMATION: Synthetic

<400> SEQUENCE: 41
tccataaagt aggaaacact acatccataa agtaggaaac actacatggg gtatttgaca   60
aactgacatg gggtatttga caaactgaca                                   90

<210> SEQ ID NO 42
<211> LENGTH: 22
<212> TYPE: RNA
<213> ORGANISM: Artificial Sequence
<220> FEATURE:
<223> OTHER INFORMATION: Synthetic

<400> SEQUENCE: 42
ugggguauuu gacaaacuga ca                                           22

<210> SEQ ID NO 43
<211> LENGTH: 24
<212> TYPE: RNA
<213> ORGANISM: Artificial Sequence
<220> FEATURE:
<223> OTHER INFORMATION: Synthetic

<400> SEQUENCE: 43
gaauggcacc cccuccuagg guug                                          24

<210> SEQ ID NO 44
<211> LENGTH: 96
<212> TYPE: RNA
<213> ORGANISM: Artificial Sequence
<220> FEATURE:
<223> OTHER INFORMATION: Synthetic

<400> SEQUENCE: 44
uccauaaagu aggaaacacu acauccauaa aguaggaaac acuacagaau ggcaccccu   60 ccuaggguug gaauggcacc cccuccuagg guuggg                            96

<210> SEQ ID NO 45
<211> LENGTH: 90
<212> TYPE: RNA
<213> ORGANISM: Artificial Sequence
<220> FEATURE:
<223> OTHER INFORMATION: Synthetic

```
<400> SEQUENCE: 45
uccauaaagu aggaaacacu acauccauaa aguaggaaac acuacauggg guauuugaca        60
aacugacaug ggguauuuga caaacugaca                                        90

<210> SEQ ID NO 46
<211> LENGTH: 8
<212> TYPE: PRT
<213> ORGANISM: Artificial Sequence
<220> FEATURE:
<223> OTHER INFORMATION: Synthetic

<400> SEQUENCE: 46

Ser Ile Ile Asn Phe Glu Lys Leu
1               5
```